United States Patent
Talalay et al.

(10) Patent No.: US 10,869,853 B2
(45) Date of Patent: *Dec. 22, 2020

(54) COMPOSITIONS AND METHODS FOR TREATING AUTISM SPECTRUM DISORDERS

(71) Applicants: THE JOHNS HOPKINS UNIVERSITY, Baltimore, MD (US); Antony Talalay, Lutherville, MD (US)

(72) Inventors: Paul Talalay, Baltimore, MD (US); Andrew Zimmerman, Hopedale, MA (US)

(*) Notice: Subject to any disclaimer, the term of this patent is extended or adjusted under 35 U.S.C. 154(b) by 39 days.

This patent is subject to a terminal disclaimer.

(21) Appl. No.: 15/524,334

(22) PCT Filed: Oct. 2, 2015

(86) PCT No.: PCT/US2015/053657
§ 371 (c)(1),
(2) Date: May 4, 2017

(87) PCT Pub. No.: WO2016/054475
PCT Pub. Date: Apr. 7, 2016

(65) Prior Publication Data
US 2017/0340595 A1  Nov. 30, 2017
US 2020/0093780 A9  Mar. 26, 2020

Related U.S. Application Data

(63) Continuation-in-part of application No. 14/512,175, filed on Oct. 10, 2014, now abandoned, which is a
(Continued)

(51) Int. Cl.
*A61K 31/16* (2006.01)
*A61K 31/26* (2006.01)
(Continued)

(52) U.S. Cl.
CPC ............ *A61K 31/26* (2013.01); *A23L 33/105* (2016.08); *A23L 33/40* (2016.08); *A61K 31/20* (2013.01);
(Continued)

(58) Field of Classification Search
CPC ...................................................... A61K 31/10
(Continued)

(56) References Cited

U.S. PATENT DOCUMENTS 8,937,050 B2 * 1/2015 Talalay ................ A61K 31/145
514/24

FOREIGN PATENT DOCUMENTS

WO  WO-2010140271 A1 * 12/2010 ............. A61K 31/26
WO  WO2013/067040 A1  5/2013
(Continued)

OTHER PUBLICATIONS

Singh, et al., PNAS | Oct. 28, 2014 | vol. 111 | No. 43, pp. 15550-15555.*

(Continued)

*Primary Examiner* — Shengjun Wang
(74) *Attorney, Agent, or Firm* — Cermak Nakajima & McGowan LLP; Malcolm K. McGowan

(57) ABSTRACT

The instant disclosure features, among other things, compositions and methods for treating an autism spectrum disorder in a human. The compositions comprise an effective amount of: (1) an isothiocyanate (e.g., sulforaphane or a derivative thereof) or (2) a glucosinolate, and optionally, an enzyme, to thereby treat an autism spectrum disorder and/or reduce the severity of at least one symptom of the disorder. Methods for preparing such compositions are also featured.

22 Claims, 39 Drawing Sheets

Related U.S. Application Data continuation of application No. 13/665,679, filed on Oct. 31, 2012, now Pat. No. 8,937,050.

(60) Provisional application No. 62/059,594, filed on Oct. 3, 2014, provisional application No. 61/558,486, filed on Nov. 11, 2011, provisional application No. 61/558,094, filed on Nov. 10, 2011, provisional application No. 61/553,509, filed on Oct. 31, 2011.

(51) Int. Cl.
*A61K 31/7048* (2006.01)
*A61K 31/20* (2006.01)
*A61K 31/55* (2006.01)
*A61K 31/53* (2006.01)
*A23L 33/105* (2016.01)
*A23L 33/00* (2016.01)
*A61K 31/70* (2006.01)
*A61K 36/31* (2006.01)

(52) U.S. Cl.
CPC ............ *A61K 31/53* (2013.01); *A61K 31/55* (2013.01); *A61K 31/70* (2013.01); *A61K 31/7048* (2013.01); *A61K 36/31* (2013.01); *A61K 2236/30* (2013.01)

(58) Field of Classification Search
USPC ........................................ 514/599
See application file for complete search history.

(56) References Cited

FOREIGN PATENT DOCUMENTS

WO    WO2014/008361 A2    1/2014
WO    WO-2014008361 A2 *  1/2014    ............. A61K 36/31

OTHER PUBLICATIONS

Hu et al., European Journal of Medicinal Chemistry 64 (2013) 529e539 (Year: 2013).*
Pop-Jordanova et al. Nonlinear Biomedical Physics 2010, 4:4, p. 1-7. (Year: 2010).*
Good, Peter, Neuropsychol Rev (2011) 21:66-67.*
Danielsson, S., et al., "Epilepsy in young adults with autism: a prospective population-based follow-up study of 120 individuals diagnosed in childhood," Epilepsia 2005;46(6):918-923.
Amarendra, "Why do autistic children need to lose weight?" Jul. 21, 2012 [retrieved on Nov. 14, 2015]. Retrieved from the Internet: <http://www.stuartduncan.name/autism/why-do-autistic-children-need-to-lose-weight/>, 6 pp.
International Search Report and Written Opinion for PCT Patent App. No. PCT/US2015/053657 (dated Jan. 4, 2016).
International Preliminary Report on Patentability for PCT Patent App. No. PCT/US2015/053657 (dated Apr. 4, 2017).
Klimesch, W., "EEG alpha and theta oscillations reflect cognitive and memory performance: a review and analysis," Brain Res. Rev. 1999;29:169-195.

* cited by examiner

Fig. 1

| Table S1. Baseline characteristics of patients (n=44) who volunteered for the study. | | | |
|---|---|---|---|
| | Placebo group (n = 15) | Sulforaphane group (n = 29) | p-value |
| Age (Mean ± SD) | 16.6 ± 3.5 | 17.9 ± 3.9 | 0.27 |
| Weight (lbs.) | 154.7 ± 39.7 | 170.9 ± 50.4 | 0.28 |
| BMI | 23.7 ± 5.1 | 25.9 ± 6.5 | 0.26 |
| Head circumference (cm) | 56.3 ± 2.8 | 58.1 ± 2.4 | 0.06 |
| Pulse rate/minute | 88 ± 15 | 80 ± 14 | 0.07 |
| Temperature (F) | 98.6 ± 0.6 | 98.4 ± 0.9 | 0.27 |
| Systolic Blood Pressure (mm Hg) | 117 ± 13 | 119 ± 14 | 0.55 |
| Diastolic Blood Pressure (mm Hg) | 73 ± 6 | 76 ± 8 | 0.31 |
| Abnormal physical exam findings: | | | |
| - Skin | 1/15 | 4/29 | 0.65 |
| - HEENT | 1/15 | 1/29 | 1.0 |
| - Neck/Thyroid | 0/15 | 0/29 | - |
| - Chest/Lungs | 1/15 | 0/29 | 1 |
| - Cardiovascular | 1/15 | 0/29 | 0.33 |
| - Abdominal | 0/15 | 0/29 | - |
| - Neurological | 1/15 | 2/29 | 1.0 |
| - Dysmorphic features | 1/15 | 3/29 | 1.0 |
| Race/Ethnicity: | | | |
| - White | 13/15 | 26/29 | |
| - Black | 0/15 | 2/29 | 0.5 |
| - Hispanic | 1/15 | 0/29 | |
| - Asian | 1/15 | 1/29 | |
| Reported history of fever effects | 11/15 | 23/29 | |
| ADOS Score: | | | |
| - Communication | 6.0 ± 1.9 | 6.6 ± 2.0 | 0.36 |
| - Social Interaction | 11.6 ± 2.0 | 11.2 ± 1.7 | 0.50 |
| - Communication + Social Interaction | 17.6 ± 3.1 | 17.8 ± 3.1 | 0.86 |
| - Stereotyped behavior and restricted interests | 3.6 ± 1.7 | 2.9 ± 1.5 | 0.16 |
| Aberrant Behavior Checklist score (screening and baseline averaged): | | | |
| - Total raw score | 60.0 ± 23.2 | 63.6 ± 25.3 | 0.65 |
| - Irritability subscale | 14.2 ± 8.9 | 13.7 ± 9.3 | 0.89 |
| - Lethargy subscale | 13.9 ± 6.3 | 15.1 ± 7.6 | 0.62 |
| - Stereotypy subscale | 10.3 ± 5.2 | 10.1 ± 4.5 | 0.93 |
| - Hyperactivity subscale | 18.2 ± 8.5 | 19.7 ± 9.3 | 0.59 |
| - Inappropriate speech subscale | | | |
| Social Responsiveness Scale Score (screening and baseline averaged): | | | |
| - Total raw score | 120.1 ± 16.6 | 122.2 ± 24.1 | 0.77 |
| - Awareness subscale | 14.6 ± 2.8 | 15.8 ± 3.8 | 0.30 |
| - Cognition subscale | 21.0 ± 3.4 | 23.2 ± 5.5 | 0.16 |
| - Communication subscale | 41.5 ± 7.1 | 40.9 ± 8.6 | 0.84 |
| - Motivation subscale | 18.4 ± 4.0 | 19.2 ± 4.9 | 0.60 |
| - Mannerisms subscale | 25.2 ± 4.8 | 23.3 ± 6.3 | 0.31 |
| OACIS-Severity score: | | | |
| - General level of autism | 4.53 ± 0.74 | 4.38 ± 0.56 | 0.45 |
| - Social interaction | 4.80 ± 1.01 | 4.51 ± 0.69 | 0.28 |
| - Aberrant/abnormal behavior | 4.20 ± 1.37 | 4.21 ± 0.86 | 0.99 |
| - Repetitive/ritualistic behavior | 4.13 ± 0.83 | 4.14 ± 0.74 | 0.99 |
| - Verbal communication | 4.53 ± 1.36 | 4.45 ± 0.95 | 0.81 |

Fig. 1 (continued)

| | | | |
|---|---|---|---|
| - Non-verbal communication | 4.27 ± 0.96 | 4.10 ± 0.72 | 0.53 |
| - Hyperactivity and inattention | 4.40 ± 0.91 | 4.10 ± 0.90 | 0.31 |
| - Anxiety | 4.33 ± 1.23 | 4.17 ± 0.71 | 0.65 |
| - Sensory sensitivities | 4.40 ± 0.74 | 4.07 ± 0.65 | 0.13 |
| - Restricted and narrow interests | 4.33 ± 0.72 | 4.41 ± 0.63 | 0.70 |
| Hematology labs: | | | |
| - Hematocrit (ref: 37.5 - 51.0%) | 43.7 ± 2.3 | 44.2 ± 2.3 | 0.56 |
| - Hemoglobin (ref: 12.6 - 17.7 g/dL) | 14.9 ± 0.8 | 15.2 ± 0.9 | 0.46 |
| - Mean Corpuscular Hemoglobin (ref: 26.6 - 33.0 pg) | 29.7 ± 1.6 | 29.67 ± 1.5 | 0.89 |
| - Mean corpuscular Hemoglobin Concentration (ref: 31.5 - 35.7 g/dL) | 34.1 ± 0.7 | 34.6 ± 0.7 | 0.06 |
| - Mean Corpuscular Volume (ref: 79 - 97 fL) | 86.4 ± 3.2 | 85.6 ± 4.2 | 0.54 |
| - Platelet count (ref: 150 - 349 x 10E3/uL) | 245.5 ± 47.8 | 251.5 ± 55.5 | 0.74 |
| - RBC count (ref: 4.14 - 5.80 x 10E6/uL) | 5.1 ± 0.3 | 5.2 ± 0.5 | 0.27 |
| - WBC count (ref: 4.0 - 9.1 x 10E3/uL) | 6.9 ± 2.3 | 6.8 ± 1.7 | 0.85 |
| Blood chemistry labs: | | | |
| - Sodium (mEq/L) (ref: 135 - 145 mmol/L) | 139.4 ± 3.4 | 139.8 ± 2.2 | 0.68 |
| - Potassium (ref: 3.4 - 4.8 mmol/L) | 3.7 ± 0.5 | 3.8 ± 0.3 | 0.72 |
| - Chloride (ref: 100 - 108 mmol/L) | 105 ± 3.1 | 105 ± 2.4 | 0.97 |
| - $CO_2$ (ref: 23.0 - 31.9 mmol/L) | 23.6 ± 2.4 | 22.3 ± 3.2 | 0.17 |
| - Anion gap | 10.9 ± 3.5 | 12.5 ± 3.0 | 0.13 |
| - BUN (ref: 8 - 25 mg/dL) | 14 ± 5.1 | 12.7 ± 3.1 | 0.41 |
| - Serum creatinine (ref: 0.60 - 1.50 mg/dL) | 0.8 ± 0.1 | 0.8 ± 0.1 | 0.85 |
| - SGOT (ref: 10 - 40 U/L) | 22.8 ± 6.4 | 22.6 ± 8.6 | 0.92 |
| - SGPT (ref: 10 - 55 U/L) | 18.3 ± 6.1 | 30.0 ± 20.6 | 0.009 |
| - Alkaline phosphatase (ref: 15 - 350 U/L) | 180.9 ± 122.1 | 116.4 ± 50.8 | 0.08 |
| - Total bilirubin (ref: 0.0 - 1.0 mg/dL) | 0.6 ± 0.2 | 0.4 ± 0.3 | 0.12 |
| - TSH (ref: 0.5 - 4.0 uIU/mL) | 1.6 ± 0.9 | 2.0 ± 2.1 | 0.35 |
| Abnormal urinalysis results: | | | |
| - Urine bilirubin | 0/12 | 0/22 | - |
| - Urine glucose | 0/12 | 0/22 | - |
| - Urine ketones | 0/12 | 1/22 | 1.0 |
| - Urine occult blood | 0/12 | 0/22 | - |
| - Urine protein | 1/12 | 2/22 | 1.0 |
| - Urine pH | 6.7 ± 0.8 | 7.0 ± 0.8 | 0.28 |

Fig. 6A

| | | \multicolumn{5}{c|}{Table 1. Effect of Sulforaphane Treatment on Total Scores and Changes in Total Scores} |
|---|---|---|---|---|---|---|
| | A. Aberrant Behavior Checklist (ABC) and Social Responsiveness Scale (SRS) | | | | | |
| | | \multicolumn{5}{c|}{Total and Changes in Mean Total Scores} |
| | | \multicolumn{5}{c|}{Time of Observations (weeks)} |
| Scale | Treatment | 0 | 4 | 10 | 18 | 22 |
| ABC | Placebo | | | | | |
| | Baseline | 60.14 | 59.77 | 58.85 | 58.10 | 57.67 |
| | Intervention Point | 60.14 | 60.54 | 62.15 | 56.10 | 55.83 |
| | Change[a] | 0 | 0.77 ± 1.84 | 3.31 ± 3.50 | -2.00 ± 4.59 | -1.83 ± 6.60 |
| | n | 14 | 13 | 13 | 10 | 6 |
| | Sulforaphane | | | | | |
| | Baseline | 62.77 | 62.77 | 62.34 | 63.88 | 69.16 |
| | Intervention Point | 62.77 | 50.08 | 42.73 | 42.44 | 58.44 |
| | Change[a] | 0 | -12.69 ± 4.17 | -19.61 ± 5.95 | -21.44 ± 4.34 | -10.72 ± 5.07 |
| | n | 26 | 26 | 22 | 25 | 16 |
| | P-Value (between treatments)[b] | -- | 0.035 | 0.002 | <0.001 | 0.33 |
| SRS | Placebo | | | | | |
| | Baseline | 120.21 | 120.21 | 118.85 | 119.55 | 122.00 |
| | Intervention Point | 120.21 | 112.43 | 117.46 | 117.55 | 115.33 |
| | Change[a] | 0 | -7.79 ± 3.09 | -1.38 ± 3.72 | -2.00 ± 3.46 | -6.67 ± 3.82 |
| | n | 14 | 14 | 13 | 11 | 6 |
| | Sulforaphane | | | | | |
| | Baseline | 120.15 | 120.88 | 118.26 | 120.96 | 116.91 |
| | Intervention Point | 120.15 | 106.12 | 103.78 | 100.56 | 109.88 |
| | Change[a] | 0 | -14.76 ± 3.79 | -14.48 ± 5.72 | -20.40 ± 4.54 | -7.03 ± 4.20 |
| | n | 26 | 25 | 23 | 25 | 16 |
| | P-Value (between treatments)[b] | -- | 0.29 | 0.080 | 0.017 | 0.87 |

Fig. 6B

| B. Clinical Global Impression - Improvement (CGI-I) Scores | | | |
|---|---|---|---|
| | Number of subjects' scored as either 'much improved' or 'very much improved' after 18 weeks / total number of subjects (percent of total number evaluated) | | |
| Subscore | Placebo | Sulforaphane | P for-difference[c] |
| Overall level of autism | 0/11 (0%) | 0/26 (0%) | -- |
| Social interaction | 0/11 (0%) | 12/26 (46.2%) | 0.007 |
| Aberrant / abnormal behavior | 1/11 (9.1%) | 14/26 (53.8%) | 0.014 |
| Repetitive and stereotypical behavior | 0/11 (0%) | 6/26 (23.1%) | 0.15 |
| Verbal communication | 0/11 (0%) | 11/26 (42.3%) | 0.015 |
| Non-verbal communication | 1/11 (9.1%) | 5/26 (19.2%) | 0.65 |
| Hyperactivity and inattention | 0/11 (0%) | 3/26 (11.5%) | 0.54 |
| Anxiety | 0/11 (0%) | 2/26 (7.7%) | >0.99 |
| Sensory sensitivities | 0/11 (0%) | 6/26 (23.1%) | 0.15 |
| Restricted & narrow interests | 0/11 (0%) | 0/26 (0%) | -- |

[a] Individuals' scores at 4, 10, 18, or 22 wks were subtracted from the same individual's scores at time zero ("Baseline"); differences were averaged, and are presented as means ± S.E.M. Since number of individuals for whom scores were obtained (n) at each time period varied, so did the baseline score used to calculate each change.

[b] P-values as determined from mixed effects general linear model

[c] by Fisher exact test

Fig. 8

| Table S2. Summary of adverse events reported and safety labs at 18 weeks. | | | |
|---|---|---|---|
| CLINICAL INDICATORS: | Placebo group (n=14) | Sulforaphane group (n=26) | p-value |
| Weight gain (lbs.) | 0.31 ± 6.16 | 4.31 ± 5.87 | 0.05 |
| Heart rate (beats/minute) | 88 ± 15 | 79 ± 13 | 0.06 |
| Temperature (F) | 98.6 ± 0.87 | 98.3 ± 0.81 | 0.28 |
| Vomiting | 1 (7.1%) | 5 (19.2%) | 0.40 |
| Aggressions | 2 (14.3%) | 4 (15.4%) | 1.00 |
| Abdominal pain | 2 (14.3%) | 4 (15.4%) | 1.00 |
| Flatulence | 2 (14.3%) | 4 (15.4%) | 1.00 |
| Irritability | 0 (0%) | 3 (11.5%) | 0.54 |
| Constipation | 2 (14.3%) | 3 (11.5%) | 1.00 |
| Diarrhea | 1 (7.1%) | 3 (11.5%) | 1.00 |
| Fever | 1 (7.1%) | 3 (11.5%) | 1.00 |
| Headache | 0 (0%) | 3 (11.5%) | 0.53 |
| Allergy exacerbation | 0 (0%) | 3 (11.5%) | 0.54 |
| Unprovoked seizures | 0 (0%) | 2 (7.7%) | 0.53 |
| Stubbornness | 0 (0%) | 2 (7.7%) | 0.53 |
| Insomnia | 4 (28.6%) | 2 (7.7%) | 0.16 |
| Cough | 0 (0%) | 2 (7.7%) | 0.53 |
| Agitation | 1 (7.1%) | 1 (3.8%) | 1.00 |
| Crying spells | 1 (7.1%) | 1 (3.8%) | 1.00 |
| Hyperactivity | 2 (14.3%) | 1 (3.8%) | 0.28 |
| OCD | 0 (0%) | 1 (3.8%) | 1.00 |
| Impatience | 0 (0%) | 1 (3.8%) | 1.00 |
| Fidgety | 0 (0%) | 1 (3.8%) | 1.00 |
| Disinhibition | 0 (0%) | 1 (3.8%) | 1.00 |
| SIB | 0 (0%) | 1 (3.8%) | 1.00 |
| Pica | 0 (0%) | 1 (3.8%) | 1.00 |
| Increased appetite | 1 (7.1%) | 1 (3.8%) | 1.00 |
| Mouth sores | 0 (0%) | 1 (3.8%) | 1.00 |
| Daytime sleepiness | 0 (0%) | 1 (3.8%) | 1.00 |
| Sore throat | 0 (0%) | 1 (3.8%) | 1.00 |
| Asthma exacerbation | 0 (0%) | 1 (3.8%) | 1.00 |
| Anxiety | 2 (14.3%) | 0 (0%) | 0.12 |
| Lethargy | 2 (14.3%) | 0 (0%) | 0.12 |
| Burping | 3 (21.4%) | 0 (0%) | 0.03 |
| Decreased appetite | 1 (7.1%) | 0 (0%) | 0.35 |
| Increased urination | 1 (7.1%) | 0 (0%) | 0.35 |
| HEMATOLOGY LABS AT 18 WEEKS: | | | |
| - Hematocrit (ref: 37.5 - 51.0%) | 43.4 ± 3.5 | 43.4 ± 2.5 | 0.99 |
| - Hemoglobin (ref: 12.6 - 17.7 g/dL) | 14.7 ± 1.3 | 14.9 ± 1.0 | 0.51 |
| - Mean Corpuscular Hemoglobin (ref: 26.6 - 33.0 pg) | 29.4 ± 1.2 | 29.7 ± 1.6 | 0.59 |
| - Mean corpuscular Hemogobin Concentration (ref: 31.5 - 35.7 g/dL) | 33.9 ± 0.6 | 34.4 ± 0.8 | 0.09 |
| - Mean Corpuscular Volume (ref: 79 - 97 fL) | 86.6 ± 3.4 | 86.0 ± 3.8 | 0.60 |
| - Platelet count (ref: 150 - 349 x 10E3/uL) | 236.8 ± 44.8 | 237.1 ± 45.2 | 0.98 |
| - RBC count (ref: 4.14 - 5.80 x 10E6/uL) | 5.0 ± 0.4 | 5.1 ± 0.4 | 0.53 |
| - WBC count (ref: 4.0 - 9.1 x 10E3/uL) | 6.3 ± 1.7 | 5.9 ± 1.6 | 0.50 |
| Abnormal Hematology labs (outside of reference range): | | | |
| - Hematocrit | 0/13 | 0/25 | |

Fig. 8 (continued)

| | | | |
|---|---|---|---|
| - Hemoglobin | 0/13 | 0/25 | |
| - MCH | 0/13 | 1/25 | 1.00 |
| - MCHC | 0/13 | 1/25 | 1.00 |
| - MCV | 0/13 | 1/25 | 1.00 |
| - Platelet count | 1/13 | 1/25 | 0.57 |
| - RBC count | 0/13 | 1/25 | 1.00 |
| - WBC count | 1/13 | 2/25 | 1.00 |
| BLOOD CHEMISTRY LABS AT 18 WEEKS: | | | |
| - Sodium (ref: 135 - 145 mmol/L) | 139.8 ± 1.7 | 139.7 ± 1.9 | 0.83 |
| - Potassium (ref: 3.4 - 4.8 mmol/L) | 3.6 ± 0.4 | 3.8 ± 0.3 | 0.30 |
| - Chloride (ref: 100 - 108 mmol/L) | 103.9 ± 2.5 | 103.5 ± 2.3 | 0.64 |
| - CO2 (ref: 23.0 - 31.9 mmol/L) | 23.6 ± 2.0 | 24.2 ± 2.6 | 0.51 |
| - Anion gap | 12.3 ± 2.9 | 12.0 ± 2.2 | 0.48 |
| - BUN (ref: 8 - 25 mg/dL) | 12.3 ± 2.8 | 13.0 ± 3.4 | 0.57 |
| - Serum creatinine (ref: 0.60 - 1.50 mg/dL) | 0.8 ± 0.1 | 0.8 ± 0.1 | 0.34 |
| - SGOT (ref: 10 - 40 U/L) | 22.5 ± 9.2 | 22.5 ± 5.4 | 0.98 |
| - SGPT (ref: 10 - 55 U/L) | 22.2 ± 20.1 | 31.1 ± 20.7 | 0.22 |
| - Alkaline phosphatase (ref: 15 - 350 U/L) | 136.9 ± 52.5 | 112.5 ± 53.2 | 0.19 |
| - Total bilirubin (ref: 0.0 - 1.0 mg/dL) | 0.6 ± 0.3 | 0.5 ± 0.3 | 0.54 |
| - TSH (ref: 0.5 - 4.0 uIU/mL) | 1.5 ± 0.6 | 1.9 ± 1.1 | 0.19 |
| Abnormal blood chemistry labs (outside of reference range): | | | |
| - SGPT | 1/13 | 4/24 | 0.64 |
| - CO2 | 5/13 | 6/24 | 0.46 |
| - Sodium | 0/13 | 1/24 | 1.00 |
| - Potassium | 2/13 | 1/24 | 0.28 |
| - Chloride | 1/13 | 1/24 | 1.00 |
| - BUN | 1/13 | 1/24 | 1.00 |
| - Serum creatinine | 0/13 | 0/24 | - |
| - SGOT | 1/13 | 0/24 | 0.35 |
| - Alkaline phosphatase | 0/13 | 0/24 | - |
| - Total bilirubin | 1/13 | 2/24 | 1.00 |
| - TSH | 1/13 | 1/24 | 1.00 |
| URINALYSIS AT 18 WEEKS: | | | - |
| - Urine bilirubin | 0/13 | 0/24 | - |
| - Urine glucose | 0/13 | 1/24 | 1.00 |
| - Urine ketones | 0/13 | 1/24 | 1.00 |
| - Urine occult blood | 0/13 | 0/24 | - |
| - Urine protein | 1/13 | 0/24 | 0.35 |
| Urine pH (ref: 5.0 - 7.5) | 6.8 ± 0.5 | 7.2 ± 0.8 | 0.03 |
| Urine pH outside of reference range | 1/13 | 7/24 | 0.22 |

Fig. 9

| Subject ID | Week | HEMATOLOGY | | | | | | | | |
|---|---|---|---|---|---|---|---|---|---|---|
| | | HCT | HGB | MCH | MCHC | MCV | PLT | RBC | RDW | WBC |
| | | PLACEBO | | | | | | | | |
| 2 | 0 | 44.3 | 15.8 | 31.5 | 35.7 | 88 | 193 | 5.03 | 11.9 | 4.3 |
| | 4 | 49.3 | 16.6 | 31.1 | 33.7 | 93 | 188 | 5.33 | 13.1 | 4.3 |
| | 18 | 49.3 | 16.6 | 31.1 | 33.7 | 93 | 188 | 5.33 | 13.1 | 4.3 |
| | 22 | 46 | 15.8 | 32 | 32.9 | 92 | 185 | 5.21 | 12.8 | 4.4 |
| 5 | 0 | 43.3 | 15 | 27.9 | 33.3 | 82 | 209 | 5.11 | 13 | 5.5 |
| | 4 | 43.1 | 14.4 | 28.1 | 33.4 | 84 | 208 | 5.12 | 13.1 | 5 |
| | 18 | 43.1 | 14.4 | 28.1 | 33.4 | 84 | 208 | 5.12 | 13.1 | 5 |
| | 22 | . | . | . | . | . | . | . | . | . |
| 6 | 0 | 46.2 | 15.5 | 27.9 | 33.5 | 83 | 241 | 5.55 | 13.5 | 5.8 |
| | 4 | 46.4 | 14.9 | 29 | 34.1 | 83 | 240 | 5.45 | 13.5 | 5.9 |
| | 18 | 44.1 | 15.4 | 28.4 | 34.9 | 81 | 253 | 5.42 | 13.4 | 5.9 |
| | 22 | . | . | . | . | . | . | . | . | . |
| 9 | 0 | 42.5 | 14.7 | 31.1 | 34 | 88 | 221 | 4.57 | 12.5 | 5.1 |
| | 4 | 43.5 | 15.1 | 30.4 | 34.7 | 88 | 223 | 4.97 | 12.1 | 5.2 |
| | 18 | 40.4 | 13.5 | 29.9 | 34.4 | 87 | 225 | 4.57 | 12.5 | 4.9 |
| | 22 | 42.2 | 14 | 30.1 | 35.1 | 87 | 224 | 4.7 | 12.7 | 4.4 |
| 14 | 0 | 47.1 | 16.1 | 29.9 | 34.2 | 88 | 233 | 5.38 | 13.1 | 7.7 |
| | 4 | 47.9 | 16.6 | 29.7 | 34.7 | 86 | 229 | 5.58 | 12.7 | 9.3 |
| | 18 | 50 | 17 | 29 | 33.9 | 86 | 233 | 5.7 | 12.9 | 8 |
| | 22 | 50 | 17 | 29.7 | 34 | 87 | 236 | 5.73 | 13 | 8.1 |
| 18 | 0 | 43.6 | 15 | 31.7 | 34.4 | 92 | 235 | 4.73 | 13 | 7.2 |
| | 4 | 42 | 14 | 33.9 | 31.1 | 91 | 233 | 4.59 | 13.9 | 7 |
| | 18 | 41 | 13 | 29.9 | 33.9 | 86 | 210 | 5.1 | 15 | 6.6 |
| | 22 | 43.1 | 14.7 | 31.1 | 34.1 | 91 | 252 | 4.72 | 13 | 8 |
| 19 | 0 | 45.3 | 15.5 | 29.5 | 34.2 | 86 | 261 | 5.25 | 13.1 | 8.4 |
| | 4 | 44 | 15.1 | 29.3 | 34.3 | 85 | 216 | 5.18 | 13.3 | 8.7 |
| | 18 | 43.2 | 14.7 | 29.2 | 34 | 86 | 216 | 5.023 | 13.6 | 7.7 |
| | 22 | 45.9 | 15.7 | 29.2 | 34.2 | 86 | 222 | 5.37 | 13.3 | 6.8 |

Fig. 9 (continued)

| Subject ID | Week | HEMATOLOGY | | | | | | | | |
|---|---|---|---|---|---|---|---|---|---|---|
| | | HCT | HGB | MCH | MCHC | MCV | PLT | RBC | RDW | WBC |
| 24 | 0 | 42.1 | 14.1 | 28.5 | 33.5 | 85 | 219 | 4.95 | 13.9 | 6.1 |
| | 4 | 44 | 15.1 | 29.3 | 34.3 | 85 | 161 | 5.15 | 14 | 3.8 |
| | 18 | 41.9 | 14.3 | 29.1 | 34.1 | 85 | 228 | 4.92 | 14.1 | 6.8 |
| | 22 | - | - | - | - | - | - | - | - | - |
| 29 | 0 | 47 | 16.9 | 30 | 34.8 | 87 | 190 | 5.27 | 13.1 | 6.6 |
| | 4 | 44.9 | 15.7 | 31.2 | 35 | 89 | 240 | 5.03 | 12.9 | 5.9 |
| | 18 | 47.1 | 16.6 | 31.6 | 35.2 | 90 | 193 | 5.26 | 13 | 5.1 |
| | 22 | 47.7 | 16.6 | 31.5 | 34.8 | 91 | 114 | 5.27 | 13.1 | 6 |
| 33 | 0 | 43.4 | 14.6 | 28.5 | 33.6 | 85 | 227 | 5.13 | 13.4 | 5.2 |
| | 4 | 47.1 | 16.2 | 28.8 | 34.4 | 84 | 244 | 5.63 | 13.4 | 5.8 |
| | 18 | 43 | 14.3 | 28.3 | 33.3 | 85 | 229 | 5.06 | 13.4 | 5.2 |
| | 22 | 43.8 | 14.8 | 28.1 | 33.8 | 83 | 238 | 5.27 | 14.5 | 6.1 |
| 34 | 0 | 38.5 | 13.2 | 30.8 | 34.3 | 90 | 248 | 4.28 | 13.4 | 5.6 |
| | 4 | 40.5 | 13.7 | 31.1 | 33.8 | 92 | 269 | 4.41 | 13.8 | 5.5 |
| | 18 | 40.8 | 13.6 | 30.2 | 33.3 | 91 | 244 | 4.5 | 13.2 | 5.2 |
| | 22 | 42.5 | 14.1 | 29.9 | 33.2 | 90 | 274 | 4.72 | 13.2 | 5.2 |
| 36 | 0 | 42.3 | 14.2 | 27 | 33.6 | 81 | 374 | 5.26 | 13.6 | 13.3 |
| | 4 | 41.5 | 14.3 | 27.4 | 34.5 | 86 | 362 | 5.21 | 13.9 | 8.6 |
| | 18 | 42.5 | 14.1 | 27.5 | 33.2 | 83 | 355 | 5.12 | 13.7 | 8.7 |
| | 22 | - | - | - | - | - | - | - | - | - |
| 41 | 0 | - | - | - | - | - | - | - | - | - |
| | 4 | 39.7 | 13.6 | 29.4 | 34.3 | 86 | 220 | 4.62 | 14.7 | 8.4 |
| | 18 | 38.2 | 12.9 | 30.1 | 33.8 | 89 | 208 | 4.29 | 14 | 9.5 |
| | 22 | - | - | - | - | - | - | - | - | - |
| 43 | 0 | 43.1 | 14.8 | 32 | 34.3 | 86 | 260 | 5.1 | 14 | 8.8 |
| | 4 | 44.5 | 14.5 | 26.7 | 32.6 | 82 | 266 | 5.43 | 14.3 | 9.4 |
| | 18 | - | - | - | - | - | - | - | - | - |
| | 22 | - | - | - | - | - | - | - | - | - |

Fig. 9 (Continued)

| Subject ID | Week | HEMATOLOGY ||||||||| 
| | | HCT | HGB | MCH | MCHC | MCV | PLT | RBC | RDW | WBC |
|---|---|---|---|---|---|---|---|---|---|---|
| | | | | | SULFORAPHANE TREATED |||||| 
| 1 | 0 | 45.7 | 15.4 | 28.7 | 33.7 | 85 | 314 | 5.37 | 13.8 | 7.4 |
| | 4 | 43.5 | 14.9 | 28.3 | 34.3 | 83 | 279 | 5.27 | 13.8 | 8 |
| | 18 | 43.8 | 14.8 | 28.3 | 33.8 | 84 | 282 | 5.23 | 14.2 | 7.5 |
| | 22 | 42.5 | 14.4 | 28.1 | 33.8 | 83 | 334 | 5.12 | 13.8 | 8 |
| 3 | 0 | 45 | 15.3 | 29.6 | 34 | 88 | 266 | 5.13 | 13 | 6.6 |
| | 4 | 45.6 | 15.4 | 29.3 | 33.8 | 87 | 279 | 5.26 | 12.8 | 6 |
| | 18 | 44.4 | 15.5 | 29.6 | 34.9 | 85 | 226 | 5.23 | 13.1 | 5.9 |
| | 22 | . | . | . | . | . | . | . | . | . |
| 4 | 0 | 44.4 | 15.5 | 29.6 | 34.9 | 85 | 226 | 5.23 | 13.1 | 8.8 |
| | 4 | 44 | 15 | 29.9 | 35 | 84 | 225 | 5.22 | 13.2 | 9.3 |
| | 18 | 43 | 14.7 | 30.1 | 34.2 | 88 | 297 | 4.88 | 13.7 | 9.6 |
| | 22 | 44.7 | 15 | 30 | 34 | 87 | 294 | 4.69 | 13.1 | 9 |
| 7 | 0 | 45.7 | 15.9 | 30.2 | 34.8 | 87 | 179 | 5.26 | 13.4 | 4.1 |
| | 4 | 45 | 15 | 30.3 | 34.7 | 88 | 184 | 5.22 | 13.6 | 3.8 |
| | 18 | 44 | 15.6 | 30.4 | 35.5 | 86 | 162 | 5.14 | 13.5 | 2.6 |
| | 22 | 45.7 | 15 | 30.2 | 34.6 | 87 | 184 | 5.21 | 13.5 | 2.7 |
| 8 | 0 | 45.9 | 15.9 | 30.2 | 34.6 | 87 | 211 | 5.26 | 12.6 | 7.4 |
| | 4 | 46.5 | 16.2 | 30.5 | 34.8 | 88 | 225 | 5.31 | 12.7 | 6.3 |
| | 18 | 44.4 | 13.1 | 30.1 | 33.3 | 87 | 222 | 5.29 | 12.3 | 6.6 |
| | 22 | 44.4 | 16.1 | 30.1 | 33.3 | 87 | 222 | 5.29 | 12.3 | 6.6 |

Fig. 9 (Continued)

| Subject ID | Week | HEMATOLOGY ||||||||| 
|---|---|---|---|---|---|---|---|---|---|---|
| | | HCT | HGB | MCH | MCHC | MCV | PLT | RBC | RDW | WBC |
| 10 | 0 | - | - | - | - | - | - | - | - | - |
| | 4 | 41 | 14.4 | 29 | 35 | 83 | 260 | 4.9 | 12.45 | 5.5 |
| | 18 | 41.2 | 14.2 | 28.6 | 34.5 | 83 | 254 | 4.96 | 12.5 | 5.1 |
| | 22 | 42 | 14.3 | 28.3 | 25 | 83 | 261 | 4.88 | 12.4 | 5.2 |
| 11 | 0 | 39 | 14 | 29.1 | 33.1 | 86 | 220 | 4.6 | 13 | 5.9 |
| | 4 | 41.9 | 15 | 31 | 31 | 86 | 210 | 4.5 | 14 | 6.2 |
| | 18 | 38.9 | 13.2 | 29.5 | 33.9 | 87 | 213 | 4.47 | 14.1 | 5.3 |
| | 22 | 38.9 | 13.2 | 29.5 | 33.9 | 87 | 213 | 4.47 | 14.1 | 5.3 |
| 12 | 0 | 46.1 | 14.9 | 29 | 35 | 81 | 220 | 5.3 | 13 | 5.5 |
| | 4 | 45 | 15.9 | 31 | 35 | 81 | 210 | 5.2 | 12.1 | 5.7 |
| | 18 | 47.9 | 16.8 | 29 | 35.1 | 86 | 222 | 5.8 | 13.9 | 5.4 |
| | 22 | - | - | - | - | - | - | - | - | - |
| 13 | 0 | 45.1 | 16 | 27.9 | 34.9 | 81 | 219 | 5.9 | 12.9 | 5.4 |
| | 4 | 47.3 | 16.5 | 29 | 34.9 | 83 | 227 | 5.69 | 14 | 5.4 |
| | 18 | 47.3 | 16.5 | 29 | 34.9 | 83 | 227 | 5.69 | 14 | 5.4 |
| | 22 | - | - | - | - | - | - | - | - | - |
| 15 | 0 | 42.1 | 14 | 32.9 | 35 | 86 | 291 | 4.4 | 12.9 | 7.1 |
| | 4 | 39.9 | 13.5 | 19.7 | 33.9 | 86 | 301 | 4.54 | 13.6 | 6.8 |
| | 18 | 40 | 13.9 | 31 | 34.4 | 86 | 291 | 4.9 | 13.9 | 6.6 |
| | 22 | 36 | 14.5 | 26 | 34 | 87 | 290 | 5.5 | 14.1 | 6.9 |
| 16 | 0 | 47.2 | 16.4 | 29.2 | 34.7 | 84 | 237 | 5.62 | 14 | 7.5 |
| | 4 | 45.7 | 15.8 | 28.9 | 34.6 | 84 | 249 | 5.47 | 14.1 | 6.5 |
| | 18 | - | - | - | - | - | - | - | - | - |
| | 22 | 45 | 15.5 | 28.3 | 35 | 84 | 248 | 5.55 | 13.9 | 6.6 |
| 17 | 0 | 44.5 | 15.1 | 30.7 | 34.2 | 86 | 222 | 4.92 | 13.3 | 4.2 |
| | 4 | 42.6 | 14.9 | 30.6 | 35 | 86 | 183 | 4.87 | 13.3 | 4.8 |
| | 18 | 44 | 15.5 | 31 | 35.2 | 86 | 195 | 4.88 | 13.1 | 4.4 |
| | 22 | 42 | 14 | 30.6 | 33 | 86 | 196 | 4.8 | 13.9 | 4.8 |

Fig. 9 (Continued)

| Subject ID | Week | HEMATOLOGY | | | | | | | | |
|---|---|---|---|---|---|---|---|---|---|---|
| | | HCT | HGB | MCH | MCHC | MCV | PLT | RBC | RDW | WBC |
| 21 | 0 | 42.3 | 14.3 | 28.5 | 33.8 | 84 | 229 | 5.02 | 13.8 | 4.6 |
| | 4 | 43.9 | 15 | 28.4 | 34.2 | 83 | 225 | 5.29 | 13.8 | 4.9 |
| | 18 | 41 | 13 | 33.9 | 35.1 | 86 | 230 | 5.5 | 12 | 5 |
| | 22 | 42.7 | 15.4 | 29.1 | 36.1 | 81 | 268 | 5.3 | 12.3 | 6.1 |
| 23 | 0 | 44 | 15.5 | 30.1 | 35.2 | 86 | 253 | 5.15 | 14.3 | 9.8 |
| | 4 | 44 | 15.2 | 29.5 | 34.6 | 85 | 268 | 5.18 | 14.3 | 9.1 |
| | 18 | 43.6 | 15.3 | 28.8 | 35.1 | 85 | 271 | 5.13 | 14.8 | 9 |
| | 22 | 47.5 | 16.5 | 30.6 | 35.1 | 87 | 266 | 5.4 | 14.6 | 8.2 |
| 26 | 0 | 45.7 | 15.6 | 29 | 34.1 | 85 | 224 | 5.38 | 13.7 | 4.1 |
| | 4 | 44.9 | 15.3 | 29.7 | 34.1 | 87 | 282 | 5.15 | 14 | 5.4 |
| | 18 | 44.1 | 15 | 29.5 | 34 | 87 | 271 | 5.08 | 13.7 | 4.3 |
| | 22 | - | - | - | - | - | - | - | - | - |
| 27 | 0 | 45 | 13.9 | 29 | 35.3 | 87 | 230 | 5.8 | 14.1 | 5.5 |
| | 4 | 48.3 | 16.5 | 31 | 35.6 | 86 | 254 | 5.6 | 13.9 | 5.9 |
| | 18 | 47 | 15.5 | 27.2 | 33 | 83 | 284 | 5.89 | 14.3 | 5.8 |
| | 22 | 48 | 15 | 27.2 | 31.3 | 87 | 266 | 5.52 | 13.1 | 4.3 |
| 28 | 0 | 41 | 15 | 28.8 | 35.9 | 79 | 219 | 5.9 | 13 | 4.4 |
| | 4 | 44 | 13.9 | 27 | 31 | 86 | 222 | 5.5 | 12.1 | 6.6 |
| | 18 | 42.9 | 14.3 | 27.6 | 33.3 | 83 | 205 | 5.19 | 13.9 | 7.3 |
| | 22 | - | - | - | - | - | - | - | - | - |
| 30 | 0 | 46.2 | 15.6 | 27.6 | 35 | 79 | 174 | 5.73 | 13.7 | 6.7 |
| | 4 | 43.9 | 15.4 | 28.5 | 35.2 | 81 | 163 | 5.4 | 13.8 | 6.3 |
| | 18 | 42 | 14.4 | 27.3 | 34.3 | 86 | 173 | 5.28 | 13.3 | 5.1 |
| | 22 | - | - | - | - | - | - | - | - | - |
| 31 | 0 | 41.5 | 13.3 | 29.3 | 33.3 | 86 | 310 | 4.7 | 14 | 7 |
| | 4 | 40.3 | 13.6 | 29.2 | 33.7 | 87 | 240 | 4.66 | 14.4 | 4.1 |
| | 18 | 41.1 | 13.6 | 29.1 | 33.1 | 86 | 247 | 4.68 | 14.2 | 4.5 |
| | 22 | 41.5 | 13.9 | 29.3 | 33.5 | 87 | 333 | 4.75 | 14 | 6.9 |

Fig. 9 (Continued)

| Subject ID | Week | HEMATOLOGY | | | | | | | | |
|---|---|---|---|---|---|---|---|---|---|---|
| | | HCT | HGB | MCH | MCHC | MCV | PLT | RBC | RDW | WBC |
| 32 | 0 | 47.8 | 16.1 | 29.4 | 33.7 | 87 | 243 | 5.49 | 13.1 | 7.5 |
| | 4 | 45 | 15 | 28.8 | 33.3 | 84 | 219 | 5.1 | 13.1 | 6.1 |
| | 18 | 44.9 | 15.3 | 29 | 34.1 | 85 | 225 | 5.27 | 13.3 | 5.9 |
| | 22 | - | - | - | - | - | - | - | - | - |
| 36 | 0 | 44.3 | 15.3 | 29.8 | 34.5 | 86 | 234 | 5.14 | 13.4 | 9.6 |
| | 4 | 46.1 | 15.5 | 30 | 33.6 | 89 | 228 | 5.17 | 12.4 | 10.2 |
| | 18 | 46.3 | 13.2 | 30.3 | 35 | 87 | 259 | 5.34 | 13.6 | 8.4 |
| | 22 | 47.2 | 16 | 29.5 | 33.9 | 87 | 276 | 5.4 | 13.2 | 9.3 |
| 37 | 0 | 39.9 | 13.6 | 29.6 | 34.6 | 85 | 334 | 4.67 | 13.4 | 5.9 |
| | 4 | 39.9 | 14.1 | 29.8 | 35.3 | 84 | 279 | 4.73 | 13.3 | 4.8 |
| | 18 | 40 | 14.5 | 30.3 | 36.3 | 84 | 310 | 4.78 | 13.7 | 4.4 |
| | 22 | 40.6 | 14.3 | 30 | 35.2 | 85 | 284 | 4.76 | 13.3 | 4.8 |
| 38 | 0 | 40.5 | 14.1 | 33.7 | 34.8 | 97 | 328 | 4.19 | 12.5 | 6 |
| | 4 | 43.1 | 14.4 | 32.4 | 33.4 | 97 | 279 | 4.45 | 12.8 | 5 |
| | 18 | 44.2 | 14.8 | 32.7 | 33.5 | 98 | 267 | 4.52 | 12.9 | 4.6 |
| | 22 | 43.1 | 14.6 | 32.5 | 33.9 | 96 | 268 | 4.49 | 12.6 | 3.7 |
| 40 | 0 | 45.4 | 15.8 | 30.3 | 34.8 | 87 | 259 | 5.22 | 13.1 | 7.4 |
| | 4 | 43.3 | 15 | 29.4 | 34.6 | 85 | 233 | 5.1 | 13.3 | 8 |
| | 18 | 43.1 | 14.9 | 29.8 | 34.6 | 86 | 228 | 5 | 13.5 | 7.6 |
| | 22 | - | - | - | - | - | - | - | - | - |
| 42 | 0 | 42.2 | 14.2 | 31.6 | 33.6 | 94 | 135 | 4.5 | 14 | 6.4 |
| | 4 | 42.6 | 14.4 | 31.6 | 33.8 | 93 | 148 | 4.56 | 13.8 | 6.6 |
| | 18 | 39.8 | 13.7 | 31.6 | 34.4 | 92 | 117 | 4.33 | 13.6 | 5.9 |
| | 22 | 43.1 | 14.8 | 32 | 34.3 | 93 | 132 | 4.63 | 14 | 6.6 |
| 44 | 0 | 45.2 | 15.9 | 28 | 35.2 | 80 | 240 | 5.67 | 13.2 | 7.4 |
| | 4 | 45.7 | 15.6 | 28 | 34.1 | 82 | 228 | 5.57 | 13.4 | 7.1 |
| | 18 | 47.3 | 16.1 | 27.4 | 34 | 80 | 239 | 5.88 | 13.4 | 6.6 |
| | 22 | - | - | - | - | - | - | - | - | - |

Fig. 9 (Continued)

| Subject ID | Week | URINALYSIS ||||||||||||
| --- | --- | --- | --- | --- | --- | --- | --- | --- | --- | --- | --- | --- | --- |
| | | Bili | Color | Gluc | Ketone | Nitrate | Occult Blood | pH | Prot | Spec Grav | Turbid | Urobil | WBC Est |
| PLACEBO |||||||||||||||
| 2 | 0 | Neg | Y | Neg | Neg | Neg | Neg | 6 | Neg | 1.01 | Clear | 0.2 | Neg |
| | 4 | Neg | Y | Neg | Neg | Neg | Neg | 6.5 | Neg | 1.021 | Clear | 0.2 | Neg |
| | 18 | Neg | Y | Neg | Neg | Neg | Neg | 6.5 | Neg | 1.021 | Clear | 0.2 | Neg |
| | 22 | Neg | Y | Neg | Neg | Neg | Neg | 5.8 | Neg | 1.018 | Clear | 0.2 | Neg |
| 5 | 0 | Neg | Y | Neg | Neg | Neg | Neg | 8 | Neg | 1.02 | Clear | 0.2 | Neg |
| | 4 | Neg | Y | Neg | Neg | Neg | Neg | 7 | Neg | 1.017 | Cloudy | 0.2 | Neg |
| | 18 | Neg | Y | Neg | Neg | Neg | Neg | 7 | Neg | 1.017 | Cloudy | 0.2 | Neg |
| | 22 | - | - | - | - | - | - | - | - | - | - | - | - |
| 6 | 0 | Neg | Y | Neg | Neg | Neg | Neg | 8 | Neg | 1.025 | Cloudy | 0.2 | Neg |
| | 4 | Neg | Y | Neg | Neg | Neg | Neg | 8 | Neg | 1.02 | Cloudy | 0.2 | Neg |
| | 18 | Neg | Y | Neg | Neg | Neg | Neg | 7 | Neg | 1.025 | Clear | 0.2 | Neg |
| | 22 | - | - | - | - | - | - | - | - | - | - | - | - |
| 9 | 0 | Neg | Y | Neg | Neg | Neg | Neg | 5.5 | Neg | 1.005 | Clear | 0.2 | Neg |
| | 4 | Neg | Y | Neg | Neg | Neg | Neg | 6 | Neg | 1.007 | Clear | 0.2 | Neg |
| | 18 | Neg | Y | Neg | Neg | Neg | Neg | 7 | Trace | 1.03 | Clear | 1 | Neg |
| | 22 | Neg | Y | Neg | Neg | Neg | Neg | 7.1 | Neg | 1.029 | Clear | 0.2 | Neg |
| 14 | 0 | Neg | Y | Neg | Neg | Neg | Neg | 6 | Neg | 1.021 | Clear | 1 | Neg |
| | 4 | Neg | Y | Neg | Neg | Neg | Neg | 6 | Neg | 1.021 | Clear | 1 | Neg |
| | 18 | Neg | Y | Neg | Neg | Neg | Neg | 6 | Neg | 1.012 | Clear | 0.2 | Neg |
| | 22 | Neg | Y | Neg | Neg | Neg | Neg | 6 | Neg | 1.016 | Clear | 0.2 | Neg |
| 18 | 0 | Neg | Y | Neg | Neg | Neg | Neg | 7 | Neg | 1.01 | Clear | 0.2 | Neg |
| | 4 | - | - | - | - | - | - | - | - | - | - | - | - |
| | 18 | Neg | Y | Neg | Neg | Neg | Neg | 7.9 | Neg | 1.004 | Clear | 0.2 | Neg |
| | 22 | Neg | Y | Neg | Neg | Neg | Neg | 6.5 | Neg | 1.03 | Clear | 0.2 | Neg |
| 19 | 0 | Neg | Y | Neg | Neg | Neg | Neg | 6.5 | 1+ | 1.006 | Clear | 0.2 | Neg |
| | 4 | - | - | - | - | - | - | - | - | - | - | - | - |
| | 18 | Neg | Y | Neg | Neg | Neg | Neg | 6.5 | Neg | 1.023 | Clear | 0.2 | Neg |

Fig. 9 (Continued)

|    |    |     |   |     |     |     |     |     |     |       |        |     |     |
|----|----|-----|---|-----|-----|-----|-----|-----|-----|-------|--------|-----|-----|
|    | 22 | Neg | Y | Neg | Neg | Neg | Neg | 6.5 | Neg | 1.028 | Clear  | 0.2 | Neg |
| 24 | 0  | Neg | Y | Neg | Neg | Neg | Neg | 6   | Neg | 1.023 | Clear  | 0.2 | Neg |
|    | 4  | Neg | Y | Neg | Neg | Neg | Neg | 6.5 | Neg | 1.021 | Cloudy | 0.2 | Neg |
|    | 18 | Neg | Y | Neg | Neg | Neg | Neg | 6.5 | Neg | 1.03  | Clear  | 0.2 | Neg |
|    | 22 | -   | - | -   | -   | -   | -   | -   | -   | -     | -      | -   | -   |
| 29 | 0  | Neg | Y | Neg | Neg | Neg | Neg | 7   | Neg | 1.005 | Clear  | 0.2 | Neg |
|    | 4  | Neg | Y | Neg | Neg | Neg | Neg | 7.5 | Neg | 1.013 | Clear  | 0.2 | Neg |
|    | 18 | Neg | Y | Neg | Neg | Neg | Neg | 7   | Neg | 1.007 | Clear  | 0.2 | Neg |
|    | 22 | Neg | Y | Neg | Neg | Neg | Neg | 7.5 | Neg | 1.007 | Clear  | 0.2 | Neg |
| 33 | 0  | Neg | Y | Neg | Neg | Neg | Neg | 7.5 | Neg | 1.01  | Clear  | 0.2 | Neg |
|    | 4  | Neg | Y | Neg | Neg | Neg | Neg | 6.5 | Neg | 1.008 | Clear  | 0.2 | Neg |
|    | 18 | Neg | Y | Neg | Neg | Neg | Neg | 6.5 | Neg | 1.012 | Clear  | 0.2 | Neg |
|    | 22 | Neg | Y | Neg | Neg | Neg | Neg | 6.5 | Neg | 1.01  | Clear  | 0.2 | Neg |
| 34 | 0  | Neg | Y | Neg | Neg | Neg | Neg | 6   | Neg | 1.009 | Clear  | 0.2 | Neg |
|    | 4  | Neg | Y | Neg | Neg | Neg | Neg | 7.5 | Neg | 1.01  | Clear  | 0.2 | Neg |
|    | 18 | Neg | Y | Neg | Neg | Neg | Neg | 6.5 | Neg | 1.009 | Cloudy | 1   | Neg |
|    | 22 | Neg | Y | Neg | Neg | Neg | Neg | 7.5 | Neg | 1.014 | Clear  | 1   | Neg |
| 36 | 0  | -   | - | -   | -   | -   | -   | -   | -   | -     | -      | -   | -   |
|    | 4  | Neg | Y | Neg | Neg | Neg | Neg | 6.5 | Neg | 1.03  | Clear  | 1   | Neg |
|    | 18 | Neg | Y | Neg | Neg | Neg | Neg | 7   | Neg | 1.03  | Clear  | 1   | Neg |
|    | 22 | -   | - | -   | -   | -   | -   | -   | -   | -     | -      | -   | -   |
| 41 | 0  | -   | - | -   | -   | -   | -   | -   | -   | -     | -      | -   | -   |
|    | 4  | Neg | Y | Neg | Neg | Neg | Neg | 6.5 | Neg | 1.03  | Cloudy | 0.2 | Neg |
|    | 18 | Neg | Y | Neg | Neg | Neg | Neg | 6.5 | Neg | 1.03  | Cloudy | 0.2 | Neg |
|    | 22 | -   | - | -   | -   | -   | -   | -   | -   | -     | -      | -   | -   |
| 43 | 0  | Neg | Y | Neg | Neg | Neg | Neg | 5.5 | Neg | 1.029 | Clear  | 0.2 | Neg |
|    | 4  | Neg | Y | Neg | Neg | Neg | Neg | 6   | Neg | 1.021 | Clear  | 0.2 | Neg |
|    | 18 | -   | - | -   | -   | -   | -   | -   | -   | -     | -      | -   | -   |
|    | 22 | -   | - | -   | -   | -   | -   | -   | -   | -     | -      | -   | -   |

Fig. 9 (Continued)

| | | | | | | | | SULFORAPHANE TREATED | | | | |
|---|---|---|---|---|---|---|---|---|---|---|---|---|
| 1 | 0 | Neg | Y | Neg | Neg | Neg | Neg | 6 | Neg | 1.016 | Clear | 0.2 | Neg |
| | 4 | Neg | Y | Neg | Neg | Neg | Neg | 7.5 | Neg | 1.008 | Clear | 0.2 | Neg |
| | 18 | Neg | Y | Neg | Neg | Neg | Neg | 6 | Neg | 1.017 | Clear | 0.2 | Neg |
| | 22 | Neg | Y | Neg | Neg | Neg | Neg | 7 | Neg | 1.012 | Clear | 0.2 | Neg |
| 3 | 0 | Neg | Y | Neg | Neg | Neg | Neg | 7.5 | Trace | 1.03 | Clear | 0.2 | Neg |
| | 4 | Neg | Y | Neg | Neg | Neg | Neg | 6.5 | Neg | 1.02 | Clear | 0.2 | Neg |
| | 18 | Neg | Y | Neg | Neg | Neg | Neg | 7.5 | Neg | 1.015 | Clear | 0.2 | Neg |
| | 22 | - | - | - | - | - | - | - | - | - | - | - | - |
| 4 | 0 | Neg | Y | Neg | Neg | Neg | Neg | 7.5 | Neg | 1.015 | Clear | 0.2 | Neg |
| | 4 | Neg | Y | Neg | Neg | Neg | Neg | 7 | Neg | 1.01 | Clear | 0.2 | Neg |
| | 18 | Neg | Y | Neg | Neg | Neg | Neg | 8.5 | Neg | 1.011 | Cloudy | 0.2 | Neg |
| | 22 | Neg | Y | Neg | Neg | Neg | Neg | 8 | Neg | 1.003 | Cloudy | 0.2 | Neg |
| 7 | 0 | Neg | Y | Neg | Neg | Neg | Neg | 8 | Neg | 1.021 | Cloudy | 0.2 | Neg |
| | 4 | Neg | Y | Neg | Neg | Neg | Neg | 7 | Neg | 1.01 | Clear | 0.2 | Neg |
| | 18 | Neg | Y | Neg | Neg | Neg | Neg | 8 | Neg | 1.011 | Cloudy | 0.2 | Neg |
| | 22 | Neg | Y | Neg | Neg | Neg | Neg | 7.5 | Neg | 1.012 | Cloudy | 0.2 | Neg |
| 8 | 0 | Neg | Y | Neg | Neg | Neg | Neg | 7 | Neg | 1.019 | Cloudy | 0.2 | Neg |
| | 4 | Neg | Y | Neg | Neg | Neg | Neg | 8.5 | Neg | 1.009 | Cloudy | 0.2 | Neg |
| | 18 | Neg | Y | Neg | Neg | Neg | Neg | 8.2 | Neg | 1.01 | Clear | 0.2 | Neg |
| | 22 | Neg | Y | Neg | Neg | Neg | Neg | 8.2 | Neg | 1.01 | Clear | 0.2 | Neg |
| 10 | 0 | - | - | - | - | - | - | - | - | - | - | - | - |
| | 4 | Neg | Y | Neg | Neg | Neg | Neg | 7 | Neg | 1.009 | Clear | 0.2 | Neg |
| | 18 | Neg | Y | Neg | Neg | Neg | Neg | 7.5 | Neg | 1.024 | Cloudy | 0.2 | Neg |
| | 22 | Neg | Y | Neg | Neg | Neg | Neg | 7.2 | Neg | 1.02 | Cloudy | 0.2 | Neg |
| 11 | 0 | Neg | Y | Neg | Neg | Neg | Neg | 6.5 | Neg | 1.016 | Clear | 0.2 | Neg |
| | 4 | Neg | Y | Neg | Neg | Neg | Neg | 6.9 | Neg | 1.01 | Clear | 0.2 | Neg |
| | 18 | Neg | Y | Neg | Neg | Neg | Neg | 5.5 | Neg | 1.022 | Clear | 0.2 | Neg |
| | 22 | - | - | - | - | - | - | - | - | - | - | - | - |

Fig. 9 (Continued)

| | | | | | | | | | | | | |
|---|---|---|---|---|---|---|---|---|---|---|---|---|
| 12 | 0 | Neg | Y | Neg | Neg | Neg | Neg | 7.1 | Neg | 1.009 | Clear | 0.2 | Neg |
| | 4 | Neg | Y | Neg | Neg | Neg | Neg | 7 | Neg | 1.021 | Clear | 0.2 | Neg |
| | 18 | Neg | Y | Neg | Neg | Neg | Neg | 8 | Neg | 1.022 | Cloudy | 0.2 | Neg |
| | 22 | - | - | - | - | - | - | - | - | - | - | - | - |
| 13 | 0 | - | - | - | - | - | - | - | - | - | - | - | - |
| | 4 | Neg | Y | Neg | Neg | Neg | Neg | 6 | Neg | 1.009 | Clear | 1 | Neg |
| | 18 | Neg | Y | Neg | Neg | Neg | Neg | 6 | Neg | 1.009 | Clear | 1 | Neg |
| | 22 | - | - | - | - | - | - | - | - | - | - | - | - |
| 15 | 0 | Neg | Y | Neg | Neg | Neg | Neg | 6 | Neg | 1.016 | Clear | 0.2 | Neg |
| | 4 | Neg | Y | Neg | Neg | Neg | Neg | 8 | Neg | 1.022 | Clear | 1 | Neg |
| | 18 | Neg | Y | Neg | Neg | Neg | Neg | 7.7 | Neg | 1.009 | Clear | 1 | Neg |
| | 22 | - | - | - | - | - | - | - | - | - | - | - | - |
| 16 | 0 | Neg | Y | Neg | Neg | Neg | Neg | 7.5 | Neg | 1.02 | Clear | 0.2 | Neg |
| | 4 | Neg | Y | Neg | Neg | Neg | Neg | 7.5 | Neg | 1.011 | Clear | 0.2 | Neg |
| | 18 | - | - | - | - | - | - | - | - | - | - | - | - |
| | 22 | Neg | Y | Neg | Neg | Neg | Neg | 7.2 | Neg | 1.02 | Clear | 0.2 | Neg |
| 17 | 0 | Neg | Y | Neg | Neg | Neg | Neg | 6 | Neg | 1.013 | Clear | 0.2 | Neg |
| | 4 | Neg | Y | Neg | Neg | Neg | Neg | 7.5 | Neg | 1.011 | Clear | 0.2 | Neg |
| | 18 | Neg | Y | Neg | Neg | Neg | Neg | 7 | Neg | 1.013 | Clear | 0.2 | Neg |
| | 22 | Neg | Y | Neg | Neg | Neg | Neg | 7.5 | Neg | 1.011 | Clear | 0.2 | Neg |
| 21 | 0 | Neg | Y | Neg | Neg | Neg | Neg | 7.5 | TRACE | 1.028 | Clear | 1 | Neg |
| | 4 | Neg | Y | Neg | Neg | Neg | Neg | 6.5 | Neg | 1.03 | Clear | 1 | Neg |
| | 18 | Neg | Y | Neg | Neg | Neg | Neg | 7.7 | Neg | 1.01 | Clear | 1 | Neg |
| | 22 | Neg | Y | Neg | Neg | Neg | Neg | 7.5 | Neg | 1.026 | Clear | 1 | Neg |
| 23 | 0 | Neg | Y | Neg | Neg | Neg | Neg | 5.5 | Neg | 1.009 | Clear | 0.2 | Neg |
| | 4 | Neg | Y | Neg | Neg | Neg | Neg | 6 | Neg | 1.016 | Clear | 0.2 | Neg |
| | 18 | Neg | Y | Neg | Neg | Neg | Neg | 7.5 | Neg | 1.007 | Clear | 1 | Neg |
| | 22 | Neg | Y | Neg | Neg | Neg | Neg | 7.5 | Neg | 1.007 | Clear | 1 | Neg |

Fig. 9 (Continued)

| | | | | | | | | | | | | |
|---|---|---|---|---|---|---|---|---|---|---|---|---|
| 25 | 0 | Neg | Y | Neg | Neg | Neg | Neg | 8 | Neg | 1.01 | Clear | 0.2 | Neg |
| | 4 | Neg | Y | Neg | Neg | Neg | Neg | 8.5 | trace | 1.013 | Clear | 0.2 | Neg |
| | 18 | Neg | Y | Neg | Neg | Neg | Neg | 8 | Neg | 1.025 | Cloudy | 1 | Neg |
| | 22 | - | - | - | - | - | - | - | - | - | - | - | - |
| 27 | 0 | Neg | Y | Neg | Neg | Neg | Neg | 7 | Neg | 1.025 | Clear | 0.2 | Neg |
| | 4 | Neg | Y | Neg | Neg | Neg | Neg | 7 | Neg | 1.01 | Clear | 0.2 | Neg |
| | 18 | Neg | Y | Neg | Neg | Neg | Neg | 7.5 | Neg | 1.02 | Clear | 0.2 | Neg |
| | 22 | Neg | Y | Neg | Neg | Neg | Neg | 7.5 | Neg | 1.025 | Clear | 0.2 | Neg |
| 28 | 0 | - | - | - | - | - | - | - | - | - | - | - | - |
| | 4 | Neg | Y | Neg | Neg | Neg | Neg | 7 | Neg | 1.024 | Clear | 0.2 | Neg |
| | 18 | Neg | Y | Neg | Neg | Neg | Neg | 7 | Neg | 1.024 | Clear | 0.2 | Neg |
| | 22 | - | - | - | - | - | - | - | - | - | - | - | - |
| 30 | 0 | Neg | Y | Neg | Neg | Neg | Neg | 6 | Neg | 1.025 | Clear | 0.2 | Neg |
| | 4 | Neg | Y | Neg | Neg | Neg | Neg | 6 | Neg | 1.026 | Clear | 0.2 | Neg |
| | 18 | Neg | Y | Neg | Neg | Neg | Neg | 6.5 | Neg | 1.022 | Clear | 0.2 | Neg |
| | 22 | - | - | - | - | - | - | - | - | - | - | - | - |
| 31 | 0 | Neg | Y | Neg | Neg | Neg | Neg | 8 | Neg | 1.025 | Clear | 1 | Neg |
| | 4 | Neg | Y | Neg | Neg | Neg | Neg | 8.5 | Neg | 1.017 | Clear | 0.2 | Neg |
| | 18 | Neg | Y | Neg | Neg | Neg | Neg | 7.5 | Neg | 1.014 | Clear | 1 | Neg |
| | 22 | Neg | Y | Neg | Neg | Neg | Neg | 8 | Neg | 1.025 | Clear | 1 | Neg |
| 32 | 0 | . | . | . | . | . | . | . | . | . | . | . | . |
| | 4 | . | . | . | . | . | . | . | . | . | . | . | . |
| | 18 | . | . | . | . | . | . | . | . | . | . | . | . |
| | 22 | . | . | . | . | . | . | . | . | . | . | . | . |
| 35 | 0 | - | - | - | - | - | - | - | - | - | - | - | - |
| | 4 | Neg | Y | Neg | Neg | Neg | Neg | 7 | Neg | 1.014 | Cloudy | Neg | Neg |
| | 18 | Neg | Y | Neg | Neg | Neg | Neg | 7 | Neg | 1.026 | Cloudy | 1 | Neg |
| | 22 | Neg | Y | Neg | Neg | Neg | Neg | 7.5 | Neg | 1.014 | Cloudy | 0.2 | Neg |

Fig. 9 (Continued)

| | | | | | | | | | | | | |
|---|---|---|---|---|---|---|---|---|---|---|---|---|
| 37 | 0 | Neg | Y | Neg | Neg | Neg | Neg | 7.5 | Neg | 1.008 | Clear | 0.2 | Neg |
| | 4 | Neg | Y | Neg | Neg | Neg | Neg | 8 | Neg | 1.017 | Clear | 0.2 | Neg |
| | 18 | Neg | Y | Neg | Neg | Neg | Neg | 7.5 | Neg | 1.02 | Clear | 0.2 | Neg |
| | 22 | Neg | Y | Neg | Neg | Neg | Neg | 8 | Neg | 1.011 | Cloudy | 0.2 | Neg |
| 38 | 0 | Neg | Y | Neg | Trace | Neg | Neg | 8 | Neg | 1.027 | Cloudy | 1 | Neg |
| | 4 | Neg | Y | Neg | Neg | Neg | Neg | 8 | Neg | 1.024 | Clear | 0.2 | Neg |
| | 18 | Neg | Y | Neg | Neg | Neg | Neg | 7.5 | Neg | 1.005 | Clear | 0.2 | Neg |
| | 22 | Neg | Y | Neg | Neg | Neg | Neg | 7.5 | Neg | 1.025 | Clear | 0.2 | Neg |
| 40 | 0 | Neg | Y | Neg | Neg | Neg | Neg | 8 | Neg | 1.017 | Clear | 0.2 | Neg |
| | 4 | Neg | Y | Neg | Neg | Neg | Neg | 7.5 | Neg | 1.024 | Clear | 1 | Neg |
| | 18 | Neg | Y | Neg | Neg | Neg | Neg | 6 | Neg | 1.025 | Clear | 1 | Neg |
| | 22 | - | - | - | - | - | - | - | - | - | - | - | - |
| 42 | 0 | Neg | Y | Neg | Neg | Neg | Neg | 6.5 | Neg | 1.03 | Cloudy | 0.2 | Neg |
| | 4 | Neg | Y | Neg | Trace | Neg | Neg | 8 | Neg | 1.028 | Clear | 1 | Neg |
| | 18 | Neg | Y | Trace | Trace | Neg | Neg | 7 | Neg | 1.026 | Clear | 1 | Neg |
| | 22 | Neg | Y | Neg | Trace | Neg | Neg | 5.5 | Neg | 1.029 | Clear | 1 | Neg |
| 44 | 0 | Neg | Y | Neg | Neg | Neg | Neg | 6 | Neg | 1.027 | Cloudy | 0.2 | Neg |
| | 4 | Neg | Y | Neg | Neg | Neg | Neg | 5.5 | Neg | 1.025 | Clear | 0.2 | Neg |
| | 18 | Neg | Y | Neg | Neg | Neg | Neg | 6.5 | Neg | 1.007 | Clear | 0.2 | Neg |
| | 22 | - | - | - | - | - | - | - | - | - | - | - | - |

Fig. 9 (Continued)

| Subject ID | Week | CHEMISTRY | | | | | | | | | | | | | | | | | |
|---|---|---|---|---|---|---|---|---|---|---|---|---|---|---|---|---|---|---|---|
| | | Na | K | Cl | CO2 | BUN | Creat | Alb | TP | Ca | AP | Tot Bili | SGOT | SGPT | Glob | eGFR | An Gap | Plas Gluc | TSH |
| | | PLACEBO | | | | | | | | | | | | | | | | | |
| 2 | 0 | 139 | 3.5 | 100 | 25.2 | 13 | 0.87 | 4.6 | 6.6 | 9.3 | 147 | 0.6 | 18 | 15 | 2 | NC* | 11 | 80 | 2.2 |
| | 4 | 141 | 4.1 | 104 | 28 | 13 | 0.8 | 5 | 7.2 | 10.1 | 161 | 0.9 | 21 | 21 | 2.2 | NC | 8 | 79 | 2.2 |
| | 18 | 141 | 3.4 | 100 | 26 | 11 | 0.82 | 4.9 | 7.4 | 9.7 | 153 | 0.6 | 21 | 19 | 2.5 | NC | 15 | 75 | 2.1 |
| | 22 | 139 | 4.4 | 104 | 26 | 12 | 1 | 4.6 | 7.4 | 9.3 | 132 | 1.2 | 19 | 17 | 2.8 | NC | 12 | 1.5 | 1.63 |
| 5 | 0 | 138 | 4.2 | 107 | 23 | 17 | 0.6 | 4.4 | 6.5 | 9.5 | 241 | 0.3 | 25 | 11 | 2.1 | NC | 11 | 96 | 2.2 |
| | 4 | 141 | 4.2 | 108 | 23 | 18 | 0.82 | 4.4 | 7 | 10.2 | 274 | 0.4 | 41 | 17 | 2.6 | NC | 9 | 90 | 2.21 |
| | 18 | 140 | 4 | 104 | 24 | 17 | 0.65 | 4.2 | 6.7 | 10.3 | 229 | 0.3 | 28 | 11 | 2.5 | NC | 12 | 96 | 2.4 |
| | 22 | | | | | | | | | | | | | | | | | | |
| 6 | 0 | 137 | 3.7 | 102 | 28 | 12 | 0.73 | 4.8 | 7.4 | 9.4 | 181 | 0.9 | 20 | 16 | 2.6 | NC | 7 | 82 | 1.71 |
| | 4 | 138 | 3.5 | 101 | 22 | 9 | 0.71 | 4.9 | 7.6 | 9.7 | 183 | 0.8 | 19 | 13 | 2.7 | NC | 9 | 78 | 1.81 |
| | 18 | 142 | 3.4 | 13 | 26 | 9 | 0.77 | 4.4 | 7.2 | 9.6 | 153 | 0.8 | 17 | 15 | 2.8 | NC | 13 | 94 | 1.6 |
| | 22 | | | | | | | | | | | | | | | | | | |
| 9 | 0 | 136 | 3.5 | 104 | 25 | 24 | 1.17 | 5.1 | 8 | 9.4 | 104 | 0.5 | 32 | 21 | 2.9 | >60 | 7 | 94 | 0.85 |
| | 4 | 139 | 3.8 | 101 | 24 | 18 | 0.85 | 5 | 7.5 | 10.3 | 80 | 0.6 | 42 | 35 | 2.5 | >60 | 13 | 76 | 0.91 |
| | 18 | 141 | 3.4 | 103 | 23 | 18 | 0.94 | 4.8 | 7.5 | 9.6 | 84 | 0.3 | 20 | 14 | 2.9 | >60 | 15 | 75 | 0.89 |
| | 22 | 141 | 3.7 | 103 | 28 | 20 | 0.88 | 4.2 | 6.9 | 9.2 | 65 | 0.4 | 22 | 16 | 2.7 | >60 | 10 | 50 | 0.72 |
| 14 | 0 | 146 | 2.9 | 108 | 20 | 12 | 0.85 | 5.1 | 7.6 | 10.7 | 81 | 0.5 | 18 | 22 | 2.5 | >60 | 18 | 59 | 0.94 |
| | 4 | 142 | 3.3 | 108 | 19 | 11 | 0.86 | 4.1 | 7.2 | 9.5 | 89 | 0.3 | 20 | 24 | 3.1 | >60 | 15 | 127 | 1.48 |
| | 18 | 142 | 3.1 | 105 | 22 | 7 | 0.82 | 4.1 | 6.9 | 9.5 | 83 | 0.6 | 15 | 22 | 2.8 | >60 | 15 | 107 | 1.56 |
| | 22 | 140 | 3.8 | 110 | 22 | 13 | 0.83 | 4.3 | 7.3 | 9.6 | 79 | 0.5 | 23 | 28 | 3 | >60 | 8 | 59 | 1.28 |
| 18 | 0 | 136 | 3.3 | 102 | 21 | 12 | 0.78 | 4.6 | 6.6 | 9.3 | 120 | 0.3 | 14 | 19 | 1.8 | >60 | 13 | 118 | 0.78 |
| | 4 | 137 | 3.2 | 104 | 19 | 15 | 0.87 | 4.4 | 7.2 | 9.5 | 105 | 0.3 | 17 | 21 | 2.8 | >60 | 14 | 125 | 0.89 |
| | 18 | 137 | 3.4 | 104 | 22 | 12 | 0.87 | 4.5 | 7.3 | 9.6 | 103 | 0.3 | 17 | 15 | 2.8 | >60 | 11 | 108 | 0.95 |
| | 22 | 141 | 4 | 105 | 24 | 17 | 0.84 | 4.4 | 7.6 | 9.9 | 98 | 0.2 | 19 | 17 | 3.2 | >60 | 12 | 100 | 0.65 |

Fig. 9 (Continued)

| | | | | | | | | | | | | | | | | | | | |
|---|---|---|---|---|---|---|---|---|---|---|---|---|---|---|---|---|---|---|---|
| 19 | 0 | 139 | 3.4 | 105 | 22 | 17 | 0.69 | 4.7 | 7.5 | 9.4 | 118 | 0.5 | 28 | 16 | 2.8 | >60 | 12 | 85 | 3.25 |
| | 4 | 139 | 3.4 | 105 | 22 | 17 | 0.69 | 4.7 | 7.5 | 9.4 | 118 | 0.5 | 28 | 16 | 2.8 | >61 | 12 | 85 | 3.25 |
| | 18 | 141 | 3.6 | 110 | 21 | 15 | 0.75 | 4.3 | 7.4 | 9.2 | 111 | 0.5 | 27 | 18 | 3.1 | >60 | 10 | 104 | 1.28 |
| | 22 | 141 | 3.3 | 105 | 21 | 20 | 0.79 | 4.3 | 7.9 | 9.2 | 119 | 0.5 | 29 | 19 | 3.6 | >60 | 15 | 84 | 2.02 |
| 24 | 0 | 138 | 3.6 | 101 | 23 | 17 | 0.77 | 4.4 | 7.6 | 9.6 | 241 | 0.7 | 28 | 12 | 3.2 | NC | 11 | 85 | 1.56 |
| | 4 | 139 | 4.1 | 104 | 25 | 16 | 0.72 | 4.3 | 7.6 | 9.3 | 194 | 0.5 | 28 | 15 | 3.3 | NC | 9 | 87 | 1.72 |
| | 18 | 139 | 3.8 | 105 | 25 | 15 | 0.74 | 4.2 | 7.4 | 9.3 | 194 | 0.6 | 28 | 13 | 3.2 | NC | 9 | 84 | 1.53 |
| | 22 | | | | | | | | | | | | | | | | | | |
| 29 | 0 | 137 | 3.6 | 0.5 | 23 | 6 | 0.86 | 4.7 | 8.2 | 9.8 | 103 | 0.6 | 29 | 35 | 3.5 | >60 | 9 | 68 | 2.77 |
| | 4 | 140 | 3.5 | 106 | 22 | 9 | 0.82 | 4.3 | 7.4 | 9.4 | 94 | 0.6 | 27 | 43 | 3.1 | >60 | 12 | 89 | 2.28 |
| | 18 | 139 | 3.3 | 103 | 25 | 8 | 0.77 | 4.4 | 7.6 | 10 | 82 | 0.7 | 26 | 45 | 3.2 | >60 | 11 | 78 | 2.08 |
| | 22 | 138 | 3.6 | 103 | 19 | 10 | 0.78 | 4.5 | 7.7 | 9.7 | 88 | 1 | 26 | 44 | 3.2 | >60 | 16 | 80 | 1.86 |
| 33 | 0 | 139 | 3.7 | 101 | 24 | 11 | 0.81 | 4.1 | 6.6 | 9.6 | 145 | 0.9 | 19 | 14 | 2.5 | NC | 5 | 78 | 1.47 |
| | 4 | 140 | 3.8 | 104 | 25 | 14 | 0.82 | 4.4 | 7.3 | 9.7 | 192 | 1.8 | 21 | 16 | 2.9 | NC | 11 | 84 | 0.98 |
| | 18 | 138 | 4.2 | 103 | 23 | 11 | 0.79 | 4.3 | 6.8 | 9.6 | 197 | 1.6 | 17 | 9 | 2.5 | NC | 12 | 78 | 1.11 |
| | 22 | 139 | 3.8 | 102 | 26 | 13 | 0.79 | 4.4 | 7 | 9.8 | 179 | 1.7 | 19 | 12 | 2.6 | NC | 11 | 79 | 1.01 |
| 34 | 0 | 143 | 3.8 | 109 | 24 | 6 | 0.74 | 4.3 | 7 | 9.4 | 86 | 0.8 | 15 | 17 | 2.7 | NC | 10 | 100 | 0.36 |
| | 4 | 143 | 4.2 | 106 | 25 | 9 | 0.78 | 4.4 | 7.3 | 9.8 | 90 | 0.7 | 19 | 18 | 2.9 | NC | 12 | 104 | 0.69 |
| | 18 | 140 | 4.3 | 106 | 27 | 8 | 0.77 | 4.3 | 6.9 | 9.6 | 87 | 0.5 | 15 | 11 | 2.8 | >60 | 7 | 86 | 0.34 |
| | 22 | 140 | 4.2 | 102 | 27 | 7 | 0.77 | 4.5 | 7.5 | 10.2 | 95 | 1.3 | 17 | 16 | 3 | >60 | 11 | 86 | 0.57 |
| 36 | 0 | 142 | 5 | 105 | 24 | 20 | 0.66 | 4.3 | 7.6 | 10.5 | 251 | 0.5 | 34 | 19 | 3.3 | NC | 13 | 86 | 0.53 |
| | 4 | 142 | 4.2 | 104 | 24 | 18 | 0.69 | 4.6 | 7.6 | 10.5 | 240 | 0.4 | 34 | 17 | 3 | NC | 14 | 82 | 0.83 |
| | 18 | 141 | 3.9 | 102 | 22 | 12 | 0.67 | 4.6 | 7.4 | 10.2 | 195 | 0.5 | 25 | 15 | 2.6 | | 17 | 89 | 0.97 |
| | 22 | | | | | | | | | | | | | | | | | | |
| 41 | 0 | | | | | | | | | | | | | | | | | | |
| | 4 | 139 | 3.6 | 102 | 24 | 12 | 0.59 | 4.5 | 8.1 | 10 | 125 | 0.5 | 45 | 76 | 3.6 | NC | 13 | 103 | 4.17 |
| | 18 | 137 | 3.6 | 102 | 21 | 16 | 0.62 | 4.3 | 7.9 | 9.9 | 109 | 0.4 | 50 | 82 | 3.6 | NC | 14 | 110 | 2.44 |
| | 22 | | | | | | | | | | | | | | | | | | |
| 43 | 0 | 144 | 4.4 | 107 | 22 | 16 | 0.72 | 4.5 | 7.5 | 10.1 | 535 | 0.5 | 28 | 21 | 3 | NC | 15 | 82 | 2.36 |
| | 4 | 140 | 4.6 | 104 | 22 | 13 | 0.71 | 4.4 | 7.3 | 10.5 | 498 | 0.6 | 26 | 21 | 2.9 | NC | 14 | 85 | 2.48 |
| | 18 | | | | | | | | | | | | | | | | | | |
| | 22 | | | | | | | | | | | | | | | | | | |

Fig. 9 (Continued)

| | | | | | | | SULFORAPHANE TREATED | | | | | | | | | | | |
|---|---|---|---|---|---|---|---|---|---|---|---|---|---|---|---|---|---|---|
| 1 | 0 | 139 | 3.6 | 112 | 17 | 12 | 0.82 | 4.9 | 7.6 | 9.5 | 7.5 | 0.2 | 25 | 58 | 2.7 | >50 | 10 | 100 | 0.81 |
| | 4 | 135 | 4.1 | 106 | 17 | 16 | 0.95 | 4.8 | 7.9 | 9.2 | 84 | 0.2 | 39 | 76 | 3.1 | >50 | 10 | 95 | 0.95 |
| | 18 | 139 | 3.4 | 108 | 16 | 13 | 0.95 | 4.9 | 8.2 | 9.7 | 79 | 0.3 | 25 | 51 | 3.3 | >50 | 15 | 103 | 1.08 |
| | 22 | 141 | 3.4 | 110 | 18 | 13 | 0.99 | 4.3 | 7.4 | 9.6 | 79 | 0.2 | 24 | 46 | 3.1 | >50 | 13 | 89 | 1.02 |
| 3 | 0 | 142 | 4.4 | 105 | 25 | 14 | 0.88 | 4.9 | 7.9 | 9.3 | 237 | 0.4 | 23 | 14 | 3.1 | NC | 9 | 101 | 1.24 |
| | 4 | | | | | | | | | | | | | | | | | | |
| | 18 | 140 | 3.7 | 102 | 26 | 10 | 0.76 | 4.8 | 7.5 | 9.9 | 235 | 0.3 | 18 | 11 | 2.7 | NC | 13 | 92 | 1.94 |
| | 22 | 139 | 4.1 | 101 | 24 | 14 | 0.73 | 4.5 | 7.4 | 9.6 | 227 | 0.4 | 17 | 8 | 2.9 | NC | 14 | 79 | 1.57 |
| 4 | 0 | 142 | 3.9 | 106 | 19 | 8 | 0.79 | 5.1 | 8.2 | 10.4 | 75 | 0.3 | 19 | 30 | 3.1 | >50 | 17 | 79 | 1.59 |
| | 4 | 136 | 3.7 | 104 | 24 | 9 | 0.7 | 4.9 | 7.6 | 9.8 | 45 | 0.4 | 19 | 31 | 2.7 | >50 | 8 | 82 | 1.76 |
| | 18 | 138 | 3.5 | 101 | 27 | 6 | 0.76 | 4.2 | 7.4 | 9.8 | 73 | 0.3 | 18 | 34 | 3.2 | >50 | 10 | 73 | 1.95 |
| | 22 | 138 | 6.5 | 101 | 24 | 8 | 0.75 | 4.6 | 8.1 | 9.8 | 80 | 0.3 | 20 | 30 | 3.5 | >50 | 13 | 133 | 2.1 |
| 7 | 0 | 135 | 3.6 | 102 | 22 | 11 | 0.82 | 5.2 | 8.1 | 10.1 | 114 | 1.4 | 23 | 31 | 2.9 | NC | 11 | 101 | 2.55 |
| | 4 | 140 | 3.6 | 101 | 26 | 9 | 0.82 | 5 | 7.8 | 10.2 | 114 | 1.5 | 25 | 36 | 2.8 | NC | 13 | 92 | 1.58 |
| | 18 | 139 | 3.4 | 102 | 27 | 8 | 0.9 | 4.7 | 7.7 | 10.4 | 109 | 1.4 | 22 | 30 | 3 | NC | 10 | 84 | 2.51 |
| | 22 | 138 | 3.3 | 102 | 23 | 11 | 0.84 | 4.8 | 7.5 | 9.9 | 111 | 1.4 | 24 | 34 | 2.9 | NC | 13 | 113 | 1.19 |
| 8 | 0 | 140 | 3.5 | 106 | 21 | 16 | 1.1 | 5 | 7.3 | 9.7 | 134 | 0.4 | 28 | 25 | 2.3 | >50 | 13 | 89 | 1.93 |
| | 4 | 139 | 3.4 | 103 | 21 | 16 | 0.87 | 5 | 7.2 | 9.7 | 137 | 0.3 | 31 | 29 | 2.2 | >50 | 14 | 94 | 2.5 |
| | 18 | 137 | 3.5 | 1.2 | 24 | 14 | 1.11 | 4.7 | 7.1 | 9.8 | 125 | 0.4 | 27 | 22 | 2.4 | >50 | 11 | 86 | 1.92 |
| | 22 | 141 | 3.9 | 107 | 22 | 18 | 0.86 | 4.5 | 7.2 | 9.6 | 136 | 0.3 | 26 | 27 | 2.7 | >50 | 12 | 90 | 1.6 |
| 10 | 0 | | | | | | | | | | | | | | | | | | |
| | 4 | 141 | 3.3 | 106 | 20 | 14 | 0.88 | 4.4 | 6.6 | 9.5 | 322 | 0.3 | 28 | 25 | 2.2 | NC | 15 | 84 | 1.24 |
| | 18 | 139 | 3.2 | 105 | 24 | 11 | 0.85 | 4 | 7.1 | 9.1 | 255 | 0.5 | 25 | 17 | 3.1 | NC | 10 | 69 | 1.33 |
| | 22 | 140 | 4.5 | 105 | 26 | 17 | 0.85 | 4.1 | 7.4 | 9.2 | 276 | 0.4 | 27 | 28 | 3 | NC | 8 | 65 | 1.55 |
| 11 | 0 | 139 | 3.8 | 106 | 17 | 11 | 0.59 | 5 | 7.7 | 10.3 | 182 | 0.4 | 22 | 15 | 2.7 | NC | 16 | 98 | 1.96 |
| | 4 | 141 | 3.4 | 106 | 24 | 9 | 0.52 | 4.7 | 6.6 | 9.8 | 209 | 0.4 | 20 | 13 | 2.1 | NC | 12 | 86 | 3.37 |
| | 18 | 139 | 4 | 105 | 23 | 10 | 0.6 | 4.4 | 7.4 | 9.9 | 164 | 0.6 | 20 | 12 | 3 | NC | 11 | 93 | 2.95 |
| | 22 | 140 | 5.1 | 107 | 22 | 12 | 0.56 | 4.2 | 7 | 9.9 | 161 | 0.3 | 19 | 14 | 2.8 | NC | 11 | 80 | 2.74 |

Fig. 9 (Continued)

| | | | | | | | | | | | | | | | | | | |
|---|---|---|---|---|---|---|---|---|---|---|---|---|---|---|---|---|---|---|
| 12 | 0 | 140 | 3.7 | 106 | 24 | 17 | 0.75 | 4.7 | 7.2 | 9.7 | 78 | 0.3 | 18 | 16 | 2.5 | >60 | 11 | 79 | 1.82 |
| | 4 | 142 | 3.4 | 104 | 22 | 17 | 0.78 | 4.7 | 7.2 | 9.7 | 79 | 0.4 | 22 | 24 | 2.5 | >60 | 15 | 68 | 2.07 |
| | 18 | 141 | 3.6 | 103 | 25 | 16 | 0.82 | 4.5 | 7.5 | 10 | 78 | 0.8 | 22 | 22 | 3 | >60 | 13 | 78 | 1.97 |
| | 22 | - | - | - | - | - | - | - | - | - | - | - | - | - | - | - | - | - | - |
| 13 | 0 | 139 | 3.7 | 107 | 22 | 19 | 0.78 | 4.6 | 7.1 | 9.6 | 79 | 0.3 | 18 | 20 | 2.5 | >60 | 10 | 86 | 1.7 |
| | 4 | 140 | 3.2 | 101 | 24 | 13 | 0.76 | 4.9 | 7.1 | 9.7 | 81 | 0.4 | 32 | 47 | 2.2 | >60 | 15 | 78 | 2.32 |
| | 18 | 142 | 3.6 | 104 | 23 | 11 | 0.78 | 4.4 | 7.3 | 9.8 | 71 | 0.7 | 20 | 34 | 2.9 | >60 | 15 | 71 | 1.87 |
| | 22 | - | - | - | - | - | - | - | - | - | - | - | - | - | - | - | - | - | - |
| 15 | 0 | 138 | 3.7 | 103 | 25 | 21 | 0.74 | 5.2 | 6.9 | 9.6 | 134 | 0.3 | 16 | 10 | 1.7 | >60 | 10 | 106 | 0.47 |
| | 4 | 140 | 3.9 | 102 | 26 | 19 | 0.84 | 4.4 | 6.9 | 9.5 | 112 | 0.3 | 15 | 11 | 2.5 | >60 | 12 | 83 | 0.32 |
| | 18 | 137 | 3.7 | 101 | 27 | 19 | 0.85 | 4.4 | 7 | 9.1 | 119 | 0.2 | 16 | 13 | 2.6 | >60 | 9 | 90 | 0.82 |
| | 22 | 140 | 4.2 | 102 | 29 | 17 | 0.85 | 4.3 | 6.9 | 9.2 | 115 | 0.3 | 16 | 13 | 2.6 | >60 | 9 | 74 | 0.69 |
| 16 | 0 | 141 | 3.5 | 108 | 18 | 11 | 0.55 | 5.1 | 8 | 9.6 | 124 | 0.5 | 22 | 44 | 2.9 | >60 | 15 | 76 | 1.01 |
| | 4 | 139 | 3.7 | 108 | 19 | 10 | 0.75 | 4.5 | 7.5 | 9.5 | 115 | 0.5 | 24 | 49 | 3 | >60 | 12 | 79 | 1.87 |
| | 18 | - | - | - | - | - | - | - | - | - | - | - | - | - | - | - | - | - | - |
| | 22 | 141 | 3.5 | 108 | 22 | 14 | 0.71 | 4.8 | 7.8 | 9.9 | 122 | 0.5 | 25 | 67 | 3 | >60 | 10 | 87 | 1.42 |
| 17 | 0 | 144 | 3.3 | 104 | 25 | 12 | 0.73 | 4.2 | 6.1 | 8.6 | 111 | 0.5 | 16 | 38 | 1.9 | >60 | 15 | 79 | 0.89 |
| | 4 | 141 | 3.6 | 108 | 22 | 12 | 0.79 | 3.9 | 5.9 | 8.5 | 99 | 0.5 | 21 | 48 | 2.1 | >60 | 10 | 90 | 1.4 |
| | 18 | 142 | 3.9 | 107 | 23 | 10 | 0.83 | 4.1 | 6.3 | 8.5 | 104 | 0.6 | 31 | 66 | 2.2 | >60 | 12 | 83 | 1.97 |
| | 22 | 138 | 3.4 | 108 | 22 | 17 | 0.79 | 4.2 | 6.3 | 9 | 104 | 0.5 | 26 | 70 | 2.1 | >60 | 8 | 75 | 1.42 |
| 21 | 0 | 140 | 3.9 | 106 | 18 | 14 | 0.71 | 4.7 | 7.1 | 9.5 | 204 | 0.4 | 21 | 17 | 2.4 | NC | 16 | 91 | 1.4 |
| | 4 | 141 | 3.5 | 107 | 21 | 19 | 0.73 | 4.2 | 6.9 | 9.3 | 173 | 0.3 | 19 | 17 | 2.7 | NC | 13 | 102 | 1.09 |
| | 18 | 141 | 3.7 | 109 | 23 | 17 | 0.81 | 4.2 | 6.8 | 9.3 | 151 | 0.4 | 22 | 23 | 2.6 | NC | 9 | 128 | 0.83 |
| | 22 | 140 | 4.1 | 107 | 20 | 17 | 0.71 | 4.3 | 7.2 | 9.7 | 131 | 5 | 22 | 22 | 2.9 | NC | 13 | 87 | 0.97 |
| 23 | 0 | 136 | 3.6 | 104 | 20 | 11 | 0.78 | 4.2 | 7.3 | 9.3 | 69 | 1 | 27 | 47 | 3.1 | >60 | 12 | 96 | 1.7 |
| | 4 | 140 | 3.5 | 108 | 17 | 7 | 0.74 | 4.1 | 7.4 | 9.2 | 62 | 1.1 | 15 | 22 | 3.3 | >60 | 15 | 84 | 1.05 |
| | 18 | 138 | 3.9 | 103 | 25 | 11 | 0.82 | 4.3 | 7.8 | 9.4 | 67 | 1.1 | 17 | 25 | 3.5 | >60 | 10 | 75 | 1.8 |
| | 22 | 142 | 3.7 | 106 | 24 | 9 | 0.78 | 4 | 7.7 | 9.4 | 71 | 0.9 | 26 | 45 | 3.7 | >60 | 12 | 88 | 1.52 |
| 25 | 0 | 142 | 3.5 | 105 | 20 | 12 | 0.87 | 4.8 | 7.9 | 10 | 46 | 0.7 | 11 | 7 | 3.1 | NC | 14 | 85 | 1.81 |
| | 4 | 141 | 3.7 | 106 | 24 | 15 | 0.75 | 4.8 | 7.7 | 10 | 71 | 0.4 | 13 | 9 | 2.9 | >60 | 11 | 77 | 1.49 |
| | 18 | 140 | 3.5 | 105 | 22 | 17 | 0.83 | 4.8 | 7.7 | 10 | 67 | 0.5 | 13 | 8 | 2.9 | >60 | 13 | 90 | 2.46 |
| | 22 | - | - | - | - | - | - | - | - | - | - | - | - | - | - | - | - | - | - |

Fig. 9 (Continued)

| | | | | | | | | | | | | | | | | | |
|---|---|---|---|---|---|---|---|---|---|---|---|---|---|---|---|---|---|
| 27 | 0 | 142 | 4 | 104 | 24 | 14 | 0.86 | 4.7 | 7.5 | 9.9 | 86 | 0.3 | 19 | 17 | 2.8 | >60 | 14 | 81 | 2.12 |
| | 4 | 147 | 4.5 | 105 | 30 | 19 | 0.94 | 4.7 | 7.6 | 10.1 | 88 | 0.3 | 21 | 38 | 2.9 | >60 | 12 | 87 | 1.77 |
| | 18 | 146 | 4.8 | 104 | 28 | 13 | 0.97 | 4.8 | 7.9 | 10.5 | 93 | 0.4 | 19 | 24 | 3.1 | >60 | 14 | 90 | 1.98 |
| | 22 | 143 | 4.1 | 102 | 27 | 17 | 0.9 | 4.7 | 7.6 | 10.2 | 89 | 0.4 | 19 | 19 | 2.9 | >60 | 14 | 90 | 2.07 |
| 28 | 0 | 139 | 3.9 | 104 | 23 | 12 | 0.99 | 4.4 | 7.7 | 9.6 | 95 | 0.8 | 22 | 31 | 3.3 | >60 | 12 | 110 | 1.99 |
| | 4 | 141 | 3.4 | 103 | 26 | 12 | 0.88 | 4.6 | 8.4 | 9.8 | 111 | 0.8 | 29 | 56 | 3.5 | >60 | 10 | 94 | 2.04 |
| | 18 | 139 | 3.8 | 104 | 22 | 13 | 0.89 | 4.1 | 7.3 | 9.2 | 91 | 0.6 | 29 | 46 | 3.2 | >60 | 13 | 103 | 1.57 |
| | 22 | - | - | - | - | - | - | - | - | - | - | - | - | - | - | - | - | - | - |
| 30 | 0 | 140 | 3.7 | 104 | 25 | 11 | 0.88 | 4.5 | 7.5 | 10.2 | 110 | 0.2 | 23 | 30 | 3 | >60 | 10 | 102 | 2.1 |
| | 4 | 139 | 3.4 | 104 | 24 | 16 | 0.87 | 4.3 | 7.3 | 10.3 | 96 | 0.3 | 22 | 35 | 3 | >60 | 11 | 87 | 2.03 |
| | 18 | 140 | 4 | 104 | 26 | 12 | 0.78 | 4.2 | 7.1 | 10.1 | 78 | 0.3 | 24 | 30 | 2.9 | >60 | 10 | 83 | 2.43 |
| | 22 | - | - | - | - | - | - | - | - | - | - | - | - | - | - | - | - | - | - |
| 31 | 0 | 140 | 4.1 | 107 | 24 | 13 | 0.73 | 4.5 | 7.3 | 9.7 | 207 | 0.3 | 16 | 10 | 2.8 | NC | 9 | 93 | 1.46 |
| | 4 | 141 | 4.1 | 105 | 26 | 11 | 0.74 | 4.1 | 7 | 9.2 | 234 | 0.3 | 19 | 11 | 2.9 | NC | 11 | 84 | 2.25 |
| | 18 | 139 | 4.4 | 103 | 27 | 10 | 0.82 | 4.4 | 7.3 | 9.7 | 209 | 0.5 | 19 | 12 | 2.9 | NC | 9 | 106 | 1.79 |
| | 22 | 1.8 | 4.5 | 102 | 25 | 17 | 0.78 | 4.5 | 8 | 10.1 | 14 | 0.5 | 15 | 10 | 3.5 | NC | 11 | 80 | 1.7 |
| 32 | 0 | 143 | 4.7 | 103 | 27 | 11 | 0.76 | 4.8 | 7.4 | 10.4 | 101 | 0.5 | 16 | 11 | 2.5 | NC | 13 | 82 | 3.24 |
| | 4 | 143 | 3.8 | 106 | 23 | 20 | 0.9 | 4.9 | 7.5 | 10.3 | 108 | 0.6 | 19 | 10 | 2.6 | NC | 14 | 89 | 2.9 |
| | 18 | 140 | 4 | 103 | 25 | 14 | 0.77 | 4.8 | 4.6 | 10.5 | 96 | 0.7 | 16 | 12 | 2.8 | NC | 12 | 112 | 1.51 |
| | 22 | - | - | - | - | - | - | - | - | - | - | - | - | - | - | - | - | - | - |
| 35 | 0 | 139 | 3.7 | 105 | 26 | 11 | 0.97 | 4.7 | 8.1 | 9.8 | 90 | 0.3 | 23 | 22 | 3.4 | NC | 8 | 92 | 0.87 |
| | 4 | 144 | 3.8 | 101 | 23 | 12 | 0.95 | 4.6 | 8.2 | 10.4 | 84 | 0.4 | 22 | 17 | 3.5 | NC | 14 | 101 | 0.59 |
| | 18 | 141 | 3.7 | 100 | 25 | 14 | 0.94 | 4.9 | 8.5 | 10.5 | 81 | 0.6 | 22 | 18 | 3.5 | NC | 15 | 95 | 0.88 |
| | 22 | 140 | 3.5 | 97 | 28 | 9 | 0.88 | 4.9 | 8.7 | 10.5 | 70 | 0.5 | 24 | 24 | 3.8 | | 15 | 99 | 1.1 |
| 37 | 0 | 138 | 3.7 | 105 | 23 | 12 | 0.6 | 4.3 | 7.5 | 9.8 | 207 | 0.4 | 31 | 36 | 3.2 | NC | 9 | 82 | 2.07 |
| | 4 | 139 | 4.2 | 105 | 22 | 15 | 0.62 | 4.3 | 7.2 | 9.8 | 197 | 0.3 | 27 | 53 | 2.9 | NC | 12 | 102 | 2.13 |
| | 18 | 135 | 3.9 | 104 | 22 | 10 | 0.65 | 4.5 | 7.4 | 9.7 | 168 | 0.4 | 31 | 63 | 2.9 | NC | 13 | 97 | 1.98 |
| | 22 | 138 | 3.9 | 104 | 24 | 9 | 0.66 | 4.5 | 7.4 | 10.2 | 167 | 0.5 | 35 | 68 | 2.9 | NC | 10 | 87 | 2.11 |
| 38 | 0 | 143 | 4 | 107 | 26 | 8 | 0.67 | 4.2 | 7.4 | 9.8 | 189 | 0.4 | 16 | 9 | 3.2 | NC | 10 | 104 | 0.65 |
| | 4 | 139 | 4.8 | 103 | 23 | 7 | 0.55 | 4.5 | 7.7 | 10.3 | 213 | 0.6 | 20 | 7 | 3.2 | NC | 13 | 86 | 1.07 |
| | 18 | - | - | - | - | - | - | - | - | - | - | - | - | - | - | - | - | - | - |
| | 22 | 139 | 4 | 107 | 24 | 9 | 0.59 | 4.2 | 7.2 | 9.8 | 209 | 0.4 | 18 | 10 | 3 | NC | 8 | 91 | 0.91 |

Fig. 9 (Continued)

| | | | | | | | | | | | | | | | | | | |
|---|---|---|---|---|---|---|---|---|---|---|---|---|---|---|---|---|---|---|
| 40 | 0 | 142 | 3.7 | 106 | 21 | 7 | 0.64 | 4.4 | 7.3 | 9.8 | 67 | 0.4 | 17 | 16 | 2.9 | >60 | 15 | 126 | 0.96 |
| | 4 | 140 | 4.3 | 105 | 26 | 12 | 0.63 | 4.2 | 6.9 | 9.3 | 74 | 0.4 | 20 | 23 | 2.7 | >60 | 9 | 87 | 0.9 |
| | 18 | 139 | 3.7 | 104 | 22 | 16 | 0.44 | 4.3 | 7.2 | 9.6 | 67 | 0.4 | 23 | 24 | 2.9 | >60 | 13 | 120 | 0.75 |
| | 22 | | | | | | | | | | | | | | | | | | |
| 42 | 0 | 139 | 3.4 | 101 | 25 | 11 | 0.61 | 4 | 7.6 | 9.5 | 75 | 0.2 | 58 | 87 | 3.6 | >60 | 13 | 89 | 12.13 |
| | 4 | 138 | 3.8 | 102 | 24 | 14 | 0.64 | 4 | 7.7 | 10.1 | 58 | 0.4 | 52 | 91 | 3.7 | >60 | 12 | 144 | 2.48 |
| | 18 | 138 | 3.9 | 100 | 27 | 13 | 0.65 | 3.8 | 7.4 | 9.8 | 71 | 0.3 | 32 | 60 | 3.6 | >60 | 11 | 204 | 6.51 |
| | 22 | 141 | 4.2 | 104 | 25 | 11 | 0.62 | 3.9 | 7.4 | 9.6 | 35 | 0.2 | 74 | 142 | 3.5 | >60 | 12 | 85 | 3.52 |
| 44 | 0 | 137 | 4.2 | 103 | 26 | 16 | 0.78 | 4.3 | 7.5 | 9.8 | 75 | 0.4 | 24 | 53 | 3.2 | NC | 8 | 98 | 2.04 |
| | 4 | 140 | 4.2 | 103 | 22 | 12 | 0.82 | 4.4 | 7.5 | 9.5 | 74 | 0.3 | 21 | 50 | 3.1 | NC | 15 | 97 | 1.55 |
| | 18 | 140 | 3.8 | 102 | 22 | 14 | 0.78 | 4.6 | 7.5 | 9.9 | 77 | 0.5 | 25 | 66 | 2.9 | >60 | 16 | 80 | 2.07 |
| | 22 | | | | | | | | | | | | | | | | | | |

Column Headings: Bili - Bilirubin; Gluc - Glucose; Prot - protein; spec grav - specific gravity; Turbid - turbidity; Urobil - urobilogen; WBC Est - WBC Esterase; Na - sodium; K - potassium; Cl - chloride; creat - creatinine; Alb - albumin; TP - total protein; Ca - calcium; AP - alkaline phosphatase; TB - total bilirubin; Glob - globulin; An Gap - anion gap; Plas Gluc - plasma glucose; Other: NC - not calculated; Neg - negative; Y - yellow

Fig. 10
Formula VIII;
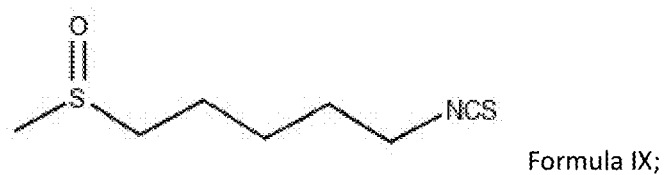
Formula IX;
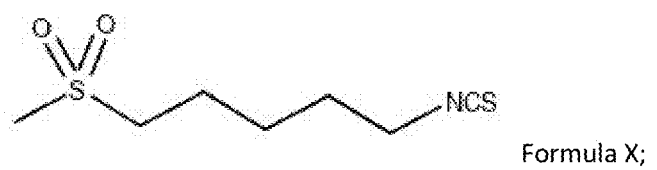
Formula X;
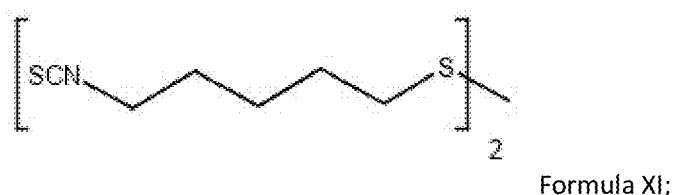
Formula XI;
Formula XII;
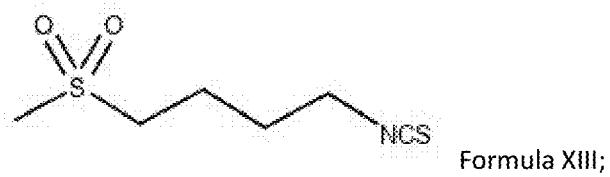
Formula XIII;
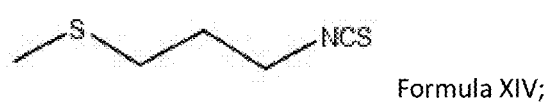
Formula XIV;
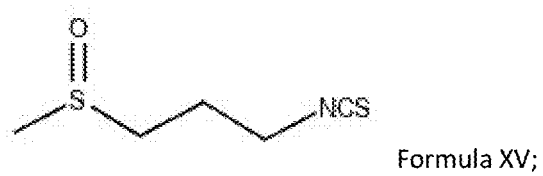
Formula XV;

Fig. 10 (continued)
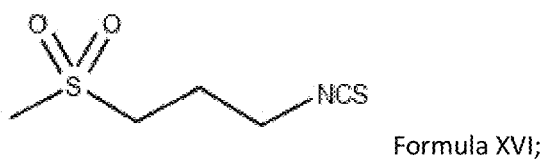
Formula XVI;
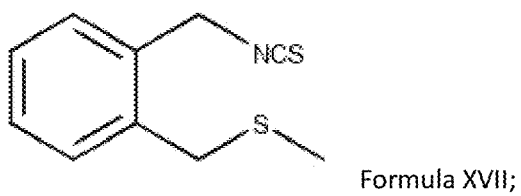
Formula XVII;
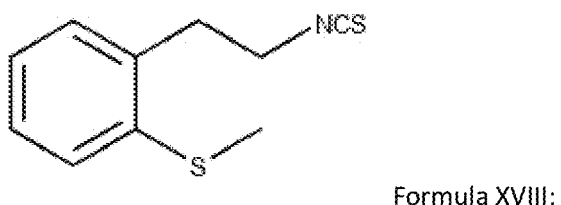
Formula XVIII;
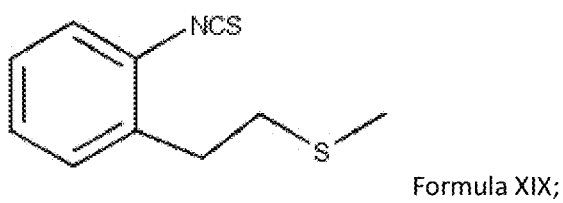
Formula XIX;
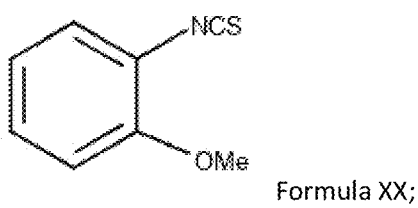
Formula XX;
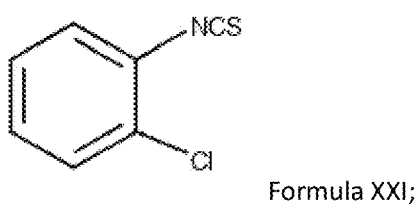
Formula XXI;

Fig. 10 (continued)
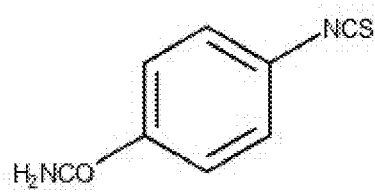
Formula XXII;
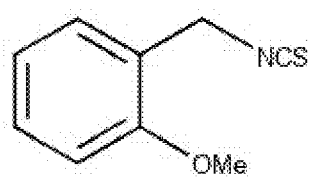
Formula XXIII;
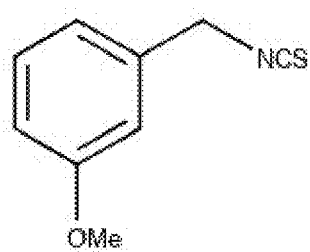
Formula XXIV
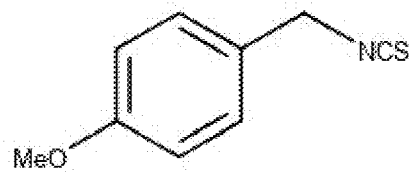
Formula XXV;
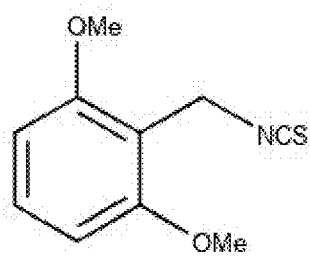
Formula XXVI;

Fig. 10 (continued)
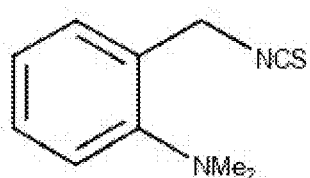
Formula XXVII;
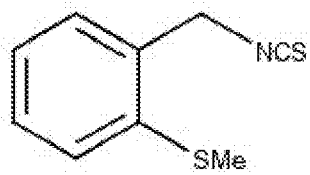
Formula XXVIII;
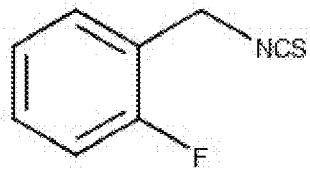
Formula XXIX;
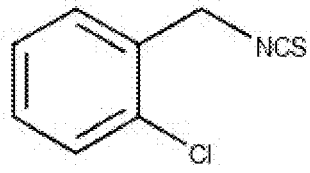
Formula XXX;
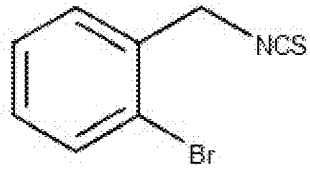
Formula XXXI;
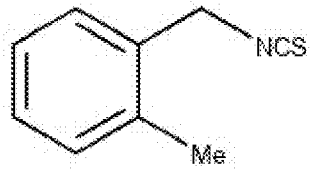
Formula XXXII;

Fig. 10 (continued)
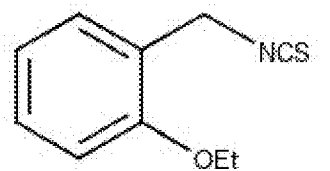
Formula XXXIII;
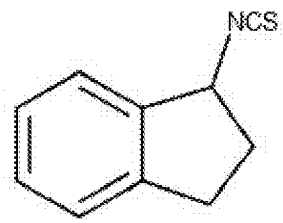
Formula XXXIV;
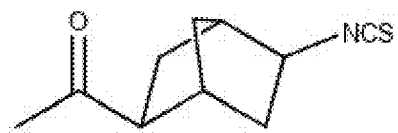
Formula XXXV;
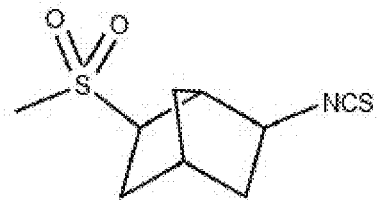
Formula XXXVI;
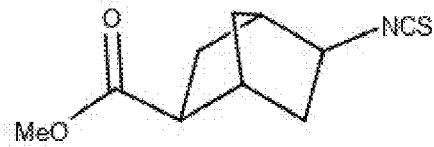
Formula XXXVII;
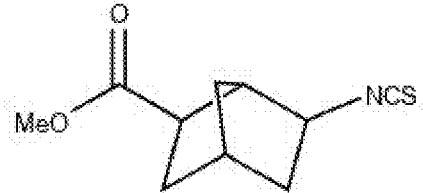
Formula XXXVIII;

Fig. 10 (continued)
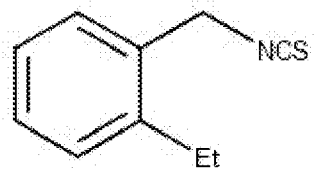
Formula XXXIX;
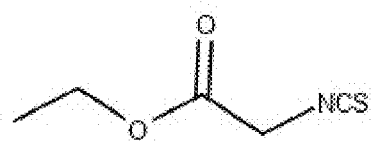
Formula XL;
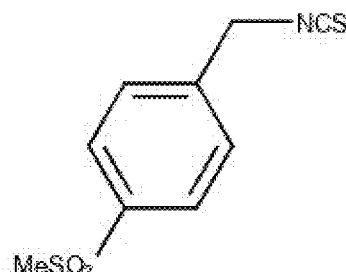
Formula XLI;
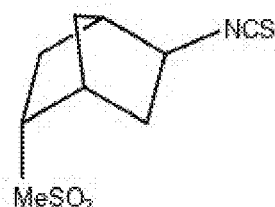
Formula XLII;
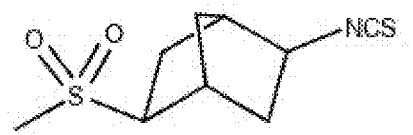
Formula XLIII;
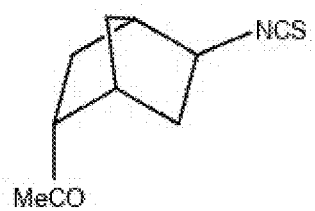
Formula XLIV;

Fig. 10 (continued)
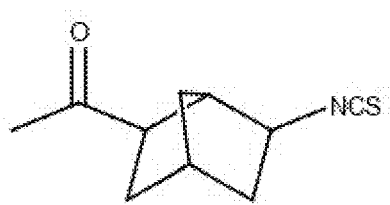
Formula XLV;
Formula XLVI;
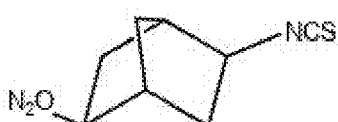
Formula XLVII;
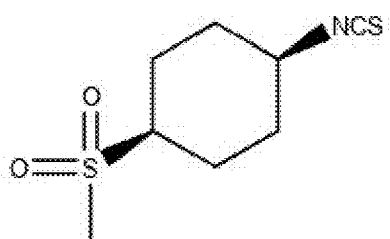
Formula XLVIII;
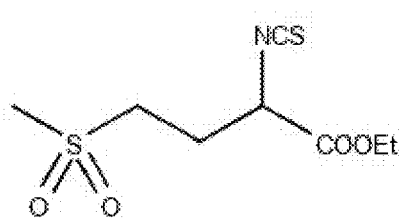
Formula XLIX;
Formula L;

Fig. 10 (continued)
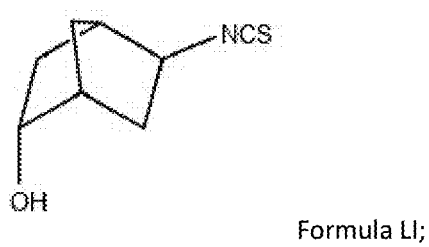
Formula LI;
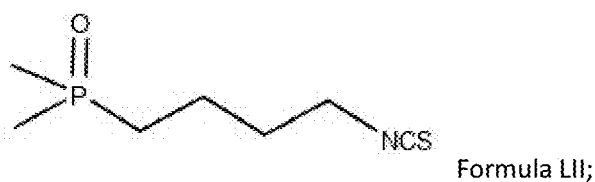
Formula LII;
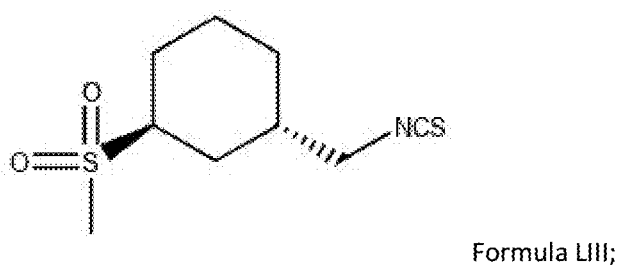
Formula LIII;
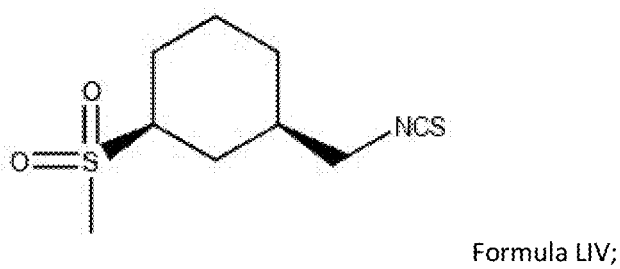
Formula LIV;
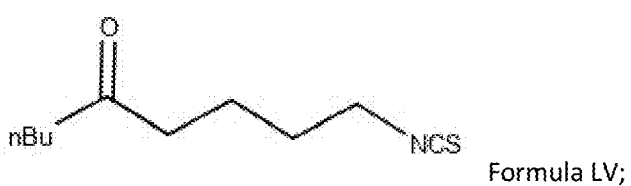
Formula LV;

Fig. 10 (continued)
Formula LVI;
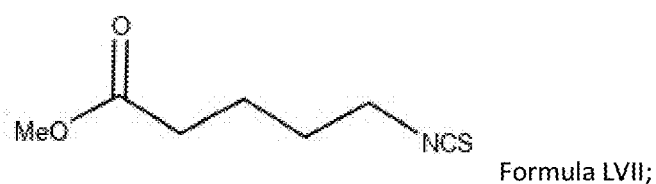
Formula LVII;
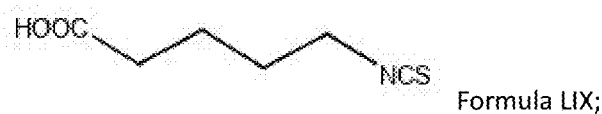
Formula LIX;
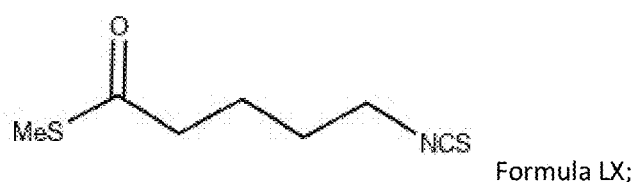
Formula LX;
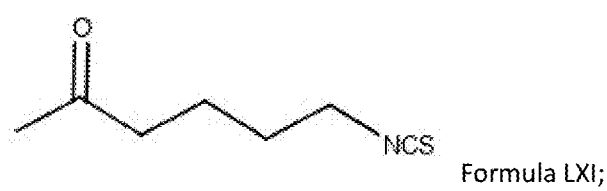
Formula LXI;
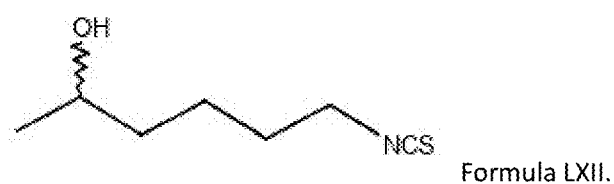
Formula LXII.

COMPOSITIONS AND METHODS FOR TREATING AUTISM SPECTRUM DISORDERS

CROSS-REFERENCE TO RELATED APPLICATIONS

This application is a 371 of PCT/US15/53657, filed Oct. 2, 2015, which claims priority to U.S. provisional application 62/059,594, filed Oct. 3, 2014; This application Ser. No. 15/524,334 is a continuation in part application of U.S. application Ser. No. 14/512,175, filed Oct. 10, 2014, now abandoned, which is a continuation application of U.S. application Ser. No. 13/665,679, filed Oct. 31, 2012, now U.S. Pat. No. 8,937,050, which claims priority to U.S. provisional application 61/558,486, filed Nov. 11, 2011, to U.S. provisional application 61/558,094, filed Nov. 10, 2011, and to U.S. provisional application 61/553,509, filed Oct. 31, 2011.

BACKGROUND

Autism Spectrum Disorder (ASD) encompasses a group of complex disorders of brain development. These disorders are characterized, in varying degrees, by difficulties in social interaction, verbal and nonverbal communication and repetitive behaviors. These disorders include, but are not limited to, autistic disorder, childhood disintegrative disorder, pervasive developmental disorder-not otherwise specified (PDD-NOS), and Asperger syndrome. ASD affects 1-2% of predominantly male individuals. ASD is an enormous medical and economic problem in the United States and, at present, there is no approved, mechanism-based treatment.

SUMMARY

The disclosure is based, at least in part, on the results from a clinical study demonstrating that patients with moderate to severe autism exhibited marked improvements in aberrant behavior and verbal communication following treatment with sulforaphane. In fact, on subscale analysis of Clinical Global Impression-Improvement (CGI-I) scale scores after treatment with sulforaphane, 46%, 54%, and 42% of sulforaphane recipients were much or very-much improved on social interaction, aberrant behavior, and verbal communication, respectively, as compared to 0%, 9%, and 0%, respectively, for placebo recipients. These studies indicate that compositions comprising an isothiocyanate (e.g., sulforaphane or derivatives of sulforaphane) possessing sulforaphane activity, are useful for treating autism spectrum disorders in humans.

Accordingly, in one aspect, the disclosure features a method for treating an autism spectrum disorder in a human. The method comprises administering to the human an effective amount of an isothiocyanate, such as sulforaphane or a derivative thereof, to thereby treat the disorder.

In another aspect, the disclosure features a method for treating an autism spectrum disorder in a human. The method comprises administering to the human an effective amount of an isothiocyanate (e.g., sulforaphane or a derivative thereof) to thereby treat the disorder, wherein the human has not experienced a seizure within one year prior to administering the sulforaphane or derivative thereof.

In yet another aspect, the disclosure features a method for treating an autism spectrum disorder in a human, which method comprises administering to the human: (a) an effective amount of an isothiocyanate (e.g., sulforaphane or a derivative thereof) to thereby treat the disorder; and (b) an effective amount of an anti-seizure drug.

In another aspect, the disclosure features a method for treating an autism spectrum disorder in a human, the method comprising administering to the human an effective amount of an isothiocyanate (e.g., sulforaphane or a derivative thereof) to thereby treat the disorder, wherein the human is not concurrently being treated with a drug associated with increased risk of seizure.

In another aspect, the disclosure features a method for treating an autism spectrum disorder, which method comprises: (i) administering to the human an effective amount of an isothiocyanate (e.g., sulforaphane or a derivative thereof) to thereby treat the disorder; and (ii) monitoring the human for the occurrence of seizures.

In another aspect, the disclosure features a method for treating an autism spectrum disorder in a human, the method comprising administering to the human an effective amount of an isothiocyanate (e.g., sulforaphane or a derivative thereof) to thereby treat the disorder, wherein the isothiocyanate (e.g., the sulforaphane or derivative thereof) is to be administered in conjunction with a reduced calorie diet.

In some embodiments of any of the methods described herein, the autism spectrum disorder is autistic disorder, childhood disintegrative disorder, pervasive developmental disorder-not otherwise specified (PDD-NOS), or Asperger syndrome.

In some embodiments of any of the methods described herein, the effective amount of an isothiocyanate (e.g., sulforaphane or a derivative thereof) can be, e.g., between 25 and 75 µmol if the human weighs 100 pounds or less; between 75 and 125 µmol if the human weighs between 101 to 199 pounds; or between 125 and 175 µmol if the human weighs more than 200 pounds. The effective amount can be administered daily. In some embodiments, the effective amount of an isothiocyanate (e.g., sulforaphane or a derivative thereof) can be 50 µmol, if the human weighs 100 pounds or less; between 100 µmol if the human weighs between 101-199 pounds; or 150 µmol if the human weighs more than 200 pounds. In some embodiments, the effective amount is 5 to 15 mg, 15 to 25 mg, 20 to 30 mg, or 5 to 50 mg, e.g., daily. In some embodiments, the effective amount (e.g., the effective daily amount) is 5 to 15 mg if the human weighs less than 100 pounds; 15 to 25 mg if the human weighs between 101 and 199 pounds, or 20 to 35 mg if the human weighs more than 200 pounds. In some embodiments, the effective amount is 4 to 12.5 mg, 9 to 25 mg, 12.5 to 38 mg, or 3 to 45 mg, e.g., daily. In some embodiments, the effective amount (e.g., the effective daily amount) is 4 to 12.5 mg if the human weighs less than 100 pounds; 9 to 25 mg if the human weighs between 101 and 199 pounds, or 12.5 to 38 mg if the human weighs more than 200 pounds.

In some embodiments of any of the methods herein, the effective amount is sufficient to produce at least a 30 (e.g., at least a 35, 40, 45, 50, 55, 60, 65, 70, 75, 80, 85, or 90) % decrease in total Aberrant Behavior Checklist (ABC) and/or Social Responsiveness Scale (SRS) scores (see working examples) for a human with ASD relative to the score(s) prior to treatment with the effective amount of sulforaphane or derivative thereof.

In some embodiments of any of the methods described herein, the effective amount is administered as one dose. In some embodiments, the amount is administered as more than one (e.g., at least two, three, four, or five or more) dose(s). For example, in some embodiments, the effective amount of an isothiocyanate (e.g., sulforaphane or a derivative thereof) is administered to a patient once daily as a single dose (e.g., a single capsule or tablet comprising between 10 to 200 µmol of an isothiocyanate (e.g., sulforaphane or a derivative thereof)). In another example, the isothiocyanate (e.g., sulforaphane or derivative thereof) can be administered to a patient as more than one dose per day, such that the total amount administered in one day is the effective amount (e.g., two or three capsules or tablets taken daily).

In some embodiments of any of the methods described herein, the isothiocyanate (e.g., sulforaphane or derivative thereof) is administered to the human for at least four (e.g., at least five, six, seven, eight, nine, 10, 11, 12, 13, 14, 15, 16, 17, or 18) weeks. In some embodiments of any of the methods described herein, the isothiocyanate (e.g., sulforaphane or derivative thereof) is administered to the human for at least three (e.g., at least four, five, six, seven, eight, nine, 10, 12, 18, 24, 36, 48, or 60) months. In some embodiments of any of the methods described herein, the isothiocyanate (e.g., sulforaphane or derivative thereof) is to be administered for the lifetime of the human with the autism spectrum disorder.

In some embodiments of any of the methods described herein, the human has moderate to severe autism. In some embodiments, the human has severe autism.

In some embodiments, any of the methods described herein can further comprise determining whether the human has an autism spectrum disorder. Methods for making such a determination are known in the art (e.g., Diagnostic and Statistical Manual of Mental Disorders (DSM), e.g., DSM-V), described herein, and exemplified in the working examples.

In some embodiments of any of the methods described herein, the effective amount is sufficient to reduce the severity of one or more behavioral symptoms of the disorder. In some embodiments of any of the methods described herein, the effective amount is sufficient to reduce the severity of one or more symptoms of the disorder by at least 10 (e.g., at least 15, 20, 25, 30, 35, 40, 45, 50, 55, 60, 65, 70, 75, or 80) %. Methods for measuring the efficacy of a treatment for autism are known in the art, described herein, and exemplified in the working examples.

In some embodiments of any of the methods described herein, the human is a male.

In some embodiments of any of the methods described herein, the human is an adolescent or an infant. In some embodiments of any of the methods described herein, the human is between 13 to 30 years of age. In some embodiments of any of the methods described herein, at least six months (e.g., at least seven months, at least eight months, at least nine months, at least one year, at least 18 months, or at least two years) prior to administering the sulforaphane or derivative thereof, the human has not had a seizure (e.g., has not reported experiencing a seizure). In some embodiments, the human is not overweight. In some embodiments, the human is not obese. In some embodiments, the human is not hypertensive. In some embodiments, the human is not at an increased risk for cardiovascular disease.

In some embodiments, any of the methods described herein can further include monitoring a human for an improvement in one or more symptoms of the disorder.

In yet another aspect, the disclosure features a pharmaceutical composition comprising: a pharmaceutically-acceptable carrier and an effective amount of an isothiocyanate (e.g., sulforaphane or a derivative thereof). In some embodiments, the effective amount is between 25 µmol and 200 µmol (e.g., between 50 and 150 µmol) of an isothiocyanate (e.g., sulforaphane or a derivative thereof).

In another aspect, the disclosure features a pharmaceutical composition comprising an effective dose of an isothiocyanate (e.g., sulforaphane or a derivative thereof), wherein the effective dose comprises 50 µmol or more. In some embodiments, the effective dose is no more than 300 (e.g., 275, 250, 225, 200, 175, 150, 125, 100, or 75) µmol of the active ingredient (e.g., an isothiocyanate, such as sulforaphane or a derivative thereof).

In another aspect, the disclosure features a pharmaceutical unit dosage form of an isothiocyanate (e.g., sulforaphane or a derivative thereof), wherein the dosage form comprises between 10 µmol and 200 µmol of an isothiocyanate (e.g., sulforaphane or a derivative thereof). In some embodiments, the dosage form comprises between 25 µmol and 100 µmol of an isothiocyanate (e.g., sulforaphane or a derivative thereof). In some embodiments, the dosage form comprises between 25 µmol and 75 µmol of an isothiocyanate (e.g., sulforaphane or a derivative thereof). In some embodiments, the dosage form comprises between 25 µmol and 50 µmol of an isothiocyanate (e.g., sulforaphane or a derivative thereof). In some embodiments, the dosage form comprises between 10 µmol and 50 µmol of an isothiocyanate (e.g., sulforaphane or a derivative thereof). In some embodiments, the dosage form comprises between 10 µmol and 100 µmol of an isothiocyanate (e.g., sulforaphane or a derivative thereof). In some embodiments, the dosage form comprises between 10 µmol and 25 µmol of an isothiocyanate (e.g., sulforaphane or a derivative thereof).

In another aspect, the disclosure features a food, beverage, medical food, or a dietary supplement comprising between 25 µmol and 200 µmol of an isothiocyanate. In another aspect, the disclosure features a medical food or a dietary supplement comprising an effective dose of an isothiocyanate, wherein the effective dose comprises 50 µmol. The isothiocyanate can be, e.g., sulforaphane or a derivative thereof. The medical foods and/or dietary supplements can optionally include a label identifying the products as such and/or providing exemplary dosages and dosing schedules for the product.

Additional suitable isothiocyanate content for the pharmaceutical compositions, unit dosage forms, food, beverage, medical foods, dietary supplements, and other compositions embraced by the disclosure are described herein (infra).

The clinical results set forth herein also indicate that sulforaphane precursor compounds, e.g., glucoraphanin, are also useful for the treatment of an autism spectrum disorder. Accordingly, in another aspect, the disclosure features a food or beverage (or medical food or dietary supplement) composition comprising a glucosinolate and, optionally, an enzyme (e.g., an isolated glucosinolate compound and an isolated enzyme). The enzyme is capable of converting the glucosinolate to a thiocyanate or an isothiocyanate (e.g., conversion in the gut of the human). The glucosinolate can be a sulforaphane precursor, such as glucoraphanin (infra), or a glucosinolate precursor to a sulforaphane derivative, such as any of the sulforaphane derivatives described herein.

In some embodiments of any of the compositions or methods described herein, the enzyme can be a myrosinase. In some embodiments, the enzyme can be a thioglucosidase, a glutathione transferase, an NAD(P)H:quinone reductase, or a glucuronosyltransferase. In some embodiments of any of the compositions or methods described herein, a composition (e.g., a food, beverage, medical food, or dietary supplement) described herein can contain more than one (e.g., at least two, three, four, or five) different enzyme(s) (e.g., different isolated enzymes).

In some embodiments of any of the compositions or methods described herein, the composition comprises an amount of the glucosinolate and, optionally, an enzyme sufficient to produce in a human each day: between 25 and 75 µmol of an isothiocyanate if the human weighs 100 pounds or less; between 75 and 125 µmol of an isothiocyanate if the human weighs between 101 to 199 pounds; or between 125 and 175 µmol of the isothiocyanate if the human weighs more than 200 pounds. The isothiocyanate can be, e.g., sulforaphane or a derivative thereof.

In some embodiments of any of the methods or compositions described herein, the glucosinolate is glucoraphanin. In some embodiments, the composition comprises a myrosinase.

In some embodiments, a composition (e.g., a food, beverage, medical food, or dietary supplement composition described herein) comprises, or is, a food bar, yogurt, ice cream, fruit, fruit puree, or cereal. The food or beverage composition can be or comprise, e.g., a dessert or a confection.

In some embodiments, a composition (e.g., a food, beverage, medical food, or dietary supplement composition described herein) comprises, or is, a dairy product, vegetable juice, or fruit juice.

Any of the compositions, e.g., food, beverage, medical food, or dietary supplements described herein can be used for treating, preventing, and/or ameliorating one or more symptoms of an autism spectrum disorder.

In yet another aspect, the disclosure features a method for treating an autism spectrum disorder in a human, which method comprises administering to the human a composition in an amount effective to treat the autism spectrum disorder, wherein the composition comprises a glucosinolate (e.g., an isolated glucosinolate) and, optionally, at least one enzyme (e.g., an isolated enzyme) capable of converting the glucosinolate to a thiocyanate or an isothiocyanate. In some embodiments, the composition can be, e.g., a food, beverage, medical food, dietary supplement, or other composition described herein. In some embodiments, the enzyme is myrosinase. In some embodiments, the enzyme (e.g., isolated enzyme) is a thioglucosidase, a glutathione transferase, an NAD(P)H:quinone reductase, or a glucuronosyltransferase. In some embodiments, the composition comprises more than one different enzyme.

In some embodiments of any of the methods or compositions described herein, the sulforaphane or derivative thereof is substantially enantiopure, e.g., for the (R) enantiomer. In some embodiments, the sulforaphane or derivative thereof is a racemic mixture of both the (R) and (S) enantiomers. In some embodiments, the composition is an extract from a cruciferous plant (e.g., broccoli, broccoli sprouts, cauliflower, or kale) that is, optionally, enriched for sulforaphane.

In some embodiments, the pharmaceutical composition, unit dosage forms, medical foods, or dietary supplements described herein can be a capsule or tablet comprises between 100 to 500 mg of cruciferous plant (or plant seed or sprout) extract, e.g., an extract from broccoli sprouts seeds, such as BroccoSprouts™ seeds. In some embodiments, the pharmaceutical composition or unit dosage form comprises about 250±50 mg (e.g., approximately 232 mg) of cruciferous plant (or plant seed or sprout) extract, e.g., an extract from broccoli sprouts seeds, such as BroccoSprouts™ seeds.

The isothiocyanate compound can be, e.g., any of those described herein.

In some embodiments of any of the methods, compositions, or dosage forms described herein, the sulforaphane derivative has any one of the structural formulas (II) to (VII) shown below.

In some embodiments of any of the methods, compositions, or dosage forms described herein, the sulforaphane derivative has at least 10 (e.g., at least 15, 20, 25, 30, 35, 40, 45, 50, 55, 60, 65, 70, 75, 80, 85, 90, 95, 98, 99, 100, or more) % of the in vitro or in vivo biological activity of an equivalent molar amount of sulforaphane to induce a protective response in cells (e.g., normal human fibroblasts or murine liver cells), e.g., promote expression of stress responsive genes.

In some embodiments, any of the compositions, pharmaceutical compositions and dosage forms described herein are for use in treating an autism spectrum disorder, e.g., autism, such as moderate to severe autism.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating an autism spectrum disorder in a human, will be apparent from the following description, the examples, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a table providing the baseline physiological characteristics of patients in the study.

FIGS. 3A (ABC) and 3D (SRS) show all observations. Means of changes in raw, unadjusted total scores (±S.E.M.) at 4, 10, 18, and 22 weeks are shown in FIGS. 3B for ABC and 3E for SRS. Reductions in ABC score upon sulforaphane treatment were −20.2% (P=0.035), −31.5% (P=0.002) and −33.6% (P<0.001), at 4, 10, and 18 weeks, respectively. The corresponding changes in SRS were −12.2% (P=0.29), −12.2% (P=0.080) and −16.8% (P=0.017). FIG. 3C (ABC) and 3F (SRS) show the changes in total scores at all time-points for placebo- and sulforaphane-treated participants. All changes were calculated from the initial values for each individual participant at time 0 (the means of the two values obtained at screening and at enrollment).

FIGS. 6A and 6B are each tables depicting the effect of sulforaphane treatment on total scores and changes in total scores. FIG. 6A provides the ABC (Aberrant Behavior Checklist) and SRS (Social Responsiveness Scale) total scores of participants who completed at least one post-intervention measurement (n=40). The ABC and SRS scores and changes thereof from baseline are the raw, unadjusted values while the P-values are from the linear mixed model adjusting for repeated measures. FIG. 6B provides the CGI-I (Clinical Global Impression-Improvement) scores at 18 weeks for the 37 subjects for whom scores were available.

FIG. 8 is a table providing the summary of adverse events reported and laboratory results obtained from the patient visit at 18 weeks.

FIG. 9 is a table providing the complete laboratory studies (including hematology, chemistry, and urinalysis) for the patients in the study.

FIG. 10 is a series of chemical structures of exemplary sulforaphane derivative compounds.

DETAILED DESCRIPTION

Figure 2:
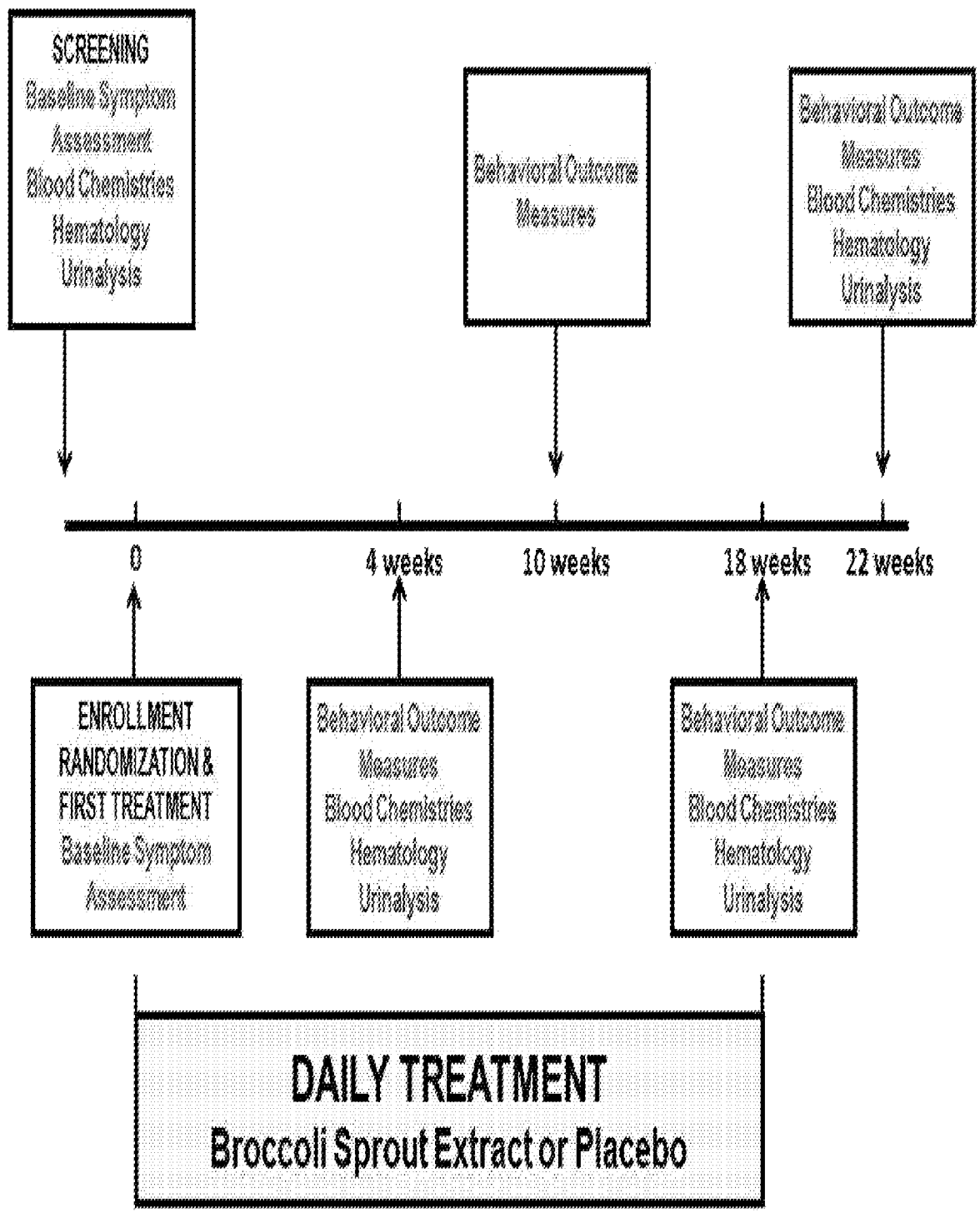
FIG. 2 depicts the schedule used for a study of the effects of sulforaphane in ASD.

The disclosure features, among other things, compositions and methods for treating an autism spectrum disorder in a human. While in no way intended to be limiting, exemplary compositions, pharmaceutical compositions, dosage forms, dosage regimens, and methods for treatment are set forth below.

Glucosinolates

Glucosinolates refer to a class of compounds that contain both sulfur and nitrogen and are derived from glucose and an amino acid. These compounds, naturally found in a variety of cruciferous plants, are converted to isothiocyanates by enzymes, such as thioglucosides, for example, myrosinase. Generally, in plant cells, myrosinase and glucosinolates are separated in the cell and if the cell is damaged, such as by insect predation, with loss of compartmentalization, myrosinase or other similarly acting enzymes comes into contact with glucosinolates, which are then converted to isothiocyanates. Myrosinase (EC 3.2.1.147, CAS® Registry Number: 9025-38-1) is known to those of skill in the art, as are similarly acting enzymes that convert precursor molecules, such as glucosinolates, to more active compounds, such as isothiocyanates, e.g., sulforaphane. It is understood that glucosinolates can be either naturally-occurring compounds (e.g., those produced by plants) or synthetic (e.g., analogs or derivatives of glucosinolates found in plants), or a mixture of natural and synthetic compounds.

The disclosure also features compositions comprising a glucosinolate and one or more enzymes, and/or one or more types of enzymes, and optionally co-factors or other enzymes in the metabolic pathway, for the treatment of autism and autism spectrum disorders. Such enzymes can be, but are not limited to, myrosinase, thioglucosidases, glutathione transferases, NAD(P)H:quinone reductase (QR) and glucuronosyltransferases, which have similar activities or are in related pathways. For example, as known in the art, in the presence of water, myrosinase cleaves the glucose group from a glucosinolate. The remaining molecule then converts to a thiocyanate, an isothiocyanate or a nitrile; these are the active substances that serve as defense for the plant. Thus, compositions featuring a glucosinolate (e.g., an isolated glucosinolate, such as glucoraphanin or a derivative thereof) and an enzyme (e.g., an isolated enzyme, such as myrosinase) allow for the conversion of the glucosinolate to an isothiocyanate (e.g., sulforaphane or a derivative thereof) in vivo. The compositions can be formulated to contain an amount of the glucosinolate and, optionally, an enzyme such that an effective amount of an isothiocyanate (e.g., sulforaphane or a derivative thereof) is produced in the human who has consumed the composition or to whom the composition was administered. Exemplary effective amounts of sulforaphane and/or derivatives thereof are described herein.

Isothiocyanates

An isothiocyanate (ITC) refers to a phytochemical compound comprising an —N=C=S functional group. These compounds have been associated with a number of positive properties, including, e.g., inhibiting cancer development (e.g., anti-oxidant properties) as well as having anti-inflammatory and anti-microbial properties. Brown and Hampton (2011) *Biochim Biophys Acta* 1810(9):888-894. As discussed above, isothiocyanates exist as precursor molecules, glucosinolates, in cruciferous vegetables and chemically generated, e.g., by myrosinase following damage to plant tissue (such as chewing or cutting) or by the action of intestinal bacteria. Singh and Singh (2012) *Carcinogenesis* 33(10): 1833-1842. For example, the glucosinolate precursor of phenethyl isothiocyanate (PEITC) is gluconasturtiin (e.g., in watercress). Sulforaphane, by contrast, is derived from glucoraphanin (4-methylsulfinylbutyl glucosinolate; 1-thio-, 1-(5-(methylsulfinyl)-N-(sulfoxy)pentanimidate)), which is found in cruciferous vegetables.

Exemplary isothiocyanates include, e.g., PEITC, benzyl-ITC (BITC), and sulforaphane. Additional exemplary isothiocyanates include, without limitation, 1-adamantyl isothiocyanate; 1-naphthyl isothiocyanate; 2,4,6-trimethylphenylisothiocyanate; 2,4,6-trichlorophenyl isothiocyanate; 2,4-dichlorophenyl isothiocyanate; 2,4-dimethoxyphenyl isothiocyanate; 2,4-xylyl isothiocyanate; 2,5-dichlorophenyl isothiocyanate; 2,5-difluorophenyl isothiocyanate; 2,5-dimethoxyphenyl isothiocyanate; 2,6-difluorophenyl isothiocyanate; 2,6-dimethylphenyl isothiocyanate; 2-(methylthio)phenyl isothiocyanate; 2-(trifluoromethyl)phenyl isothiocyanate; 2-bromophenyl isothiocyanate; 2-chloro-4-nitrophenyl isothiocyanate; 2-chloro-5-(trifluoromethyl)phenyl isothiocyanate; 2-chloroethyl isothiocyanate; 2-chlorophenyl isothiocyanate; 2-ethylphenyl isothiocyanate; 2-fluorophenyl isothiocyanate; 2-iodophenyl isothiocyanate; 2-methoxy-4-nitrophenyl isothiocyanate; 2-methoxy-5-methylphenyl isothiocyanate; 2-methoxyphenyl isothiocyanate; 2-napthyl isothiocyanate; 2-phenethyl isothiocyanate; 2-phenylethyl isothiocyanate; phenethyl isothiocyanate; 3,3,5-trimethylcyclohexyl isothiocyanate; 3,4,5-trimethoxyphenyl isothiocyanate; 3,4-dichlorophenyl isothiocyanate; 3,5-bis(trifluoromethyl)phenyl isothiocyanate; 3,5-di-tert-buryl-4-hydroxyphenyl isothiocyanate; 3,5-dichlorophenyl isothiocyanate; 3-(methylthio)propyl isothiocyanate; 3-(trifluoromethyl)phenyl isothiocyanate; 3-bromophenyl isothiocyanate; 3-chlorophenyl isothiocyanate; 3-cyanophenyl isothiocyanate; 3-fluorophenyl isothiocyanate; 3-methoxyphenyl isothiocyanate; 3-methoxypropyl isothiocyanate; 3-nitrophenyl isothiocyanate; 3-pyridyl isothiocyanate; 4-(methylthio)phenyl isothiocyanate; 4-(trifluoromethyl)phenyl isothiocyanate; 4-bromo-2-chlorophenyl isothiocyanate; 4-bromophenyl isothiocyanate; 4-chlorophenyl isothiocyanate; 4-cyanophenyl isothiocyanate; 4-dimethylamino-1-naphthyl isothiocyanate; 4-ethylphenyl isothiocyanate; 4-fluorophenyl isothiocyanate; 4-iodophenyl isothiocyanate; 4-isopropylphenyl isothiocyanate; 4-methoxyphenyl isothiocyanate; 4-methyl-2-nitrophenyl isothiocyanate; 4-methylphenyl isothiocyanate; 4-nitrophenyl isothiocyanate; 5-chloro-2-methylphenyl isothiocyanate; m-tolyl isothiocyanate; o-tolyl isothiocyanate; p-tolyl isothiocyanate; tert-butyl isothiocyanate; acetyl isothiocyanate; benzoyl isothiocyanate; ethyl isothiocyanate; cyclohexyl isothiocyanate; hexyl isothiocyanate; methallyl isothiocyanate; methyl isothiocyanate; pentyl isothiocyanate; and 2,3-dichlorophenyl isothiocyanate (see, e.g., U.S. Pat. No. 7,105,190, the disclosure of which, as it relates to exemplary isothiocyanate compounds and methods for producing them, is incorporated herein by reference in its entirety). Yet additional exemplary ITC compounds are set forth in U.S. Patent Application Publication No. 2009/0291989, the disclosure of which, as it relates to the structures of ITC compounds and methods for making the compounds, is incorporated herein by reference in its entirety.

Sulforaphane (1-isothiocyanato-4-methylsulfinylbutane) is an exemplary widely-consumed isothiocyanate found in cruciferous vegetables, such as cabbage, broccoli, broccoli sprouts, Brussels sprouts, cauliflower, cauliflower sprouts, and water cress. In the plant, sulforaphane is present in bound form as glucoraphanin, a glucosinolate. The compound has been shown to promote expression of genes responsive to stress from oxidation, inflammation, DNA damage, and radiation (Zhang et al. (1994) *Proc Natl Acad Sci USA* 91(8):3147-3150; Zhang et al. (1992) *Proc Natl Acad Sci USA* 89(6):2399-2403). Sulforaphane has the following chemical structure:

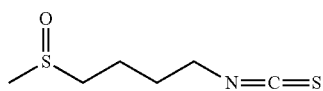

(structural formula I)

Methods for producing or obtaining sulforaphane are known in the art, described herein, and exemplified in the working examples. For example, the compound can be isolated from plants in which it is produced. The working examples describes isolation of sulforaphane from broccoli sprout extract (SF-BSE). See also Egner et al. (2014) *Cancer Prev Res* 7:813) and Azizi et al. (2011) *J Chinese Chem Soc* 58:906-910. Methods for extracting isothiocyanates from glucosinolate-containing plants are also described in, e.g., U.S. Patent Application Publication No. 20060127996.

In addition, various synthetic methods for producing sulforaphane are known in the art. Schmid and Karrer (1948) *Helvetica Chimica Acta* 31(6):1497-1505. Methods for chemically synthesizing sulforaphane are also described in, e.g., International Patent Application Publication No. WO 2013/179057 and Chen et al. (2011) *Synthesis* 24:3991-3996, the methods from which are incorporated herein by reference in their entirety. De Nicola et al. further describes a gram-scale synthetic method for enantiopure R-sulforaphane from Tuscan black kale seeds. (2014) *Molecules* 19(6):6975-6986.

Isolated isothiocyanates, such as sulforaphane, can be sensitive to oxidation and degradation. Thus, in some embodiments, an isothiocyanate (e.g., sulforaphane or a derivative (analog) thereof) can be provided or produced in a stabilized form. Stabilized forms of sulforaphane are described in, e.g., U.S. Patent Application Publication No. 20080176942, the disclosure of which as it pertains to making and using stabilized sulforaphane compositions, is incorporated herein by reference in its entirety. Methods for stabilizing sulforaphane can involve, e.g., the formation of sulforaphane-cyclodextrin complexes. For example, U.S. Pat. No. 7,879,822 describes a synthetic process for preparing sulforaphane followed by its subsequent stabilization by the formation of a sulforaphane-cyclodextrin complex. The disclosure of this patent, as it relates to the methods for making and preparing stabilized sulforaphane compositions, is incorporated herein by reference in its entirety.

Derivatives of sulforaphane are known in the art and described in, e.g., U.S. Patent Application Publication No. 20130123203, e.g., at pages 4 and 5, the disclosure of which is incorporated herein by reference in its entirety. Derivatives of sulforaphane are also described in, e.g., Hu et al. (2013) *Eur J Med Chem* 64:529-539 and Kielbasinski et al. (2014) *Eur J Med Chem* 76:332-342, the chemical structures from which, as well as methods for synthesizing such derivatives of sulforaphane, are incorporated herein by reference in their entirety. Derivatives (analogs) of sulforaphane are further described in, e.g., U.S. Patent Application Publication No. 20130142739 and Zhang and Tang (2007) *Acta Pharmacol Sin* 28(9):1343-1354 (in particular, Table 1 titled "SF analogs: relation of structure to inducer activity"), the disclosures of each of which are incorporated by reference in their entirety.

Exemplary derivatives of sulforaphane include any one of the following compounds:

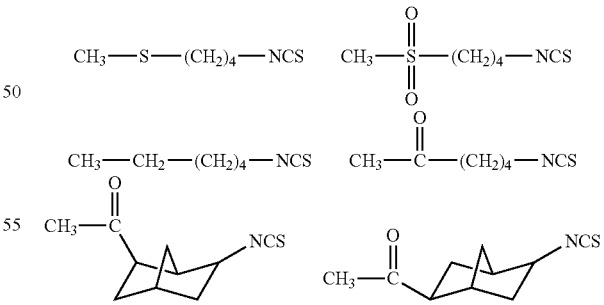

(structural formulas II, III, IV, V, VI, and VII, respectively).

In some embodiments, the derivative of sulforaphane is one of the compounds depicted in paragraph [0127] of U.S. Patent Application Publication No. 2013/0123203.

Suitable derivatives for use in the methods and compositions described herein can also be found in, e.g., U.S. Pat. No. 5,411,986, the disclosure of which (particularly Table 3 inclusive of the structures) is incorporated herein by reference in its entirety. In some embodiments, the derivative comprises or is: 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl)cyclohexylmethylisothiocyanate. In some embodiments, the derivative has one of the structures depicted in FIG. 10.

In some embodiments, an isothiocyanate (e.g., a sulforaphane derivative or analog) has at least 15 (e.g., at least 20, 25, 30, 35, 40, 45, 50, 55, 60, 65, 70, 75, 80, 85, 90, 95, 98, 99, 100, or more) % of the activity of an equivalent molar amount of sulforaphane to induce a protective response in cells. For example, Zhang and Tang (supra) describes a comparison of the biological activity of sulforaphane (both isolated from plants and chemically synthesized) and several analogs to induce the expression by cells in vitro of NAD(P)H:quinone oxidoreductase 1 (NQO1), a phase 2 enzyme associated with inhibition of carcinogenesis. U.S. Patent Application Publication No. 20130123203 (supra) describes several in vitro studies characterizing the ability of sulforaphane to induce expression of HSP70, HSP40, and HSP90 in normal human fibroblasts, e.g., at 5 micromolar (see paragraphs 279 and 284). Thus, in some embodiments, an isothiocyanate (e.g., an analog of sulforaphane) for use or inclusion in the compositions and methods described herein has at least 15 (e.g., at least 20, 25, 30, 35, 40, 45, 50, 55, 60, 65, 70, 75, 80, 85, 90, 95, 98, 99, 100, or more) % of the activity of an equivalent molar amount of sulforaphane to induce expression (e.g., mRNA or protein expression) by cells of one or more of these heat shock proteins or NQO1 in vitro. Methods for measuring mRNA or protein expression (e.g., quantitative reverse transcription-polymerase chain reaction, Northern Blot, Western Blot, or enzyme-linked immunosorbent assay (ELISA)) are known in the art and described in, e.g., Sambrook et. al., Molecular Cloning: A Laboratory Manual ($2^{nd}$ Ed.), Vol. 1-3, Cold Spring Harbor Laboratory, Cold Spring Harbor, N.Y., 1989. Sulforaphane was also shown to stimulate mitochondrial biogenesis in XALD fibroblast cells, unfolded protein response proteins (e.g., ATF4, CHOP, and elongation initiation factor 2 (eIF2α) in vitro (see paragraphs 231 to 243 of U.S. Patent Application Publication No. 20130123203. Therefore, in some embodiments, an isothiocyanate compound (e.g., a sulforaphane derivative) has at least 15 (e.g., at least 20, 25, 30, 35, 40, 45, 50, 55, 60, 65, 70, 75, 80, 85, 90, 95, 98, 99, or 100) % of the activity of sulforaphane to induce expression by a cell of an unfolded protein response protein in vitro.

Hu et al. (2006) Cancer Lett 243(2):170-192 describes enhanced expression of heat shock proteins and 26S proteasome subunits in the liver of mice treated with sulforaphane at 90 mg/kg. Accordingly, in some embodiments, an isothiocyanate compound (e.g., a sulforaphane derivative) described herein possesses at least 15 (e.g., at least 20, 25, 30, 35, 40, 45, 50, 55, 60, 65, 70, 75, 80, 85, 90, 95, 98, 99, 100, or more) % of the activity of sulforaphane to induce expression of these proteins or other stress responsive genes (protein products) in the liver of mice, e.g., when administered by the same route and at similar molar dosages. Additional methods for comparing the biological activity of an isothiocyanate compound to sulforaphane (or a sulforaphane derivative to sulforaphane) in vitro and in vivo are known in the art and described in, e.g., U.S. Patent Application Publication No. 20130123203, the disclosure of such methods is incorporated herein by reference in its entirety.

In some embodiments, the sulforaphane or derivative (analog) is a racemate of (R) and (S) enantiomers. In some embodiments, the sulforaphane or derivative thereof is substantially enantiopure in the (R) form. As used herein, substantially enantiopure refers to a preparation of an isothiocyanate (e.g., sulforaphane or a derivative thereof) that is at least 65 (e.g., 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % of one enantiomer, e.g., the (R) form. See, e.g., Khiar et al. (2009) J Org Chem 74(16):6002-6009. In some embodiments, the preparation is substantially enantiopure for (R)-sulforaphane (De Nicola et al., supra).

Plant Sources

As described above, glucosinolates can be isolated from plant sources. Methods for the extraction of natural products as sources for compounds such as sulforaphane, include methods for extraction from plant sources in contrast to those produced by chemical synthetic methods, such as from plant sources such as cruciferous vegetables include, but are not limited to homogenization of the vegetables in cold water, lyophilization, extraction of the resultant powder with acetonitrile, filtration and evaporative concentration. See, e.g., U.S. Patent Application Publication No. 20130123203. Other methods for extraction of compounds from plants are known in the art and include, for example, extractions of seeds and sprouts to produce compounds of the present invention, such as taught by U.S. Pat. No. 5,725,895, which is herein incorporated in its entirety. Known methods for extracting natural products, particularly from cruciferous plants, comprise extraction methods comprising boiling water extraction of desired compounds.

Plant sources suitable for use in the methods and compositions disclosed herein may be any portion of a cruciferous plant, including, but not limited to cells, seeds, sprouts, leaves, stalks, roots, flowers and other plant structures. Plant sources include, but are not limited to, plants from the family Cruciferae, such as Brassiceae, and including Brassicinae. For example, the plant source may be *Brassica oleracea* selected from the group of varieties of acephala (kale, collards, wild cabbage, curly kale), *medullosa* (marrowstem kale), *ramosa* (thousand head kale), *alboglabra* (Chinese kale), *botrytis* (cauliflower, sprouting broccoli), *costata* (Portuguese kale), *gemmifera* (Brussels sprouts), *gongylodes* (kohlrabi), *italica* (broccoli), *palmifolia* (Jersey kale), *sabauda* (savoy cabbage), *sabellica* (collards), and *selensia* (borecole), among others.

Useful broccoli cultivars to be used in the method and compositions disclosed herein are Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting Red Arrow, Eureka, *Excelsior*, Galleon, Ging a, Goliath, Green Duke, Greenbelt, Italian Sprouting, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, and Trixie. However, many other broccoli cultivars are suitable.

Useful cauliflower cultivars to be used in the method and compositions disclosed herein are Alverda, Amazing, Andes, Burgundy Queen, Candid Charm, Cashmere, Christmas White, Dominant, Elby, Extra Early Snowball, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, Yukon. However, many other cauliflower cultivars are suitable.

Methods for isolating glucosinolates from plant sources are known in the art. See, e.g., Devi and Thangam (2010) *Adv Biol Res* 4(6):309-313 and Bjerg and Sørensen (1987) "Isolation of Intact Glucosinolates by Column Chromatography and Determination of Purity", Glucosinolates in Rapeseeds: Analytical Aspects, World Crops: Production, Utilization, Description, Volume 13, pages 59-75. In some embodiments, the glucosinolates can be obtained from hot water extracts as described, e.g., U.S. Pat. No. 6,242,018. See also Cohen et al. (2000) *J Natl Cancer Inst* 92:61-68; Fahey et al. (1997) *Proc Natl Acad Sci USA* (1997) 94:10367-10372; Talalay et al. (2003) *Adv Enzyme Regul* 43:121-134; Shirai et al. (1997) *Cancer Res* 57:195-198; and Habig et al. (1974) *J Biol Chem* 249:7130-7139, the disclosure of each of which, in particular as it relates to isolation or extraction of glucosinolates from plant sources, is incorporated herein by reference in its entirety.

Therapeutic Compositions

Pharmaceutical Compositions

Also featured herein are pharmaceutical compositions containing an effective amount of an isothiocyanate (e.g., sulforaphane or a derivative thereof), such as any of those described herein. Further provided are compositions comprising an effective amount of a glucosinolate (e.g., a sulforaphane or sulforaphane derivative precursor, such as glucoraphanin) and, optionally, an enzyme capable of converting a glucosinolate to a thiocyanate or an isothiocyanate (e.g., sulforaphane or a derivative thereof). These compositions can be prepared in a manner well known in the pharmaceutical art, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain, as the active ingredient, a compound provided herein or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International Patent Application Publication No. WO 2002/000196. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, the active ingredient is typically dispersed evenly throughout the composition so that the composition can be readily subdivided into equally effective unit dosage forms such as tablets, pills, and capsules.

The tablets or pills provided herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compounds provided herein are formulated for intravenous administration. Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and/or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compositions can be formulated in a unit dosage form, each dosage containing, e.g., from about 5 to about 300 µmol, about 25 to about 200 µmol, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In some embodiments, the unit dosage form comprises at least 5 (e.g., at least 10, 15, 20, 25, 30, 35, 40, 45, 50, 55, 60, 65, 70, 75, 80, 85, 90, 95, 100, 11, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 3330, 340, 350, 360, 370, 380, 390, or 400 or more µmol of isothiocyanate (e.g., sulforaphane or a derivative thereof). In some embodiments, the unit dosage form comprises between 5-100 µmol of an isothiocyanate (e.g., sulforaphane or a derivative thereof). In some embodiments, the unit dosage form comprises between 10-50 µmol of an isothiocyanate (e.g., sulforaphane or a derivative thereof). In some embodiments, the unit dosage form comprises between 15-50 µmol of an isothiocyanate (e.g., sulforaphane or a derivative thereof). In some embodiments, the unit dosage form comprises between 25-50 µmol of an isothiocyanate (e.g., sulforaphane or a derivative thereof). In some embodiments, the unit dosage form comprises $50\pm10$ µmol of an isothiocyanate (e.g., sulforaphane or a derivative thereof). In some embodiments, the unit dosage form comprises $50\pm25$ µmol of an isothiocyanate (e.g., sulforaphane or a derivative thereof). In some embodiments, the unit dosage form comprises between 50-150 µmol of an isothiocyanate (e.g., sulforaphane or a derivative thereof). In some embodiments, the unit dosage form comprises between 25-150 µmol of an isothiocyanate (e.g., sulforaphane or a derivative thereof). In some embodiments, the unit dosage form comprises between 50-200 µmol of an isothiocyanate (e.g., sulforaphane or a derivative thereof). In some embodiments, the unit dosage form is no greater than 400 (e.g., no greater than 350, 325, 300, 275, 250, 225, 200, 175, 150, 125, 100, or 75) µmol of an isothiocyanate (e.g., sulforaphane or a derivative thereof).

In some embodiments, the effective daily dose is at least 10 (e.g., at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, or 400 or more) µmol of an isothiocyanate (e.g., sulforaphane or a derivative thereof). In some embodiments, the effective daily dose comprises $50\pm25$ µmol of an isothiocyanate (e.g., sulforaphane or a derivative thereof). In some embodiments, the effective daily dose is between 25 and 75 µmol if the patient weighs 100 pounds or less; between 75 and 125 µmol if the patient weighs between 101 to 199 pounds; or between 125 and 175 µmol if the patient weighs more than 200 pounds.

In some embodiments, the compositions provided herein contain from about 10 to about 50 mg of the active ingredient. One having ordinary skill in the art will appreciate that this embodies compositions containing about 5 to about 55, about 15 to about 45, about 25 to about 50, about 10 to about 30, about 30 to about 60, about 20 to about 70, or about 10 to about 20 mg of the active ingredient.

In some embodiments, the sulforaphane or derivative thereof is substantially enantiopure, e.g., for the (R) enantiomer. In some embodiments, the sulforaphane or derivative thereof is a racemic mixture of both the (R) and (S) enantiomers. In some embodiments, the composition is an extract from a cruciferous plant (e.g., broccoli, broccoli sprouts, cauliflower, or kale) that is, optionally, enriched for sulforaphane.

In some embodiments, the pharmaceutical composition or unit dosage forms described herein can be a capsule or tablet comprises between 100 to 500 mg of cruciferous plant (or plant seed or sprout) extract, e.g., an extract from broccoli sprouts, such as BroccoSprouts™. In some embodiments, the pharmaceutical composition or unit dosage form comprises about 250±50 mg (e.g., approximately 232 mg) of cruciferous plant (or plant seed or sprout) extract, e.g., an extract from broccoli sprouts, such as BroccoSprouts™.

Similar dosages may be used of the compounds described herein in the methods and uses provided herein.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound provided herein can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Food Compositions

In some embodiments, a glucosinolate (e.g., a precursor of sulforaphane or sulforaphane derivative) and/or an isothiocyanate (e.g., sulforaphane or a derivative thereof) may be used in the form of a food (e.g., solid food or drink (e.g., beverage)), medical food, or supplement (e.g., nutritional supplement or dietary supplement). A solid food product refers to an edible, ingestible composition, examples of which include, but are not limited to, fruits and vegetables. For example, the food composition can comprise an isolated glucosinolate and, optionally, an isolated enzyme, wherein the enzyme is capable of converting the glucosinolate to a thiocyanate or an isothiocyanate. The enzyme can be any of those described herein (e.g., myrosinase) or otherwise known in the art to have such functional activity.

As used herein, the term "isolated", e.g., as applied to a substance (e.g., a glucosinolate, an isothiocyanate, or an enzyme), refers to a substance that has been separated or purified from components (e.g., proteins or other naturally-occurring biological or organic molecules) which naturally accompany it, e.g., proteins, lipids, carbohydrates, and nucleic acid in plant material. Typically, a substance is isolated when it constitutes at least 60 (e.g., at least 65, 70, 75, 80, 85, 90, 92, 95, 97, or 99) %, by weight, of the total amount of material in a sample. For example, a glucosinolate (e.g., a sulforaphane precursor, such as glucoraphanin) can be isolated from a plant in which the glucosinolate is naturally produced. Likewise, an isothiocyanate compound can be isolated from plant material. The isolated glucosinolate (e.g., a sulforaphane precursor, such as glucoraphanin), isothiocyanate, and/or enzyme can then be added to a food, beverage, medical food, dietary supplement, or other product in a specified amount (e.g., an effective amount) for consumption by, or administration to, a human, e.g., for treating an autism spectrum disorder.

In some embodiments, the food, beverage, medical food, or dietary supplement composition comprises an amount of a glucosinolate (e.g., a sulforaphane precursor, such as glucoraphanin) and enzyme sufficient to produce in the human each day: between 25 and 75 µmol of an isothiocyanate if the human weighs 100 pounds or less; between 75 and 125 µmol of an isothiocyanate if the human weighs between 101 to 199 pounds; or between 125 and 175 µmol of the isothiocyanate if the human weighs more than 200 pounds.

In some embodiments, the composition (e.g., food, beverage, medical food, or dietary supplement composition) comprises, or is, a food bar, yogurt, ice cream, fruit, fruit puree, or cereal. The composition can be a dessert or a confection. Beverage or other liquid compositions can contain a dairy product, fruit juice, or vegetable juice.

As used herein, the term "medical food" refers to a food that is formulated to be consumed or administered enterally under the supervision of a physician and which is intended for the specific dietary management of a disease or condition for which distinctive nutritional requirements, based on recognized scientific principles, are established by medical evaluation (from section 5(b) of the Orphan Drug Act, 21 U.S.C. § 360ee(b)(3)). Thus, medical foods are distinguished from the broader category of foods for special dietary use and from foods that make health claims by the requirement that medical foods be intended to meet distinctive nutritional requirements of a disease or condition, used under medical supervision, and intended for the specific dietary management of a disease or condition. Medical foods are not just those foods recommended by a medical professional as part of an overall diet to manage symptoms or reduce the risk for a disease or condition. Accordingly, medical foods do not include all foods fed to a human (e.g., a human with an autism spectrum disorder).

Likewise, it is also understood that medical foods require some processing or formulation for use in a human, rather than merely a food used in its natural state. Medical foods must be: (a) a food for oral or tube feeding; (b) labeled for the dietary management of a specific condition (e.g., an autism spectrum disorder); and (c) intended to be used under medical supervision (see, e.g., U.S. Food and Drug Administration, Guidance for Industry: Frequently Asked Questions About Medical Foods, Center for Food Safety and Applied Nutrition, May 2007, Revised August 2013).

As used herein, the term "dietary supplement" means "a product intended to supplement the diet that bears or contains one or more of the following dietary ingredients: (A) a vitamin; (B) a mineral; (C) an herb or other botanical; (D) an amino acid; (E) a dietary substance for use by man to supplement the diet by increasing the total dietary intake; or (F) a concentrate, metabolite, constituent, extract, or combination of any ingredient described in clause (A), (B), (C), (D), or (E)." 21 U.S.C. § 321ff). It is understood that a dietary supplement is not food in its natural state. Dietary supplements can also be extracts or concentrates, and may be found in many forms such as tablets, capsules, softgels, gelcaps, liquids, or powders.

Dietary supplements and medical foods can, optionally, be labeled as such, e.g., as required by applicable laws.

A food, beverage, dietary supplement, or medical food described herein may contain, e.g., from about 5 to about 300 µmol, about 25 to about 200 µmol, of an active ingredient, such as an isothiocyanate (e.g., sulforaphane or a derivative thereof). In some embodiments, the food, beverage, dietary supplement, or medical food comprises at least 5 (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, or 400 or more) µmol of an isothiocyanate (e.g., sulforaphane or a derivative thereof). In some embodiments, the food, beverage, dietary supplement, or medical food comprises between 5-100 µmol of an isothiocyanate (e.g., sulforaphane or a derivative thereof). In some embodiments, the food, beverage, dietary supplement, or medical food comprises between 10-50 µmol of an isothiocyanate (e.g., sulforaphane or a derivative thereof). In some embodiments, the food, beverage, dietary supplement, or medical food comprises between 15-50 µmol of an isothiocyanate (e.g., sulforaphane or a derivative thereof). In some embodiments, the food, beverage, dietary supplement, or medical food comprises between 25-50 µmol of an isothiocyanate (e.g., sulforaphane or a derivative thereof). In some embodiments, the food, beverage, dietary supplement, or medical food comprises 50±10 µmol of an isothiocyanate (e.g., sulforaphane or a derivative thereof). In some embodiments, the food, beverage, dietary supplement, or medical food comprises 50±25 µmol of an isothiocyanate (e.g., sulforaphane or a derivative thereof). In some embodiments, the food, beverage, dietary supplement, or medical food comprises between 50-150 µmol of an isothiocyanate (e.g., sulforaphane or a derivative thereof). In some embodiments, the food, beverage, dietary supplement, or medical food comprises between 25-150 µmol of an isothiocyanate (e.g., sulforaphane or a derivative thereof). In some embodiments, the food, beverage, dietary supplement, or medical food comprises between 50-200 µmol of an isothiocyanate (e.g., sulforaphane or a derivative thereof). In some embodiments, the food, beverage, dietary supplement, or medical food comprises no greater than 400 (e.g., no greater than 350, 325, 300, 275, 250, 225, 200, 175, 150, 125, 100, or 75) µmol of an isothiocyanate (e.g., sulforaphane or a derivative thereof).

In some embodiments, the food, beverage, dietary supplement, or medical food is labeled such that the effective daily dose is at least 10 (e.g., at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, or 400 or more) µmol of an isothiocyanate (e.g., sulforaphane or a derivative thereof). In some embodiments, the effective daily dose comprises 50±25 µmol of an isothiocyanate (e.g., sulforaphane or a derivative thereof). In some embodiments, the effective daily dose is between 25 and 75 µmol if the patient weighs 100 pounds or less; between 75 and 125 µmol if the patient weighs between 101 to 199 pounds; or between 125 and 175 µmol if the patient weighs more than 200 pounds.

In some embodiments, the food, beverage, dietary supplement, or medical food provided herein contains from about 10 to about 50 mg of the active ingredient. One having ordinary skill in the art will appreciate that this embodies compositions containing about 5 to about 55, about 15 to about 45, about 25 to about 50, about 10 to about 30, about 30 to about 60, about 20 to about 70, or about 10 to about 20 mg of the active ingredient.

In some embodiments, the sulforaphane or derivative thereof is substantially enantiopure, e.g., for the (R) enantiomer. In some embodiments, the sulforaphane or derivative thereof is a racemic mixture of both the (R) and (S) enantiomers. In some embodiments, the composition is an extract from a cruciferous plant (e.g., broccoli, broccoli sprouts, cauliflower, or kale) that is, optionally, enriched for a glucosinolate (e.g., a glucoraphanin, such as sulforaphane).

In some embodiments, the medical food or supplement described herein can be a capsule or tablet comprises between 100 to 500 mg of cruciferous plant (or plant seed or sprout) extract, e.g., an extract from broccoli sprouts, such as BroccoSprouts™. In some embodiments, the medical food or supplement comprises about 250±50 mg (e.g., approximately 232 mg) of cruciferous plant (or plant seed or sprout) extract, e.g., an extract from broccoli sprouts, such as BroccoSprouts™. Methods for making such products are described herein and exemplified in the working examples.

Applications

Autism Spectrum Disorders

Also featured herein are methods for treating an autism spectrum disorder. McPartland and Volkmar (2012) *Handb Clin Neurol* 106:407-418. Autism spectrum disorder (ASD) and autism are both general terms for a group of complex disorders of brain development. These disorders are characterized, in varying degrees, by difficulties in social interaction, verbal and nonverbal communication and repetitive behaviors. These disorders include, but are not limited to, autistic disorder, childhood disintegrative disorder, pervasive developmental disorder-not otherwise specified (PDD-NOS) and Asperger syndrome.

Classical autism is a highly variable neurodevelopmental disorder. It is typically diagnosed during infancy or early childhood. According to the criteria set out in the DSM-IV (see working examples), diagnosis of autism requires a triad of symptoms to be present: including (i) impairments in social interaction, (ii) impairments in communication and (iii) restricted and repetitive interests and behaviors. Other dysfunctions, such as atypical eating, are also common but are not essential for diagnosis. Social impairments include: (i) impairments in the use of multiple nonverbal behaviors (e.g. eye contact) to regulate social interaction; (ii) failure to develop peer relationships appropriate to developmental level; (iii) lack of spontaneous seeking to share enjoyment, interests, or achievements; (iv) lack of social or emotional reciprocity. Communication impairments in autism may present in one or more of the following ways: delay in (or total lack of) the development of spoken language; marked impairment in the ability to initiate or sustain a conversation; stereotyped and repetitive use of language; and/or a lack of spontaneous make-believe play.

Asperger syndrome or Asperger Disorder is similar to autism, and shares certain features. Like autism, Asperger syndrome is also characterized by impairment in social interaction and this is accompanied by restricted and repetitive interests and behavior. Thus, diagnosis of Asperger syndrome is characterized by the same triad of impairments as autism. However, Asperger syndrome is typically less severe in symptomology than classical autism and Asperger's patients may function with self-sufficiency and lead relatively normal lives.

Childhood disintegrative disorder (CDD), also known as Heller syndrome, is a condition in which children develop normally for at least two years, but then demonstrate a severe loss of social, communication and other skills. Childhood disintegrative disorder is very much like autism and both involve normal development followed by significant loss of language, social play and motor skills. Diagnosis of CDD is dependent on dramatic loss of previously acquired skills in two or more of the following areas: language, social skills, play, motor skills (such as a dramatic decline in the ability to walk, climb, grasp, etc.), bowel or bladder control (despite previously being toilet-trained). The loss of developmental skills may be abrupt and take place over the course of days to weeks or may be more gradual.

Pervasive Developmental Disorder-Not Otherwise Specified (PDD-NOS) is an ASD that describes patients exhibiting some, but not all, of the symptoms associated with other well defined ASDs. The key criteria for diagnosis of an ASD include difficulty socializing with others, repetitive behaviors, and heightened sensitivities to certain stimuli. These are all found in the ASDs described above. However, autism, Asperger syndrome, and childhood disintegrative disorder all have other features that enable their specific diagnosis. When specific diagnosis of one of these four disorders cannot be made, but ASD is apparent, a diagnosis of PDD-NOS is made. Such a diagnosis may result from symptoms starting at a later age than is applicable for other conditions in the spectrum.

ASD can be associated with intellectual disability, difficulties in motor coordination and attention and physical health issues such as sleep and gastrointestinal disturbances. Some persons with ASD excel in visual skills, music, math and art.

Methods for Treatment

The compositions described herein can be administered to a subject, e.g., a human subject, using a variety of methods that depend, in part, on the route of administration. The route can be, e.g., oral, inhalation, intravenous injection or infusion (IV), subcutaneous injection (SC), intraperitoneal (IP) injection, or intramuscular injection (IM).

The terms "therapeutically effective amount" or "therapeutically effective dose," or similar terms used herein are intended to mean an amount of an agent (e.g., a glucosinolate (e.g., glucoraphanin), sulforaphane, or a derivative thereof) that will elicit the desired biological or medical response (e.g., an improvement in one or more symptoms of an autism spectrum disorder). Toxicity and therapeutic efficacy of such compositions can be determined by known pharmaceutical procedures in cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A compound that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compounds lies generally within a range of circulating concentrations of the compounds that include the ED50 with little or no toxicity. The dosage may vary within this range depending upon the dosage form employed and the route of administration utilized.

A dose can be formulated in animal models to achieve a circulating plasma concentration range that includes the IC50 (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, a food, beverage, dietary supplement, medical food, or pharmaceutical composition described herein can be administered or consumed with a meal. A meal represents particularly a standard meal, namely breakfast, lunch or dinner. Food may increase the absorption of sulforaphane or derivative by the gut. The increase in oral absorption and systemic bioavailability a compound is determined by measuring the plasma concentration of calcitonin achieved after administration of the drug at various intervals prior to a meal and at mealtime. Typically, the plasma concentration is measured at predetermined periods after the administration of the drug so as to determine the maximum plasma concentration (Cmax) and the total amount absorbed as determined by the area under the curve (AUC).

In some embodiments, a food, beverage, dietary supplement, medical food, or pharmaceutical composition described herein is to be administered to a human in conjunction with a low calorie or low fat diet.

In some embodiments, a food, beverage, dietary supplement, medical food, or pharmaceutical composition is to be administered to the human in conjunction with one or more other therapies of an autism spectrum disorder. For example, sulforaphane or a derivative thereof can be administered to a human along with one or more of risperidone; aripiprazole; a selective serotonin reuptake inhibitor (SSRI), such as fluoxetine and sertraline; naltrexone; olanzapine; fluvoxamine; clomipramine; haloperidol; thiodazine; fluphenazine; chlorpromazine; olanzapine (Zyprexa®); ziprasidone (Geodon®); and methylphenidate. Such medicines fall under categories of anti-depressants, anti-anxiety drugs, antipsychotics, or inattention/hyperactivity drugs. In some embodiments, an isothiocyanate (e.g., sulforaphane or a derivative thereof) is to be administered with an anti-seizure drug. The anti-seizure drug can be, e.g., carbamazepine (Tegretol®), lamotrigine (Lamictal®), topiramate (Topamax®), or valproic acid (Depakote®).

In some embodiments, a food, beverage, dietary supplement, medical food, or pharmaceutical composition is not to be administered if a human is being administered concurrently with (or, e.g., less than 30 (e.g., less than 29, 28, 27, 26, 25, 24, 23, 22, 21, 20, 19, 18, 17, 16, 15, 14, 13, 12, 11, 10, 9, 8, 7, 6, 5, 4, 3, 2, or 1) day(s) prior to) administration of a drug associated with increased risk for seizures.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject relative to a subject which does not receive the composition.

A therapeutic composition described herein (e.g., a food, beverage, dietary supplement, medical food, pharmaceutical composition, or any other composition comprising an isothiocyanate, a glucosinolate, an enzyme, sulforaphane, or a derivative thereof) can replace or augment a previously or currently administered therapy. For example, upon treating with sulforaphane or a derivative thereof, administration of the one or more additional active agents can cease or diminish, e.g., be administered at lower levels. In some embodiments, administration of the previous therapy can be maintained. In some embodiments, a previous therapy will be maintained until the level of the isothiocyanate (e.g., sulforaphane or a derivative thereof) reaches a level sufficient to provide a therapeutic effect. The two therapies can be administered in combination.

Monitoring a subject (e.g., a human patient) for an improvement in an autism spectrum disorder, as defined herein, means evaluating the subject for a change in a disease parameter, e.g., an improvement in one or more symptoms of a given disorder. Methods for evaluating patients with an autism spectrum disorder, including evaluating improvements in their symptoms following a treatment, are known in the art and exemplified in the working examples. For example, a medical practitioner can look for changes in Aberrant Behavior Checklist (ABC) scores, Social Responsiveness Scale (SRS) scores, Clinical Global Impression-Improvement (CGI-I) scores, or Clinical Global Impression-Severity (CGI-S) scores from baseline to a predetermined point in time following initiation of treatment. The symptoms of autism spectrum disorders are well known in the art of medicine. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for an autism spectrum disorder described herein.

The following examples are intended to illustrate, not to limit, this disclosure.

EXAMPLES

Example 1. Materials and Methods

Preparation of Sulforaphane-Rich Broccoli Sprout Extracts.

Sulforaphane-rich broccoli sprout extract (SF-BSE) was prepared by the Cullman Chemoprotection Center at Johns Hopkins University essentially as described in Egner et al. (2014) *Cancer Prev Res* 7:813). In brief, specially selected BroccoSprouts™ seeds were surface-disinfected and grown (sprouted) for three days in a commercial sprouting facility under controlled light and moisture conditions. A boiling water extract was prepared, filtered, cooled and treated with the enzyme myrosinase (from daikon sprouts) in order to convert precursor glucosinolates to isothiocyanates, and then lyophilized at a food processing facility (Oregon Freeze Dry, Albany, Oreg.). The lyophilized powder (216 µmol SF/g powder) was encapsulated into #1 gelcaps by ALFA Specialty Pharmacy (Columbia, Md.). Each capsule contained 50 µmol SF (232 mg of BSE); placebo capsules were filled with microcrystalline cellulose. The powders (bulk and capsules) were maintained at $-20°$ C. and repeatedly checked for microbial contaminants and SF titer prior to conveyance to the study site pharmacy to be dispensed to patients.

Study Protocol.

Written informed consent was obtained from all participants involved in the study described herein either directly, or from parents or caregivers. All participants met criteria for autistic disorder. See American Psychiatric Association (2000) Diagnostic and Statistical Manual of Mental Disorders (DSM-IV; $4^{th}$ ed.) (American Psychiatric Association, Arlington). Forty-four male ASD patients were enrolled. The Autism Diagnostic Observation Schedule (ADOS), performed by a trained psychologist/tester (in 43 participants) and/or DSM-IV (supra) checklist of symptoms performed by a trained physician (2 participants), were used to confirm the diagnosis of autism at the screening visit. All participants were moderately to severely autistic on the CGI-S(Clinical Global Impression Severity Scale; Choque et al. (2014) *J Autism Dev Disord* 44(7):1773-1778), with varied cognitive capacity (FIG. 1).

Eligibility criteria included: (1) male gender, (2) age 13 to 30, (3) no concurrent chronic illness, (4) no history of active seizures within one year prior to starting treatment, and (5) normal liver, renal, and thyroid functions. Participants continued their regular medications, if any, during the study.

Participants were assigned to receive either placebo or sulforaphane according to computer-generated randomly-permuted blocks of three assignments with sulforaphane and placebo treatments allocated in a 2:1 ratio in two strata defined by parent-reported history of improvement in behavior during febrile illness. Physicians and study staff were blind to group assignment. Forty-four subjects were selected to provide at least 80% power to test the primary hypothesis for the Social Responsiveness Scale (SRS) using a two-tailed two-sample t-test with $a=0.05$ and assuming that the true difference in average change in SRS was 15 units with standard deviation of 16 units. This is roughly twice the average magnitude of natural change observed over 1 year among male children and adolescents with ASD (Constantino et al. (2009) *Dev Psychopathol* 21(1):127-138).

The study involved seven visits: (i) screening, (ii) randomization and initiation of treatment, (iii) a visit at 24 hours post initiation of treatment, and then follow-up visits at (iv) 4, (v) 10, and (vi) 18 weeks after the first dose. Treatment was discontinued after the 18-week visit, and participants returned at 22 weeks. Medical history, physical exam including vital signs, adverse event reporting, and SRS, ABC (Aberrant Behavior Checklist; Marshburn et al. (1992) *J Autism Dev Disord* 22(3):357-373), and CGI-I (Clinical Global Impression Improvement; The OSU Research Unit on Pediatric Psychopharmacology (2005) OSU Autism Rating Scale. The Ohio State University, Columbus, Ohio) were performed (FIG. 2). At the 4-, 18-, and 22-week visits, hematology, chemistry, and urinalysis were performed.

All families were contacted after the final participant completed follow-up and asked for their impressions of the study and their child's progress while under treatment. They were then informed whether he received sulforaphane or placebo.

Administration of Medication and Protocol Schedule.

Capsules of sulforaphane-rich broccoli sprout extracts were maintained at −20° C., and checked periodically microbiologically, and for sulforaphane titer (Egner et al. (2011) *Cancer Prev Res* 4(3):384-395). Indistinguishable placebo capsules contained microcrystalline cellulose. Sulforaphane or placebo was administered daily for 18 weeks. The participants were dosed according to body weight: 50 µmol (1 capsule) of sulforaphane for <100 lb, 100 µmol (2 capsules) for 101-199 lb, and 150 µmol (3 capsules) for >200 lb. Placebo recipients received equivalent numbers of capsules according to their weight. Capsules were dispensed to participants in sealed bottles with instructions to keep them in a household freezer.

Behavioral Outcome Measures.

The Aberrant Behavior Checklist (ABC) is a parent- or caregiver-reported 58-item questionnaire, designed to assess medication effects; each item is scored on a scale of increasing severity from 0 to 3 (Marshburn et al., supra). ABC also assesses several subdomains (irritability, lethargy, stereotypy, and hyperactivity). The Social Responsiveness Scale (SRS) is a parent- or caregiver-reported 65-point social communication questionnaire that covers 5 subscales (awareness, cognition, communication, motivation, and autistic mannerisms) (Constantino et al., supra). Each SRS item is rated on a scale of 1 to 4; the total score was our primary efficacy endpoint. The Ohio Autism Clinical Global Impression Severity Scale (CGI-S, also designated OACIS-S, and only measured at screening) (Choque et al., supra; OSU Autism Rating Scale, supra) is a clinician-rated assessment of the severity of autistic behavior (in increasing order of severity from 1 to 7) and includes the following subdomains: global autism severity, social interaction, aberrant behavior, repetitive or ritualistic behaviors, verbal and nonverbal communication, hyperactivity/inattention, anxiety, sensory sensitivities and restricted/narrow interests. The Ohio Autism Clinical Global Impressions Improvement Scale (CGI-I or OACIS-I) is a clinician-rated assessment of how much the patient's behavior has changed during an intervention.

Statistical Evaluation.

Figure 3:
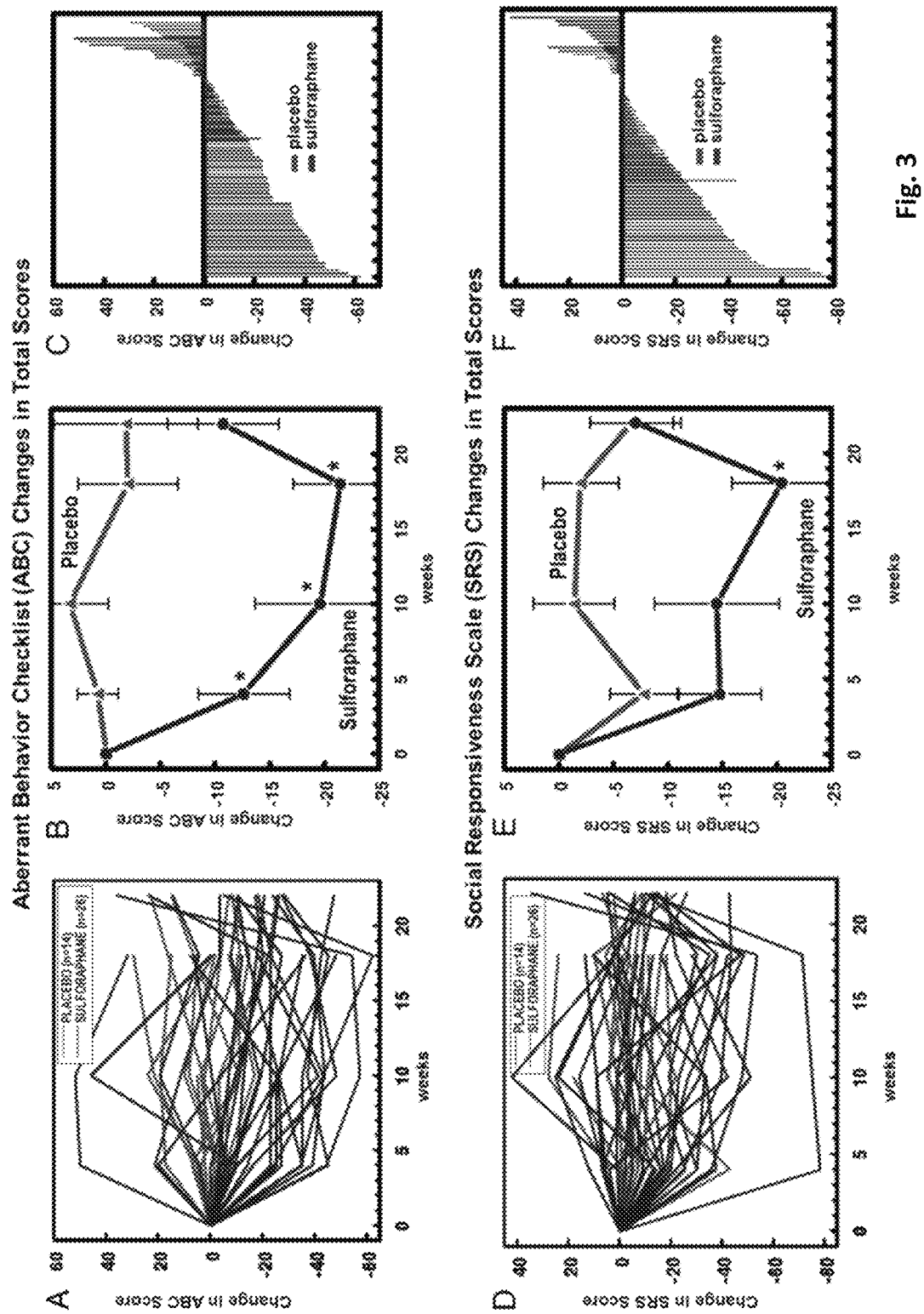
FIGS. 3A-3F are a series of graphs depicting the changes in total ABC (Aberrant Behavior Checklist) and SRS (Social Responsiveness Scale) scores of patients during the clinical study. Forty male ASD participants who were treated daily with either placebo (shown in red; initially n=14) or sulforaphane (shown in blue; initially n=26) for 4, 10, and 18 weeks, followed by a terminal 4-week untreated period (22 weeks).

Forty-four subjects were originally enrolled and randomized to sulforaphane treatment (n=29) or placebo (n=15); 4 subjects discontinued participation in the study before the first (4-week) return visit. Behavior scores for the remaining 40 participants, who completed at least part of the outcome measure evaluations (14 placebo and 26 sulforaphane), are described in our primary results and shown in FIGS. 3(A-F), 4, 5(A and B), and 6 (A and B). To compensate for incidental changes in ABC/SRS scores due to normal fluctuation, these scores were obtained at both screening and randomization visits, and their averages were used to compare with subsequent ABC/SRS scores. The primary analysis used the differences between scores of individuals at 4, 10, 18, and 22 weeks from their respective average pre-treatment values. The difference between the sulforaphane and placebo treatment groups in the change in ABC and SRS scores from baseline to 18 weeks, and their reversion to baseline at 22 weeks, was the measure of efficacy.

Each outcome was modeled in a shared-baseline mixed effects general linear model with fixed effects for visit and the interaction of post-randomization visit and treatment group and random participant-specific intercepts and slopes with unstructured covariance. The absence of a main effect for treatment (i.e., a "shared baseline") properly reflects the true state of the population sampled prior to randomization and has the advantage of adjusting for any chance differences at baseline in a manner similar to ANCOVA (Liang and Zeger (2000) *Indian J Stat* 62(1):134-148). Linear contrasts of least-square means were used to estimate changes from baseline between treatment and control groups at each follow-up visit. Given its assumptions, the mixed model yields estimates that are unbiased as long as loss to follow-up and missing test scores are predictable from observed scores under assumptions of the model. An intention-to-treat analysis that included all 44 participants led to similar conclusions.

Statistical analyses were performed with SAS® 9.3 software (SAS Institute, Cary, N.C.), and Stata® v.11.2 (Statacorp, College Station, Tex.).

Safety and Tolerance.

Adverse event monitoring and documentation by severity, duration, and relatedness were performed by a physician at each follow-up visit. Study drug pause and stop rules were formulated as follows: In case of any significant adverse events, or if laboratory values were above the study eligibility rules (i.e., AST or ALT>1.5× upper limit of normal, serum creatinine >1.2 mg/dL or TSH outside normal limits), study medication was to be stopped for 2 weeks and subjects re-evaluated. If laboratory studies returned to normal and no more adverse events were noted, the medication was to be restarted. Otherwise, the study medication was to be stopped indefinitely. Study drug safety and adherence to the protocol were monitored at quarterly meetings of a Data Safety Monitoring Board constituted by 3 members at the Lurie Center for Autism.

Quality of Data Certification.

An on-site FDA Good Clinical Practice Raw Data Audit was performed on May 19-21, 2014. The inspection was performed by Philippe Ourisson, Ph.D. (Manager, Quality Assurance and Scientific Support), and confirmed by Paul Swidersky (President), Quality Associates, Inc., 8161 Maple Lawn Boulevard, Fulton, Md. The folder of each of the 44 subjects was reviewed. Every informed consent form was examined. All inclusion/exclusion criteria were verified. Most baseline physicals and all subject evaluations through week 22 were examined, then transcribed to a spreadsheet. No evidence was obtained that there were significant errors in collecting the data and transferring the results to the spreadsheets.

Statistical Analysis of Outcome Measures and Intention-to-Treat Analysis.

The study hypotheses concerned differences between the sulforaphane and placebo treatment groups in the average change in ABC and SRS scores from baseline to 18 weeks, and their reversion to baseline at 22 weeks. CGI-I scores were examined as a secondary outcome at the same time points. Of the 44 subjects originally enrolled and randomized to sulforaphane treatment (n=29) or placebo (n=15), 4 subjects discontinued participation in the study before the first return visit, 4 weeks after treatment initiation. In the body of the paper, change scores calculated as the change from baseline to each follow-up time point for each participant were analyzed. The 4 participants who discontinued early were not included in the main analyses.

An alternative, intention-to-treat (ITT) analysis included all randomized participants. Each outcome was modeled in a mixed effects general linear model with fixed effects for visit and the interaction of post-randomization visit and treatment group and random participant-specific intercepts and slopes with unstructured covariance. The absence of a main effect for treatment (i.e., a "shared baseline") properly reflects the true state of the population sampled prior to randomization and has the advantage of adjusting for any chance differences at baseline in a manner similar to ANCOVA. The model was used to estimate the difference between treatment and control in mean change from baseline at each time point. Given its assumptions, the mixed model yields estimates that are unbiased as long as missing test scores are predictable from observed scores. In this model, the baseline scores (the mean of scores at the screening and randomization visits) of the 4 participants lost to follow-up were included in the analysis, with all participants analyzed according to their assigned treatment group without regard to whether they continued treatment. The test statistic used was the difference between the two treatment groups in the average change in SRS from baseline to 18 weeks. We used a two-tailed test at a=0.05. To quantify the change in efficacy after 4 weeks without treatment we estimated the difference in the treatment-placebo comparison at 22 versus 18 weeks, by a simple linear contrast of the estimated model parameters.

By mixed model analysis of the ITT sample, the sulforaphane group had significantly greater improvement in their overall SRS and ABC scores compared to the placebo group. After 18 weeks of treatment, the sulforaphane group had a reduction in SRS total score of 15.3 units from baseline compared to a decrease of 3.2 units in the placebo group (difference=12.1 units, P=0.01). After subjects stopped the medication, the SRS scores tended to revert to the mean (although incompletely), with the average decrease of SRS total score from baseline to 22 weeks being 6 units in the sulforaphane group and 2.9 units in the placebo group (difference=3.1 units, P=0.70).

The effect of sulforaphane on ABC total scores was comparable, with a decrease of 17.6 units among participants randomized to active treatment compared to a decrease of 0.08 unit in the placebo group (difference=17.5 units, P=0.0001). As with SRS scores, ABC total scores also tended to revert to baseline after stopping treatment, such that the average decrease of total ABC score from baseline to 22 weeks was 8.8 units in the sulforaphane group, compared to 0.08 unit in the placebo group (difference=8.9 units, P=0.28).

Guided by the power analysis and sample size calculation discussed in the paper (indicating power to detect a 15-point change in total SRS score), a positive response to treatment was defined post hoc as a 30% decrease from baseline on SRS and ABC scores. After conservatively considering the 4 dropouts (1 on placebo and 3 on sulforaphane) as not meeting the 30% reduction threshold, ABC scores at 18 weeks were available for 39 participants (11 placebo and 28 sulforaphane), and SRS scores at 18 weeks were available for 41 participants (12 placebo and 29 sulforaphane). Additionally, 3 participants on sulforaphane inexplicably had >30% reduction in their ABC scores from baseline, whereas they were not improved either on CGI-I (OACIS-I) or post-study parent interviews. These 3 participants were conservatively considered as not meeting the 30% reduction threshold. With that adjustment, 31% (9/29) participants on sulforaphane had a positive response on SRS compared to 0% (0/15) participants on placebo (Fisher exact test, P=0.018). Similarly, 44.8% (13/29) of participants taking sulforaphane had a positive response on ABC compared to 13% (2/15) patients on placebo (P=0.048). Also consistent with the "per-protocol" findings reported in the paper, an ITT analysis suggested that more participants in the sulforaphane compared to the placebo group experienced a positive response on several subdomains of the CGI-Improvement scale. After 18 weeks of treatment, 41% (12/29) participants taking sulforaphane were "much improved" or "very much improved" on the social interaction subdomain of the CGI-I as compared to 0% (0/15) of participants on placebo (P=0.003). Forty-eight percent (14/29) of participants on sulforaphane were "much improved" or "very much improved" on the aberrant or abnormal behavior subdomain of the CGI-I as compared to 6.7% (1/15) of placebo participants (P=0.007). Thirty-eight percent (11/29) participants on sulforaphane were "much improved" or "very much improved" on the verbal communication subdomain of the CGI-I as compared to 6.7% (1/15) of placebo participants (P=0.035).

In conclusion, the intention-to-treat data analysis is presented as the most conservative approach to evaluation of the data, and results in similar findings that confirm the per-protocol analysis. Moreover, whether those participants who dropped out of the study are included or excluded does not detract from the statistical validity of sulforaphane's effects in this clinical trial of young men with ASD.

Example 2. Results of the Study

Participant Characteristics.

Figure 7:
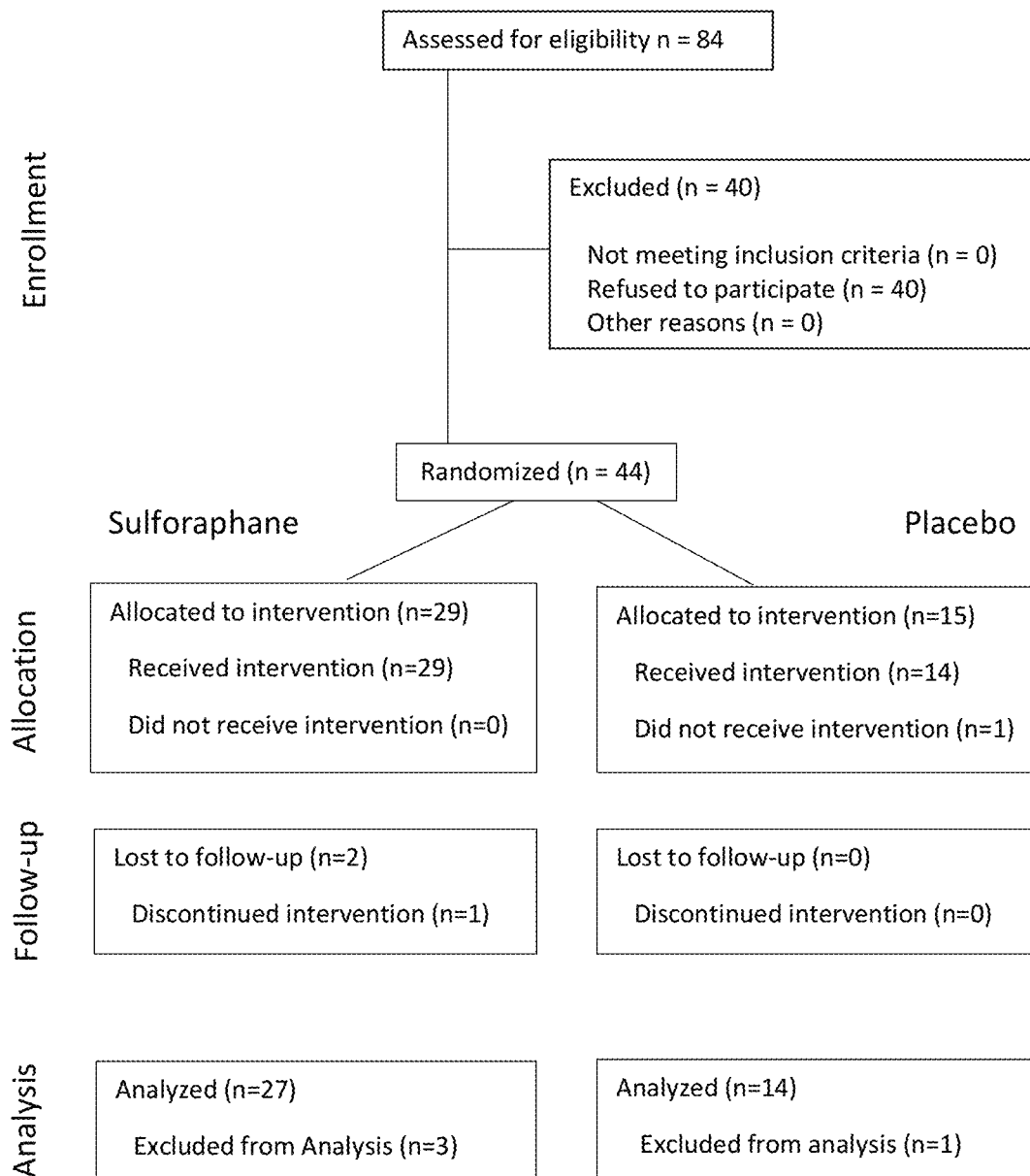
FIG. 7 is a flow diagram of progress through phases of the study.

More than 90% of all scheduled tests were completed on the 40 participants who received placebo or sulforaphane treatment and returned for the first return visit (week 4). Twenty-two participants (6 placebo, 16 sulforaphane) were also tested at 22 weeks, 4 weeks after treatment ended (FIG. 7). Four participants (1 placebo, 3 sulforaphane) were lost to follow-up prior to their first on-treatment visit.

Participants, all male, were 13-27 years old at enrollment (median: 17 years). A history of behavioral improvements with fever was given by a large majority (32 of 40; 80%) of participants. Participants in sulforaphane and placebo groups were well matched, and did not differ at baseline with respect to various demographic, behavioral and clinical features, behavioral outcome score measures, abnormalities in physical examination, blood chemistries, hematology, and urinalysis (FIG. 1).

Analysis of Outcome Measures.

The total and the changes in total ABC and SRS behavioral scores of the 26 sulforaphane-treated and 14 placebo recipients from enrollment to the 18-week end of treatment and after a 4-week recovery period are shown in FIGS. 2-6. Treatment group mean ABC scores differed significantly at 4, 10, and 18 weeks (FIGS. 3B and 3E for ABC and SRS, respectively). At 18 weeks there was a 34% reduction in ABC and a 17% reduction in SRS scores, and these trended toward non-significant differences upon cessation of treatment (FIGS. 3B, 3E, 6A, and 6B).

Figure 4:
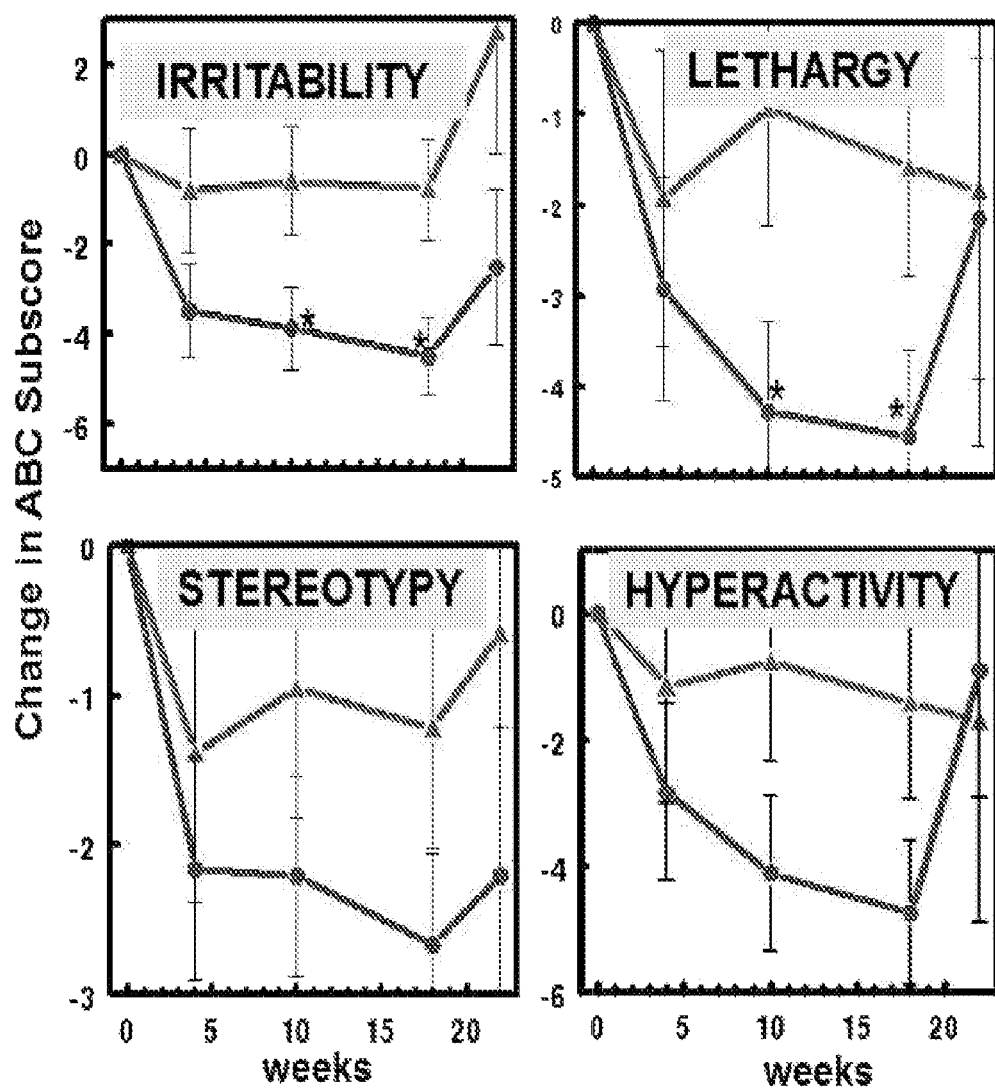
FIG. 4 is a series of line graphs depicting the changes in Aberrant Behavior Checklist (ABC) subscores for irritability, lethargy, stereotypy, and hyperactivity. After 4, 10, and 18 weeks of treatment with sulforaphane or placebo, and a 4-week untreated recovery period (22 weeks). Raw, unadjusted mean values of changes (±S.E.M.) for sulforaphane- and placebo-treated participants are shown. Changes were significant at the 95% confidence level (*) for both irritability and lethargy at 10 and 18 weeks of treatment.

Significantly greater improvement was observed among participants randomized to sulforaphane at 4, 10, and 18 weeks for irritability, lethargy, stereotypy and hyperactivity subscales of the ABC, and in awareness, communication, motivation and mannerisms subscales of SRS (FIGS. 4, 6A, and 6B). After stopping sulforaphane treatment, both ABC and SRS subscores tended to revert toward baseline.

On subscale analysis of CGI-I scale scores at 18 weeks (FIGS. 6A and 6B), 46% (12/26), 54% (14/26), and 42% (11/26) of sulforaphane recipients were much or very-much improved on social interaction, aberrant behavior, and verbal communication, respectively, compared to 0% (0/11; P=0.007), 9% (1/11; P=0.014), and 0% (0/11; P=0.015), respectively, for placebo recipients.

Figure 5A:
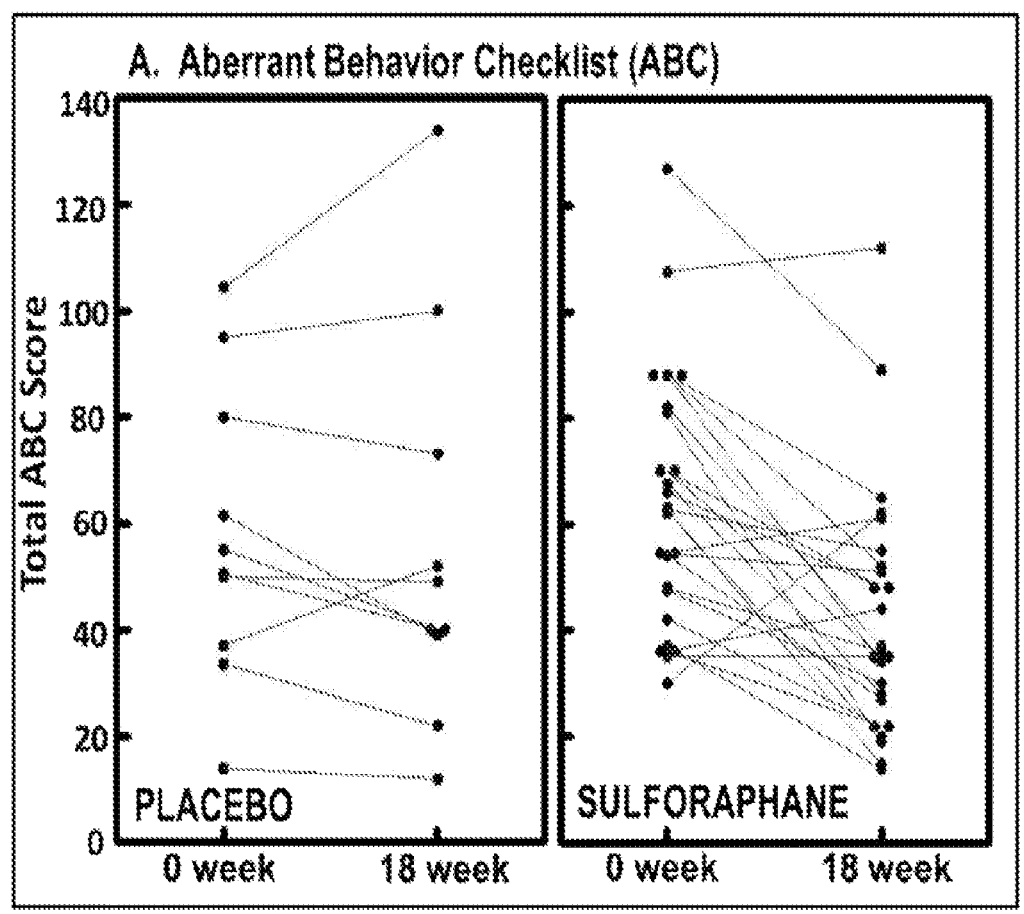
FIGS. 5A and 5B are line graphs depicting total scores for (FIG. 5A) Aberrant Behavior Checklist (ABC) and (FIG. 5B) Social Responsiveness Scale (SRS) of individual placebo- and sulforaphane-treated participants at baseline and after 18 weeks. At 18 weeks, total ABC scores were available for 35 (10 placebo and 25 sulforaphane), and total SRS scores for 37 (11 placebo and 26 sulforaphane). Only the differences for sulforaphane treatment were significant at 18 weeks, thus a change in score of from 62.4 to 45.0 on the ABC scale (FIG. 5A) was significant ($P<0.001$), and a change in score of from 121.5 to 105.2 on the SRS scale (FIG. 5B) was significant ($P<0.001$). Means for the subjects shown, at 1 and 18 weeks respectively, for placebo treatment, were 62.4 and 62.6 on the ABC scale, and 121.5 and 117.5 on the SRS scale.
Figure 5B:
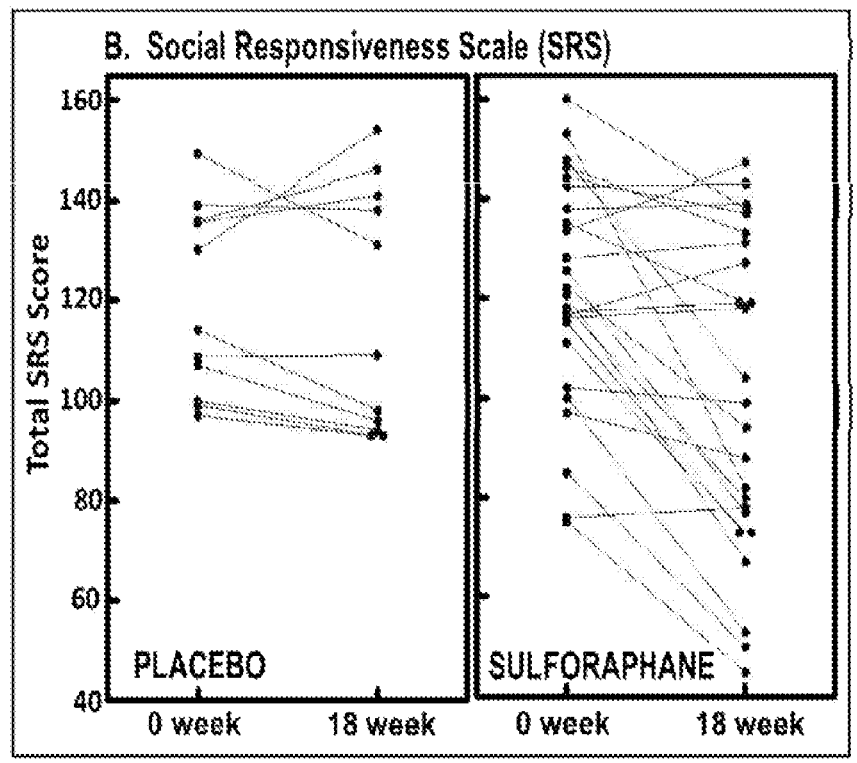

Individual changes in total ABC and SRS scores from basal levels to 18 weeks are shown in FIGS. 5A and 5B. A positive response was defined post-hoc as a 30% decrease from baseline in total ABC and SRS scores. Thirty-five percent (9/26) of participants on sulforaphane had a positive response on SRS compared to 0% (0/11) on placebo (Fisher exact test P=0.036), and 60% (15/25) of participants receiving sulforaphane had a positive response on ABC compared to 20% (2/10) on placebo (P=0.059).

Clinical impressions made during the study, while blind to group assignment, were that 13 of the 40 participants improved noticeably with respect to sociability and behavior, usually observable by 4 weeks; all were receiving sulforaphane. In queries to families and caregivers, before unblinding, 17 of 26 whose sons had taken sulforaphane reported gradual changes within the first month of treatment and correctly surmised their group assignment, whereas the remaining 9 on sulforaphane, and all but 1 of 14 who received placebo, were not improved, and believed that their sons had not received sulforaphane. Positive responses to sulforaphane were spontaneously reported by parents and caretakers, who commented (before disclosure of treatment category) on improved social responsiveness, behavioral compliance and calmness in the subjects with ASD who were taking the active compound.

Safety and Adverse Events.

Sulforaphane treatment effectively improved core aberrant behaviors of ASD, and was safe and well-tolerated (FIG. 8). Notably, none of the laboratory results were outside normal ranges at any time point (FIG. 9). Unexpectedly, the sulforaphane group gained significantly more weight over the 18-week period, compared to placebo (4.31 vs. 0.31 lb, P=0.056). Pulse rate was lower in the sulforaphane group both at baseline and during the study. Thirty-six adverse events were noted during the trial. Vomiting, increased aggressions, abdominal pain, increased flatulence, irritability, constipation, diarrhea, fever, headache and exacerbation of seasonal allergies were reported in 12-19 percent of participants on sulforaphane; their incidence was the same in the placebo groups (P>0.10).

Two participants had single unprovoked seizures: one after 3 weeks on sulforaphane, with an undisclosed history of recent seizures; the other 3 weeks after discontinuing treatment and a past (more than 1 year) history of well-controlled seizures with anti-epileptic drugs. Although patients with autism are predisposed to seizures, we cannot rule out the possibility of seizures as a possible adverse effect of sulforaphane in ASD.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating an autism spectrum disorder in a human, the method comprising administering to the human daily a composition comprising an effective amount of an isothiocyanate, to thereby treat the disorder, wherein the effective amount is: between 25 and 75 µmol if the human weighs 100 pounds or less; between 75 and 125 µmol if the human weighs between 101 to 199 pounds; or between 125 and 175 µmol if the human weighs more than 200 pounds.

2. The method of claim 1, wherein the amount is 50 µmol, if the human weighs 100 pounds or less; 100 µmol if the human weighs between 101-199 pounds; or 150 µmol if the human weighs more than 200 pounds.

3. The method of claim 1, wherein the amount is administered daily as one dose.

4. The method of claim 1, wherein the amount is administered daily as more than one dose.

5. The method of claim 1, wherein the isothiocyanate is administered to the human for at least 18 weeks.

6. The method of claim 1, wherein the disorder is autism.

7. The method of claim 6, wherein the human has moderate to severe autism.

8. The method of claim 1, wherein the amount is effective to reduce the severity of one or more behavioral symptoms of the disorder.

9. The method of claim 1, wherein the human has a medical history of behavioral improvements with fever.

10. The method of claim 1, wherein the isothiocyanate is sulforaphane or a derivative thereof.

11. The method of claim 10, wherein the sulforaphane is enantiopure for the (R) enantiomer.

12. The method of claim 1, wherein the isothiocyanate has been extracted from a cruciferous vegetable or seeds thereof.

13. The method of claim 1, wherein the isothiocyanate has any one of the structural formulas (II) to (LII).

14. The method of claim 1, wherein the isothiocyanate has at least 50% of the activity of an equivalent molar amount of sulforaphane to induce expression of a heat shock protein in cells in vitro.

15. The method of claim 1, wherein the composition is a pharmaceutical composition.

16. The method of any claim 1, wherein the composition is a medical food or a dietary supplement.

17. The method of claim 1, wherein the composition is a food.

18. A method for treating an autism spectrum disorder in a human, the method comprising administering to the human an effective amount of an isothiocyanate to thereby treat the disorder, wherein the human has not experienced a seizure within one year prior to administering the isothiocyanate.

19. A method for treating an autism spectrum disorder in a human, the method comprising administering to the human: (a) an effective amount of an isothiocyanate to thereby treat the disorder; and (b) an effective amount of an anti-seizure drug.

20. A method for treating an autism spectrum disorder in a human, the method comprising administering to the human an effective amount of an isothiocyanate to thereby treat the disorder, wherein the human is not concurrently being treated with a drug associated with increased risk of seizure.

21. A method for treating an autism spectrum disorder in a human, the method comprising:
(i) administering to the human an effective amount of an isothiocyanate to thereby treat the disorder; and
(ii) monitoring the human for the occurrence of seizures.

22. A method for treating an autism spectrum disorder in a human, the method comprising administering to the human an effective amount of an isothiocyanate to thereby treat the disorder, wherein the isothiocyanate is to be administered in conjunction with a reduced calorie diet.

* * * * *